US011291844B2

(12) United States Patent
Gross

(10) Patent No.: US 11,291,844 B2
(45) Date of Patent: Apr. 5, 2022

(54) PROSTHETIC AORTIC VALVE PACING SYSTEM

(71) Applicant: E-VALVE SYSTEMS LTD., Herzliya (IL)

(72) Inventor: Yossi Gross, Moshav Mazor (IL)

(73) Assignee: E-VALVE SYSTEMS LTD., Herzliya (IL)

( * ) Notice: Subject to any disclaimer, the term of this patent is extended or adjusted under 35 U.S.C. 154(b) by 0 days.

(21) Appl. No.: 17/328,588

(22) Filed: May 24, 2021

(65) Prior Publication Data

US 2021/0283397 A1 Sep. 16, 2021

Related U.S. Application Data

(63) Continuation-in-part of application No. 16/868,121, filed on May 6, 2020, now Pat. No. 11,013,597, (Continued)

(30) Foreign Application Priority Data

Jan. 7, 2019 (EP) ..................... 19150581

(51) Int. Cl.
*A61N 1/362* (2006.01)
*A61F 2/24* (2006.01)
(Continued)

(52) U.S. Cl.
CPC .......... *A61N 1/3629* (2017.08); *A61F 2/2418* (2013.01); *A61N 1/057* (2013.01); (Continued)

(58) Field of Classification Search
CPC .... A61N 1/3629; A61N 1/057; A61N 1/3787; A61N 1/37229; A61N 1/36507; A61F 2/2418; A61F 2230/0065; A61B 5/28
See application file for complete search history.

(56) References Cited

U.S. PATENT DOCUMENTS 4,256,094 A 3/1981 Kapp et al.
4,979,955 A 12/1990 Smith
(Continued)

FOREIGN PATENT DOCUMENTS

EP 3508113 7/2019
FR 3034650 10/2016
(Continued)

OTHER PUBLICATIONS

U.S. Appl. No. 16/868,121, filed May 6, 2020, published as 2020/0261224, issued as U.S. Pat. No. 11,013,597.
(Continued)

*Primary Examiner* — Todd J Scherbel
*Assistant Examiner* — Mikail A Mannan
(74) *Attorney, Agent, or Firm* — Sughrue Mion, PLLC

(57) ABSTRACT

A prosthetic aortic valve is provided, which is configured to be delivered to a native aortic valve of a patient in a constrained delivery configuration within a delivery sheath. The prosthetic aortic valve includes a frame, which includes interconnected stent struts arranged so as to define interconnected stent cells; a plurality of prosthetic leaflets coupled to the frame; a cathode and an anode, which are mechanically coupled to the frame; and a prosthetic-valve coil, which is in non-wireless electrical communication with the cathode and the anode, and is coupled to a plurality of the stent struts, running along the stent struts so as to surround a plurality of the stent cells when the prosthetic aortic valve is in an expanded fully-deployed configuration upon release from the delivery sheath. Other embodiments are also described.

26 Claims, 24 Drawing Sheets

Related U.S. Application Data which is a continuation-in-part of application No. 16/734,798, filed on Jan. 6, 2020, now Pat. No. 10,835,750, which is a continuation-in-part of application No. 15/864,661, filed on Jan. 8, 2018, now Pat. No. 10,543,083, application No. 17/328,588, filed on May 24, 2021, which is a continuation-in-part of application No. PCT/IL2021/050017, filed on Jan. 6, 2021, and a continuation-in-part of application No. PCT/IL2021/050016, filed on Jan. 6, 2021, and a continuation-in-part of application No. 17/142,729, filed on Jan. 6, 2021, now Pat. No. 11,065,451.

(51) Int. Cl.
  *A61N 1/05* (2006.01)
  *A61N 1/372* (2006.01)
  *A61N 1/378* (2006.01)

(52) U.S. Cl.
  CPC ......... *A61N 1/3727* (2013.01); *A61N 1/3787* (2013.01); *A61N 1/37229* (2013.01); *A61F 2210/0014* (2013.01)

(56) References Cited

U.S. PATENT DOCUMENTS

| | | |
|---|---|---|
| 5,487,760 A | 1/1996 | Villafana |
| 6,030,335 A | 2/2000 | Franchi |
| 6,030,336 A | 2/2000 | Franchi |
| 6,050,932 A | 4/2000 | Franchi |
| 7,643,879 B2 | 1/2010 | Shuros et al. |
| 7,914,569 B2 | 3/2011 | Nguyen et al. |
| 8,092,365 B2 | 1/2012 | Rinderknecht et al. |
| 8,239,023 B2 | 8/2012 | Shuros et al. |
| 9,005,106 B2 | 4/2015 | Gross et al. |
| 9,326,854 B2 | 5/2016 | Casley et al. |
| 9,526,637 B2 | 12/2016 | Dagan et al. |
| 9,662,211 B2 | 5/2017 | Hodson et al. |
| 9,737,264 B2 | 8/2017 | Braido et al. |
| 9,808,201 B2 | 11/2017 | Braido et al. |
| 10,543,083 B2 | 1/2020 | Gross |
| 10,758,725 B2 | 9/2020 | Daniels et al. |
| 10,835,750 B2 | 11/2020 | Gross |
| 11,013,597 B2 | 5/2021 | Gross |
| 2003/0032853 A1 | 2/2003 | Korakianitis et al. |
| 2004/0024285 A1 | 2/2004 | Muckter |
| 2004/0097784 A1 | 5/2004 | Peters et al. |
| 2004/0111006 A1 | 6/2004 | Alferness et al. |
| 2005/0049696 A1 | 3/2005 | Siess et al. |
| 2006/0206170 A1* | 9/2006 | Denker ................. H01Q 21/24 607/60 |
| 2008/0077016 A1 | 3/2008 | Sparks et al. |
| 2010/0197994 A1 | 8/2010 | Mehmanesh |
| 2011/0071351 A1 | 3/2011 | Sperling |
| 2011/0137370 A1 | 6/2011 | Gross et al. |
| 2011/0196482 A1 | 8/2011 | Forsell |
| 2012/0245678 A1 | 9/2012 | Solem |
| 2012/0265296 A1 | 10/2012 | McNamara et al. |
| 2012/0296382 A1 | 11/2012 | Shuros et al. |
| 2013/0138205 A1 | 5/2013 | Kushwaha et al. |
| 2013/0297009 A1 | 11/2013 | Chalekian et al. |
| 2014/0066895 A1 | 3/2014 | Kipperman |
| 2014/0081154 A1 | 3/2014 | Toth |
| 2014/0180391 A1 | 6/2014 | Dagan et al. |
| 2014/0275720 A1 | 9/2014 | Ferrari |
| 2015/0128684 A1 | 5/2015 | Hodson et al. |
| 2016/0045165 A1 | 2/2016 | Braido et al. |
| 2016/0045316 A1* | 2/2016 | Braido ................. A61B 5/0215 623/2.38 |
| 2016/0144091 A1 | 5/2016 | Breedon et al. |
| 2016/0278951 A1 | 9/2016 | Dagan et al. |
| 2017/0100527 A1 | 4/2017 | Schwammenthal et al. |
| 2017/0258585 A1 | 9/2017 | Marquez et al. |
| 2017/0266433 A1 | 9/2017 | Daniels et al. |
| 2019/0076588 A1 | 3/2019 | Ochsner et al. |
| 2019/0209302 A1 | 7/2019 | Gross |
| 2020/0139121 A1 | 5/2020 | Gross |
| 2020/0261224 A1 | 8/2020 | Gross |
| 2020/0282204 A1 | 9/2020 | Capek et al. |

FOREIGN PATENT DOCUMENTS

| | | |
|---|---|---|
| WO | 2013/035092 | 3/2013 |
| WO | 2014/043235 | 3/2014 |
| WO | 2016/157183 | 10/2016 |

OTHER PUBLICATIONS

U.S. Appl. No. 16/734,798, filed Jan. 6, 2020, published as 2020/0139121, issued as U.S. Pat. No. 10,835,750.
U.S. Appl. No. 15/864,661, filed Jan. 8, 2018, published as 2019/0209302, issued as U.S. Pat. No. 10,543,083.
U.S. Appl. No. 17/142,729, filed Jan. 6, 2021.
"Pacing at the Bundle of His," Medtronic, Inc., Minneapolis, MN, USA (Oct. 2017).
"Medtronic EvolutTM Pro System brochure," Medtronic, Inc., Minneapolis, MN, USA (Mar. 2017).
"Medtronic CoreValveTM System Instructions for Use," Medtronic, Inc., Minneapolis, MN, USA (2014).
An Office Action dated Apr. 11, 2019, which issued during the prosecution of U.S. Appl. No. 15/864,661.
European Search Report dated May 17, 2019 which issued during the prosecution of Applicant's European App No. 19150581.7.
Jobanputra Y et al., "Rapid Ventricular Pacing During Transcatheter Valve Procedures Using an Internal Device and Programmer: A Demonstration of Feasibility," JACC Mar. 20, 2018, vol. 71, Issue 11, p. 1381.
An Office Action dated Apr. 27, 2020, which issued during the prosecution of U.S. Appl. No. 16/734,798.
Notice of Allowance dated Aug. 3, 2020, which issued during the prosecution of U.S. Appl. No. 16/734,798.
Notice of Allowance dated Jan. 25, 2021, which issued during the prosecution of U.S. Appl. No. 16/868,121.
An Office Action dated Nov. 23, 2020, which issued during the prosecution of U.S. Appl. No. 16/868,121.
Notice of Allowance dated Sep. 26, 2019, which issued during the prosecution of U.S. Appl. No. 15/864,661.
Notice of Allowance dated Mar. 22, 2021, which issued during the prosecution of U.S. Appl. No. 17/142,729.

* cited by examiner

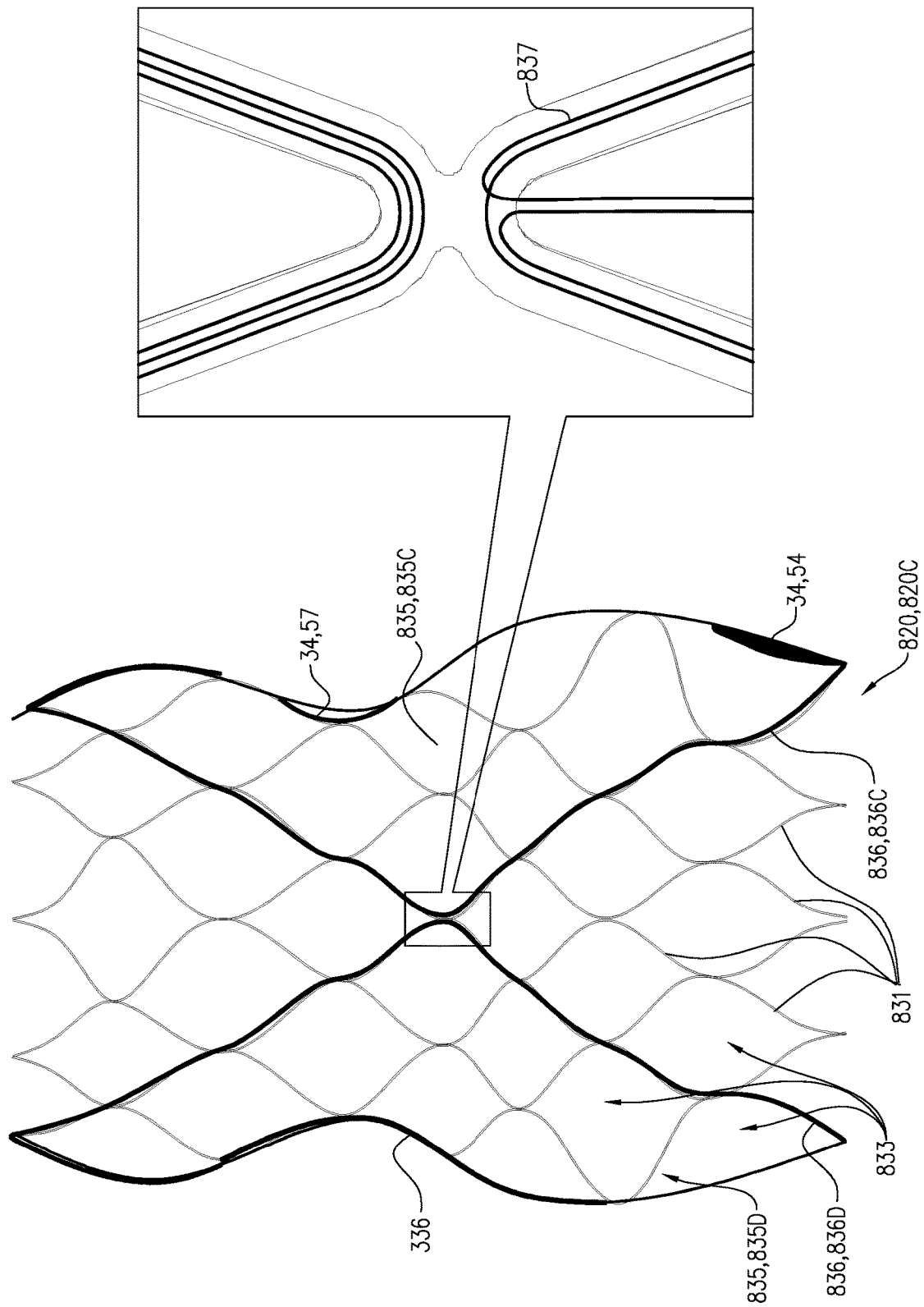

PROSTHETIC AORTIC VALVE PACING SYSTEM

CROSS-REFERENCE TO RELATED APPLICATIONS

The present application:

(i) is a continuation-in-part of U.S. application Ser. No. 16/868,121, filed May 6, 2020, now U.S. Pat. No. 11,013,597, which is a continuation-in-part of U.S. application Ser. No. 16/734,798, filed Jan. 6, 2020, now U.S. Pat. No. 10,835,750, which (a) is a continuation-in-part of U.S. application Ser. No. 15/864,661, filed Jan. 8, 2018, now U.S. Pat. No. 10,543,083, and (b) claims foreign priority to European Application 19150581.7, filed Jan. 7, 2019, which published as EP 3 508 113 A1;

(ii) is a continuation-in-part of International Application PCT/IL2021/050017, filed Jan. 6, 2021;

(iii) is a continuation-in-part of International Application PCT/IL2021/050016, filed Jan. 6, 2021; and (iv) is a continuation-in-part of U.S. application Ser. No. 17/142,729, filed Jan. 6, 2021, now U.S. Pat. No. 11,065,451.

All of the above-referenced applications are assigned to the assignee of the present application and incorporated herein by reference.

(The above-mentioned European Application 19150581.7 claims foreign priority to the above-mentioned U.S. application Ser. No. 15/864,661.)

FIELD OF THE APPLICATION

The present invention relates generally to surgical implants and systems, and specifically to prosthetic aortic valves and systems.

BACKGROUND OF THE APPLICATION

Aortic heart valve replacement may be necessary to treat valve regurgitation or stenotic calcification of the leaflets. In percutaneous transluminal delivery techniques, a prosthetic aortic valve is compressed for delivery in a catheter and advanced through the descending aorta to the heart, where the prosthetic valve is deployed in the aortic valve annulus. New-onset cardiac conduction disturbances are common after transcatheter aortic valve implantation (TAVI). The most common complication is left bundle branch block (LBBB).

U.S. Pat. No. 7,914,569 to Nguyen et al., which is incorporated herein by reference, describes a heart valve prosthesis having a self-expanding multi-level frame that supports a valve body comprising a skirt and plurality of coapting leaflets. The frame transitions between a contracted delivery configuration that enables percutaneous transluminal delivery, and an expanded deployed configuration having an asymmetric hourglass shape. The valve body skirt and leaflets are constructed so that the center of coaptation may be selected to reduce horizontal forces applied to the commissures of the valve, and to efficiently distribute and transmit forces along the leaflets and to the frame. Alternatively, the valve body may be used as a surgically implantable replacement valve prosthesis.

SUMMARY OF THE APPLICATION

Some embodiments of the present invention provide a valve prosthesis system, which comprises a prosthetic aortic valve, which is configured to be implanted in a native aortic valve of a patient, and which comprises a plurality of prosthetic leaflets, a frame, and one or more electrodes, including a cathode and an anode, mechanically coupled to the frame. The prosthetic aortic valve further comprises a prosthetic-valve coil, which is in non-wireless electrical communication with the cathode and the anode. Typically, the prosthetic aortic valve does not comprise any active electronic components.

In some applications, the valve prosthesis system further comprises a non-implantable unit, which comprises an energy-transmission coil; at least two sensing skin ECG electrodes; and non-implantable control circuitry. The non-implantable control circuitry is configured to:

drive the cathode and the anode to apply a pacing signal to a heart of the patient, detect at least one cardiac parameter using the at least two sensing skin ECG electrodes, and at least partially responsively to the detected at least one cardiac parameter, set parameters of the pacing signal, by wirelessly transferring energy from the energy-transmission coil to the prosthetic-valve coil by inductive coupling.

For some applications, the frame is shaped so as to define an upstream inflow portion; a downstream outflow portion; and a constriction portion, which is axially between the upstream inflow portion and the downstream outflow portion. The prosthetic leaflets are coupled to the constriction portion.

For some applications, when the prosthetic aortic valve is in an expanded fully-deployed configuration: free edges of the prosthetic leaflets face toward the downstream outflow portion, and a ring-shaped longitudinal border between the downstream outflow portion and the constriction portion is defined by a downstream-most point of the frame to which the prosthetic leaflets are coupled. The prosthetic aortic valve further comprises a prosthetic-valve coil, which is in non-wireless electrical communication with the one or more electrodes, and which is coupled to the frame no more than 1 mm upstream of the ring-shaped longitudinal border, such as axially along the downstream outflow portion.

In some embodiments of the present invention, a valve prosthesis system is provided, which includes a prosthetic aortic valve and a non-implantable unit. The prosthetic aortic valve which includes a plurality of prosthetic leaflets; a frame; a cathode and an anode, which are mechanically coupled to the frame; and a prosthetic-valve coil, which is in non-wireless electrical communication with the cathode and the anode. The non-implantable unit includes an energy-transmission coil; and non-implantable control circuitry, which is configured to drive the cathode and the anode to apply a pacing signal and to set parameters of the pacing signal, by wirelessly transferring energy from the energy-transmission coil to the prosthetic-valve coil by inductive coupling.

Some embodiments of the present invention provide a prosthetic aortic valve, which is configured to be delivered to a native aortic valve of a patient in a constrained delivery configuration within a delivery sheath. The prosthetic aortic valve comprises a frame; a plurality of prosthetic leaflets coupled to the frame; a cathode and an anode, which are mechanically coupled to the frame; and a prosthetic-valve coil, which is coupled to the frame and is in non-wireless electrical communication with the cathode and the anode. When the prosthetic aortic valve is in an expanded fully-deployed configuration upon release from the delivery sheath, (a) a line defined between upstream-most and downstream-most points of mechanical coupling between the prosthetic-valve coil and the frame and (b) a central longitudinal axis defined by the frame form an angle of between 20 and 70 degrees, such as between 30 and 60 degrees, e.g., between 40 and 50 degrees, such as 45 degrees.

For some applications, a valve prosthesis system is provided that comprises the prosthetic aortic valve and an external unit. The external unit is configured to be disposed outside a body of the patient and comprises (a) an energy-transmission coil, and (b) external-unit control circuitry, which is configured to drive the energy-transmission coil to wirelessly transfer energy, by inductive coupling, to the prosthetic-valve coil when the prosthetic aortic valve is in the expanded fully-deployed configuration.

For some of these applications, the energy-transmission coil is configured to be positioned against the patient's chest, typically over a sternum. This positioning of the energy-transmission coil provides high transmission efficiency, because the respective axes of the energy-transmission coil and the prosthetic-valve coil are generally aligned, because of the angle formed between the prosthetic-valve coil and the central longitudinal axis of the frame described hereinabove. This high transmission efficiency may allow the prosthetic-valve coil and/or the energy-transmission coil to include fewer turns of the coil(s) and/or to have smaller diameters. Alternatively or additionally, this high transmission efficiency may allow the external unit to use less power to induce the same amount of current in the prosthetic-valve coil.

For other applications, the energy-transmission coil is configured to be positioned around the patient's neck. This positioning of the energy-transmission coil provides high transmission efficiency, because the respective axes of the energy-transmission coil and the prosthetic-valve coil are generally aligned, because of the angle formed between the prosthetic-valve coil and the central longitudinal axis of the frame described hereinabove.

For some applications, when the prosthetic aortic valve is in the expanded fully-deployed configuration, (a) the downstream-most point of mechanical coupling between the prosthetic-valve coil and the frame and (b) a centroid of the cathode are rotationally aligned with each other or rotationally offset from each other about the central longitudinal axis of the frame by less than 50 degrees, such as less than 30 degrees. Because of this rotational alignment, aligning the cathode adjacent to cardiac tissue near the bundle of His (facing generally posteriorly) automatically aligns the prosthetic-valve coil facing generally in the opposite direction, facing generally anterio-superiorly toward the sternum. This orientation provides good wireless coupling with the energy-transmission coil.

In some applications of the present invention, the frame of the prosthetic aortic valve comprises interconnected stent struts arranged so as to define interconnected stent cells. The prosthetic-valve coil is coupled to a plurality of the stent struts, running along the stent struts so as to surround a plurality of the stent cells when the prosthetic aortic valve is in an expanded fully-deployed configuration upon release from the delivery sheath. The stent struts are shaped so as to allowing efficient crimping (compression) of the frame when in the constrained delivery configuration within the delivery sheath. The coupling of the prosthetic-valve coil to the stent struts, running along the stent struts, causes the prosthetic-valve coil to be crimped efficiently together with the frame.

There is therefore provided, in accordance with an Inventive Concept 1 of the present invention, a method of assembling an electronic prosthetic aortic valve, the method including:
inserting an electronics component into a valve component, the electronics component including one or more electrodes and a prosthetic-valve coil, and the valve component including a frame and prosthetic leaflets coupled to the frame; and
coupling the electronics component to the valve component.

Inventive Concept 2. The method according to Inventive Concept 1, wherein coupling the electronics component to the valve component includes:
coupling a first portion of the electronics component to an inner surface of the frame; and
coupling a second portion of the electronics component to an external surface of the frame.

Inventive Concept 3. The method according to Inventive Concept 2,
wherein the first portion of the electronics component includes the prosthetic-valve coil and one of the one or more electrodes, and
wherein the second portion of the electronics component includes a cathode of the one or more electrodes.

Inventive Concept 4. The method according to Inventive Concept 3, wherein the electronics component further includes prosthetic-aortic-valve control circuitry, and wherein the first portion of the electronic component includes the prosthetic-aortic-valve control circuitry.

Inventive Concept 5. The method according to Inventive Concept 4,
wherein the electronics component further includes an elongate insulated electrical conductor that electrically couples the cathode to the prosthetic-aortic-valve control circuitry, and
wherein coupling the electronics component to the valve component includes coupling the electronics component to the valve component such that the conductor passes from inside to outside the frame.

Inventive Concept 6. The method according to Inventive Concept 5, wherein the valve component further includes a skirt, and wherein coupling the electronics component to the valve component includes coupling the electronics component to the valve component such that the conductor passes from inside to outside the frame through the skirt.

Inventive Concept 7. The method according to any one of Inventive Concepts 1-6, wherein coupling the electronics component to the valve component includes stitching the electronics component to the valve component.

Inventive Concept 8. The method according to Inventive Concept 7, wherein the valve component further includes a skirt, and wherein coupling the electronics component to the valve component includes stitching the electronics component to the skirt.

Inventive Concept 9. The method according to any one of Inventive Concepts 1-8,
wherein the frame is shaped so as to define: (1) an upstream inflow portion, (2) a downstream outflow portion, and (3) a constriction portion, which is axially between the upstream inflow portion and the downstream outflow portion, wherein the prosthetic leaflets are coupled to the constriction portion, and wherein the prosthetic aortic valve is configured such that when in an expanded configuration: (A) free edges of the prosthetic leaflets face toward the downstream outflow portion, and (B) a ring-shaped longitudinal border between the downstream outflow portion and the constriction portion is defined by a downstream-most point of the frame to which the prosthetic leaflets are coupled, wherein the prosthetic-valve coil is in non-wireless electrical communication with the one or more electrodes, and wherein coupling the electronics component to the valve component comprises coupling the electronics component to the valve component such that the prosthetic-valve coil is coupled to the frame no more than 1 mm upstream of the ring-shaped longitudinal border.

Inventive Concept 10. The method according to Inventive Concept 9, wherein coupling the electronics component to the valve component comprises coupling the electronics component to the valve component such that the prosthetic-valve coil is disposed axially along the downstream outflow portion.

Inventive Concept 11. The method according to Inventive Concept 9, wherein coupling the electronics component to the valve component comprises coupling the electronics component to the valve component such that at least one of the one or more electrodes is coupled to the upstream inflow portion of the frame.

Inventive Concept 12. The method according to Inventive Concept 11, wherein the prosthetic aortic valve is configured such that when the prosthetic aortic valve is in the expanded configuration the frame has an inflow end at the upstream inflow portion and a downstream outflow end at the downstream outflow portion, and an axial length, measured between the inflow end and the downstream outflow end, and wherein coupling the electronics component to the valve component comprises coupling the electronics component to the valve component such that at least one of the one or more electrodes is coupled to the upstream inflow portion within a distance from the inflow end, the distance equal to 10% of the axial length of the frame.

There is further provided, in accordance with an Inventive Concept 13 of the present invention, apparatus including a prosthetic aortic valve, which includes:

(a) a plurality of prosthetic leaflets;
(b) a frame, which is shaped so as to define:
(1) an upstream inflow portion,
(2) a downstream outflow portion, and
(3) a constriction portion, which is axially between the upstream inflow portion and the downstream outflow portion, wherein the prosthetic leaflets are coupled to the constriction portion, and wherein when the prosthetic aortic valve is in an expanded fully-deployed configuration: (A) free edges of the prosthetic leaflets face toward the downstream outflow portion, and (B) a ring-shaped longitudinal border between the downstream outflow portion and the constriction portion is defined by a downstream-most point of the frame to which the prosthetic leaflets are coupled;
(c) one or more electrodes coupled to the frame; and
(d) a prosthetic-valve coil, which is in non-wireless electrical communication with the one or more electrodes, and which is coupled to the frame no more than 1 mm upstream of the ring-shaped longitudinal border.

Inventive Concept 14. The apparatus according to Inventive Concept 13, wherein the prosthetic-valve coil is disposed axially along the downstream outflow portion.

Inventive Concept 15. The apparatus according to Inventive Concept 13, wherein at least one of the one or more electrodes is coupled to the upstream inflow portion of the frame.

Inventive Concept 16. The apparatus according to Inventive Concept 15, wherein when the prosthetic aortic valve is in the expanded fully-deployed configuration:

the frame has an inflow end at the upstream inflow portion and a downstream outflow end at the downstream outflow portion, and an axial length, measured between the inflow end and the downstream outflow end, and at least one of the one or more electrodes is coupled to the upstream inflow portion within a distance from the inflow end, the distance equal to 10% of the axial length of the frame.

Inventive Concept 17. A valve prosthesis system comprising the prosthetic aortic valve according to Inventive Concept 13, the valve prosthesis system further including an external unit, which includes:

an external-unit coil; and external-unit control circuitry, which is configured to drive the external-unit coil to wirelessly transfer energy, by inductive coupling, to the prosthetic-valve coil when the prosthetic aortic valve is in the expanded fully-deployed configuration.

Inventive Concept 18. The valve prosthesis system according to Inventive Concept 17, wherein the external-unit control circuitry is configured to drive the one or more electrodes to apply a pacing signal.

Inventive Concept 19. The valve prosthesis system according to Inventive Concept 17, wherein the external unit includes a collar configured to be worn around a patient's neck, and the external-unit coil is incorporated into the collar.

Inventive Concept 20. The valve prosthesis system according to Inventive Concept 13, wherein the prosthetic aortic valve further includes prosthetic-aortic-valve control circuitry, which is coupled to the frame and which is in non-wireless electrical communication with the one or more electrodes, and wherein the prosthetic-valve coil is in non-wireless electrical communication with the prosthetic-aortic-valve control circuitry, such that the prosthetic-valve coil is in non-wireless electrical communication with the one or more electrodes via the prosthetic-aortic-valve control circuitry.

Inventive Concept 21. The valve prosthesis system according to Inventive Concept 20, wherein the prosthetic-aortic-valve control circuitry is configured to apply pacing.

Inventive Concept 22. The valve prosthesis system according to Inventive Concept 20, wherein the one or more electrodes include a cathode that is coupled to the upstream inflow portion of the frame, and wherein the prosthetic-aortic-valve control circuitry is configured to drive the cathode to apply a cathodic current.

Inventive Concept 23. The valve prosthesis system according to Inventive Concept 22, wherein the prosthetic aortic valve further includes a skirt coupled to an external surface of the upstream inflow portion of the frame, and wherein the cathode is disposed on an external surface of the skirt.

Inventive Concept 24. The valve prosthesis system according to Inventive Concept 20, wherein the prosthetic leaflets are coupled to the frame at at least first and second commissures that are located at respective first and second angular locations around the frame separated by a first angular offset around the frame when the prosthetic aortic valve is in the expanded fully-deployed configuration, and wherein the prosthetic-aortic-valve control circuitry is coupled to the frame at a third angular location around the frame that is separated from the first angular location by a second angular offset that equals between 40% and 60% of the first angular offset when the prosthetic aortic valve is in the expanded fully-deployed configuration.

Inventive Concept 25. The valve prosthesis system according to Inventive Concept 20, wherein the prosthetic-aortic-valve control circuitry is coupled to the frame inside the frame.

Inventive Concept 26. The valve prosthesis system according to Inventive Concept 20, wherein the prosthetic-aortic-valve control circuitry is stitched to the frame.

Inventive Concept 27. The valve prosthesis system according to Inventive Concept 20, wherein the prosthetic aortic valve further includes a skirt coupled to an external surface of the upstream inflow portion of the frame, and wherein the prosthetic-aortic-valve control circuitry is stitched to the skirt.

Inventive Concept 28. The valve prosthesis system according to Inventive Concept 20, wherein the prosthetic-aortic-valve control circuitry is configured to (a) use the one or more electrodes to sense a cardiac signal, and (b) drive the prosthetic-valve coil to transmit a wireless signal indicative of the sensed cardiac signal.

Inventive Concept 29. The valve prosthesis system according to Inventive Concept 20, wherein the prosthetic aortic valve includes an electronic implant, which includes:
 the prosthetic-aortic-valve control circuitry; and
 a multi-layer protective coating, which includes the following layers in the following order:
  a first inner aluminum oxide (AlOx) film layer deposited on the circuitry; and
  a second parylene layer deposited on the first inner AlOx film layer, wherein the prosthetic-aortic-valve control circuitry is not encased in a case.

There is still further provided, in accordance with an Inventive Concept 30 of the present invention, apparatus including an electronic implant, which includes:
 circuitry; and
 a multi-layer protective coating, which includes the following layers in the following order:
  a first inner aluminum oxide (AlOx) film layer deposited on the circuitry; and
  a second parylene layer deposited on the first inner AlOx film layer, wherein the circuitry is not encased in a case.

Inventive Concept 31. The apparatus according to Inventive Concept 30, wherein the multi-layer protective coating further includes a third layer disposed on the second parylene layer, the third layer having a thickness of between 100 and 200 microns, and configured to provide mechanical protection for the circuitry.

Inventive Concept 32. The apparatus according to Inventive Concept 31, wherein the third layer includes a material selected from the group consisting of: silicone and PTFE.

Inventive Concept 33. The apparatus according to Inventive Concept 31, wherein the third layer is cast onto the second parylene layer.

Inventive Concept 34. The apparatus according to Inventive Concept 31, wherein the multi-layer protective coating further includes a fourth outer parylene layer deposited on the third layer.

Inventive Concept 35. The apparatus according to Inventive Concept 30, further including a prosthetic aortic valve, which includes:
 a frame;
 a plurality of prosthetic leaflets coupled to the frame;
 one or more electrodes coupled to the frame; and
 a prosthetic-valve coil coupled to the frame,
 wherein the electronic implant is coupled to the frame and is in non-wireless electrical communication with the one or more electrodes, and
 wherein the prosthetic-valve coil is in non-wireless electrical communication with the circuitry, such that the prosthetic-valve coil is in non-wireless electrical communication with the one or more electrodes via the circuitry.

There is additionally provided, in accordance with an Inventive Concept 36 of the present invention, a method of manufacturing an electronic implant, the method including:
 depositing a first inner aluminum oxide (AlOx) film layer on circuitry of the electronic implant; and
 depositing a second parylene layer on the first inner AlOx film layer, so as to form a multi-layer protective coating with the first inner AlOx film layer,
 wherein manufacturing the electronic implant does not include encasing the circuitry in a case.

Inventive Concept 37. The method according to Inventive Concept 36, further including disposing a third layer on the second parylene layer, the third layer having a thickness of between 100 and 200 microns, and configured to provide mechanical protection for the circuitry.

Inventive Concept 38. The method according to Inventive Concept 37, wherein the third layer includes a material selected from the group consisting of: silicone and PTFE.

Inventive Concept 39. The method according to Inventive Concept 37, wherein disposing the third layer includes casting the third layer onto the second parylene layer.

Inventive Concept 40. The method according to Inventive Concept 37, further including depositing a fourth outer parylene layer on the third layer.

There is yet additionally provided, in accordance with an Inventive Concept 41 of the present invention, apparatus including a prosthetic aortic valve, which includes:
 (a) a plurality of prosthetic leaflets;
 (b) a frame, which is shaped so as to define:
  (1) an upstream inflow portion,
  (2) a downstream outflow portion, and
  (3) a constriction portion, which is axially between the upstream inflow portion and the downstream outflow portion, wherein the prosthetic leaflets are coupled to the constriction portion, and wherein when the prosthetic aortic valve is in an expanded fully-deployed configuration: (A) free edges of the prosthetic leaflets face toward the downstream outflow portion, and (B) a ring-shaped longitudinal border between the downstream outflow portion and the constriction portion is defined by a downstream-most point of the frame to which the prosthetic leaflets are coupled;
 (c) one or more electrodes coupled to the upstream inflow portion of the frame; and
 (d) a prosthetic-valve coil, which is in non-wireless electrical communication with the one or more electrodes.

Inventive Concept 42. The apparatus according to Inventive Concept 41, wherein when the prosthetic aortic valve is in the expanded fully-deployed configuration:
 the frame has an inflow end at the upstream inflow portion and a downstream outflow end at the downstream outflow portion, and an axial length, measured between the inflow end and the downstream outflow end, and
 at least one of the one or more electrodes is coupled to the upstream inflow portion within a distance from the inflow end, the distance equal to 10% of the axial length of the frame.

Inventive Concept 43. The apparatus according to Inventive Concept 41, wherein the prosthetic aortic valve further includes prosthetic-aortic-valve control circuitry, which is coupled to the frame and which is in non-wireless electrical communication with the one or more electrodes, and wherein the prosthetic-valve coil is in non-wireless electrical communication with the prosthetic-aortic-valve control circuitry, such that the prosthetic-valve coil is in non-wireless electrical communication with the one or more electrodes via the prosthetic-aortic-valve control circuitry.

Inventive Concept 44. The apparatus according to Inventive Concept 43, wherein the prosthetic-aortic-valve control circuitry is configured to apply pacing.

Inventive Concept 45. The apparatus according to Inventive Concept 43, wherein the one or more electrodes include a cathode that is coupled to the upstream inflow portion of the frame, and wherein the prosthetic-aortic-valve control circuitry is configured to drive the cathode to apply a cathodic current.

Inventive Concept 46. The apparatus according to Inventive Concept 45, wherein the prosthetic aortic valve further includes a skirt coupled to an external surface of the upstream inflow portion of the frame, and wherein the cathode is disposed on an external surface of the skirt.

There is also provided, in accordance with an Inventive Concept 47 of the present invention, a method of assembling an electronic prosthetic aortic valve, the method including:

inserting an electronics component into a valve component, the electronics component including one or more electrodes and a prosthetic-valve coil, and the valve component including a frame and prosthetic leaflets coupled to the frame; and coupling the electronics component to the valve component.

Inventive Concept 48. The method according to Inventive Concept 47, wherein coupling the electronics component to the valve component includes:

coupling a first portion of the electronics component to an inner surface of the frame; and coupling a second portion of the electronics component to an external surface of the frame.

Inventive Concept 49. The method according to Inventive Concept 48, wherein the first portion of the electronics component includes the prosthetic-valve coil and one of the one or more electrodes, and wherein the second portion of the electronics component includes a cathode of the one or more electrodes.

Inventive Concept 50. The method according to Inventive Concept 49, wherein the electronics component further includes prosthetic-aortic-valve control circuitry, and wherein the first portion of the electronic component includes the prosthetic-aortic-valve control circuitry.

Inventive Concept 51. The method according to Inventive Concept 50, wherein the electronics component further includes an elongate insulated electrical conductor that electrically couples the cathode to the prosthetic-aortic-valve control circuitry, and wherein coupling the electronics component to the valve component includes coupling the electronics component to the valve component such that the conductor passes from inside to outside the frame.

Inventive Concept 52. The method according to Inventive Concept 51, wherein the valve component further includes a skirt, and wherein coupling the electronics component to the valve component includes coupling the electronics component to the valve component such that the conductor passes from inside to outside the frame through the skirt.

Inventive Concept 53. The method according to Inventive Concept 47, wherein coupling the electronics component to the valve component includes stitching the electronics component to the valve component.

Inventive Concept 54. The method according to Inventive Concept 47, wherein the valve component further includes a skirt, and wherein coupling the electronics component to the valve component includes stitching the electronics component to the skirt.

There is further provided, in accordance with an Inventive Concept 55 of the present invention, apparatus including a valve prosthesis system including:

(a) a delivery system, which includes:

a delivery tube;

a delivery-system coil, which is coupled to the delivery tube at a distal site of the delivery tube;

one or more wires, which pass along the delivery tube; and delivery-system control circuitry, which is in electrical communication with the delivery-system coil via the one or more wires; and (b) a prosthetic aortic valve, which includes:

a frame;

a plurality of prosthetic leaflets coupled to the frame;

one or more electrodes coupled to the frame; and a prosthetic-valve coil coupled to the frame and in non-wireless electrical communication with the one or more electrodes, wherein the prosthetic aortic valve is (i) removably disposable in the delivery tube in a compressed delivery configuration and (ii) configured to assume:

(A) a partially-expanded partially-deployed configuration upon being partially released from a distal end of the delivery tube such that (1) at least one of the one or more electrodes is positioned outside the delivery tube, and (2) the prosthetic-valve coil is compressed within the delivery tube, and (B) an expanded fully-deployed configuration upon being fully released from the distal end of the delivery tube, and wherein the delivery-system control circuitry is configured to drive the delivery-system coil to wirelessly transfer energy, by inductive coupling, to the prosthetic-valve coil at least when the prosthetic aortic valve is in the partially-deployed configuration.

Inventive Concept 56. The apparatus according to Inventive Concept 55, the valve prosthesis system further includes an external unit, which includes:

an external-unit coil; and external-unit control circuitry, which is configured to drive the external-unit coil to wirelessly transfer energy, by inductive coupling, to the prosthetic-valve coil when the prosthetic aortic valve is in the expanded fully-deployed configuration.

Inventive Concept 57. The apparatus according to Inventive Concept 56, wherein the external-unit control circuitry is configured to begin driving the external-unit coil to wirelessly transfer the energy only after the prosthetic aortic valve is in the expanded fully-deployed configuration.

Inventive Concept 58. The apparatus according to Inventive Concept 55, wherein the delivery-system control circuitry is configured to cease driving the delivery-system coil to wirelessly transfer the energy when the prosthetic aortic valve assumes the expanded fully-deployed configuration upon being fully released from the distal end of the delivery tube.

Inventive Concept 59. The apparatus according to Inventive Concept 55,
wherein the frame is shaped so as to define:
an upstream inflow portion,
a downstream outflow portion, and
a constriction portion, which is axially between the upstream inflow portion and the downstream outflow portion, wherein the prosthetic leaflets are coupled to the constriction portion such that free edges of the prosthetic leaflets face toward the downstream outflow portion when the prosthetic aortic valve is in the expanded fully-deployed configuration, and
wherein the prosthetic-valve coil is disposed axially along the downstream outflow portion.

Inventive Concept 60. The apparatus according to Inventive Concept 59, wherein the prosthetic-valve coil is not disposed axially along the constriction portion and is not disposed axially along the upstream inflow portion.

Inventive Concept 61. The apparatus according to Inventive Concept 59, wherein at least one of the one or more electrodes is coupled to the upstream inflow portion of the frame.

Inventive Concept 62. The apparatus according to Inventive Concept 61, wherein when the prosthetic aortic valve is in the expanded fully-deployed configuration:
the frame has an inflow end at the upstream inflow portion and a downstream outflow end at the downstream outflow portion, and an axial length, measured between the inflow end and the downstream outflow end, and
at least one of the one or more electrodes is coupled to the upstream inflow portion within a distance from the inflow end, the distance equal to 10% of the axial length of the frame.

Inventive Concept 63. The apparatus according to Inventive Concept 55,
wherein the prosthetic aortic valve further includes prosthetic-aortic-valve control circuitry, which is coupled to the frame and which is in non-wireless electrical communication with the one or more electrodes, and
wherein the prosthetic-valve coil is in non-wireless electrical communication with the prosthetic-aortic-valve control circuitry, such that the prosthetic-valve coil is in non-wireless electrical communication with the one or more electrodes via the prosthetic-aortic-valve control circuitry.

Inventive Concept 64. The apparatus according to Inventive Concept 63,
wherein the frame is shaped so as to define:
an upstream inflow portion,
a downstream outflow portion, and
a constriction portion, which is axially between the upstream inflow portion and the downstream outflow portion, wherein the prosthetic leaflets are coupled to the constriction portion such that free edges of the prosthetic leaflets face toward the downstream outflow portion when the prosthetic aortic valve is in the expanded fully-deployed configuration,
wherein the one or more electrodes include a cathode that is coupled to the upstream inflow portion of the frame, and
wherein the prosthetic-aortic-valve control circuitry is configured to drive the cathode to apply a cathodic current.

Inventive Concept 65. The apparatus according to Inventive Concept 64, wherein the prosthetic aortic valve further includes a skirt coupled to an external surface of the upstream inflow portion of the frame, and wherein the cathode is disposed on an external surface of the skirt.

Inventive Concept 66. The apparatus according to Inventive Concept 63,
wherein the prosthetic leaflets are coupled to the frame at at least first and second commissures that are located at respective first and second angular locations around the frame separated by a first angular offset around the frame when the prosthetic aortic valve is in the expanded fully-deployed configuration, and
wherein the prosthetic-aortic-valve control circuitry is coupled to the frame at a third angular location around the frame that is separated from the first angular location by a second angular offset that equals between 40% and 60% of the first angular offset when the prosthetic aortic valve is in the expanded fully-deployed configuration.

Inventive Concept 67. The apparatus according to Inventive Concept 63, wherein the prosthetic-aortic-valve control circuitry is coupled to the frame inside the frame.

Inventive Concept 68. The apparatus according to Inventive Concept 63, wherein the prosthetic-aortic-valve control circuitry is configured to (a) use the one or more electrodes to sense a cardiac signal, and (b) drive the prosthetic-valve coil to transmit a wireless signal indicative of the sensed cardiac signal.

Inventive Concept 69. The apparatus according to Inventive Concept 63, wherein the prosthetic-aortic-valve control circuitry is configured to drive the one or more electrodes to apply rapid ventricular pacing.

Inventive Concept 70. The apparatus according to Inventive Concept 55, wherein the delivery-system control circuitry is configured to drive the one or more electrodes, via the delivery-system coil and the prosthetic-valve coil, to apply rapid ventricular pacing.

There is still further provided, in accordance with an Inventive Concept 71 of the present invention, a method including:
advancing, through vasculature of a patient, a delivery tube of a delivery system of a valve prosthesis system including, until a distal end of the delivery tube is disposed in an ascending aorta of the patient, while a prosthetic aortic valve of the valve prosthesis system is removably disposed in the delivery tube in a compressed delivery configuration, wherein the prosthetic aortic valve includes (a) a frame, (b) a plurality of prosthetic leaflets coupled to the frame, (c) one or more electrodes coupled to the frame, and (d) a prosthetic-valve coil coupled to the frame and in non-wireless electrical communication with the one or more electrodes;
partially releasing the prosthetic aortic valve from the distal end of the delivery tube such that the prosthetic aortic valve assumes a partially-expanded partially-deployed configuration, in which (a) at least one of one or more electrodes is positioned outside the delivery tube, and (b) the prosthetic-valve coil is compressed within the delivery tube;
thereafter, activating delivery-system control circuitry to drive a delivery-system coil to wirelessly transfer energy, by inductive coupling, to the prosthetic-valve coil at least when the prosthetic aortic valve is in the partially-deployed configuration, wherein the delivery-system coil is coupled to the delivery tube at a distal site of the delivery tube, and wherein the delivery-system control circuitry is in electrical communication with the delivery-system coil via one or more wires that pass along the delivery tube; and
thereafter, fully releasing the prosthetic aortic valve from the distal end of the delivery tube such that the prosthetic aortic valve assumes an expanded fully-deployed configuration.

Inventive Concept 72. The method according to Inventive Concept 71, further including, after fully releasing the prosthetic aortic valve from the distal end of the delivery tube, activating external-unit control circuitry of an external unit to drive an external-unit coil to wirelessly transfer energy, by inductive coupling, to the prosthetic-valve coil when the prosthetic aortic valve is in the expanded fully-deployed configuration.

Inventive Concept 73. The method according to Inventive Concept 71, wherein the delivery-system control circuitry is configured to cease driving the delivery-system coil to wirelessly transfer the energy when the prosthetic aortic valve assumes the expanded fully-deployed configuration upon being fully released from the distal end of the delivery tube.

Inventive Concept 74. The method according to Inventive Concept 71,
wherein the frame is shaped so as to define:
an upstream inflow portion,
a downstream outflow portion, and
a constriction portion, which is axially between the upstream inflow portion and the downstream outflow portion, wherein the prosthetic leaflets are coupled to the constriction portion such that free edges of the prosthetic leaflets face toward the downstream outflow portion when the prosthetic aortic valve is in the expanded fully-deployed configuration, and
wherein the prosthetic-valve coil is disposed axially along the downstream outflow portion.

Inventive Concept 75. The method according to Inventive Concept 74, wherein the prosthetic-valve coil is not disposed axially along the constriction portion or the upstream inflow portion.

Inventive Concept 76. The method according to Inventive Concept 74, wherein at least one of the one or more electrodes is coupled to the upstream inflow portion of the frame.

Inventive Concept 77. The method according to Inventive Concept 76, wherein when the prosthetic aortic valve is in the expanded fully-deployed configuration:
the frame has an inflow end at the upstream inflow portion and a downstream outflow end at the downstream outflow portion, and an axial length, measured between the inflow end and the downstream outflow end, and
at least one of the one or more electrodes is coupled to the upstream inflow portion within a distance from the inflow end, the distance equal to 10% of the axial length of the frame.

Inventive Concept 78. The method according to Inventive Concept 71,
wherein the prosthetic aortic valve further includes prosthetic-aortic-valve control circuitry, which is coupled to the frame and which is in non-wireless electrical communication with the one or more electrodes, and
wherein the prosthetic-valve coil is in non-wireless electrical communication with the prosthetic-aortic-valve control circuitry, such that the prosthetic-valve coil is in non-wireless electrical communication with the one or more electrodes via the prosthetic-aortic-valve control circuitry.

Inventive Concept 79. The method according to Inventive Concept 78,
wherein the frame is shaped so as to define:
an upstream inflow portion,
a downstream outflow portion, and
a constriction portion, which is axially between the upstream inflow portion and the downstream outflow portion, wherein the prosthetic leaflets are coupled to the constriction portion such that free edges of the prosthetic leaflets face toward the downstream outflow portion when the prosthetic aortic valve is in the expanded fully-deployed configuration,
wherein the one or more electrodes include a cathode that is coupled to the upstream inflow portion of the frame, and
wherein the prosthetic-aortic-valve control circuitry is configured to drive the cathode to apply a cathodic current.

Inventive Concept 80. The method according to Inventive Concept 78,
wherein the prosthetic leaflets are coupled to the frame at at least first and second commissures that are located at respective first and second angular locations around the frame separated by a first angular offset around the frame when the prosthetic aortic valve is in the expanded fully-deployed configuration, and
wherein the prosthetic-aortic-valve control circuitry is coupled to the frame at a third angular location around the frame that is separated from the first angular location by a second angular offset that equals between 40% and 60% of the first angular offset when the prosthetic aortic valve is in the expanded fully-deployed configuration.

Inventive Concept 81. The method according to Inventive Concept 78, wherein the prosthetic-aortic-valve control circuitry is coupled to the frame inside the frame.

Inventive Concept 82. The method according to Inventive Concept 78, wherein the prosthetic-aortic-valve control circuitry is configured to (a) use the one or more electrodes to sense a cardiac signal, and (b) drive the prosthetic-valve coil to transmit a wireless signal indicative of the sensed cardiac signal.

Inventive Concept 83. The method according to Inventive Concept 78, wherein the prosthetic-aortic-valve control circuitry is configured to drive the one or more electrodes to apply rapid ventricular pacing.

Inventive Concept 84. The method according to Inventive Concept 71, wherein activating the delivery-system control circuitry includes activating the delivery-system control circuitry to drive the one or more electrodes, via the delivery-system coil and the prosthetic-valve coil, to apply rapid ventricular pacing.

There is still further provided, in accordance with an Inventive Concept 85 of the present invention, a valve prosthesis system comprising:
(i) a prosthetic aortic valve, which comprises:
(a) a plurality of prosthetic leaflets;
(b) a frame;
(c) a cathode and an anode, which are mechanically coupled to the frame; and
(d) a prosthetic-valve coil, which is in non-wireless electrical communication with the cathode and the anode; and
(ii) a non-implantable unit, which comprises:
(a) an energy-transmission coil; and
(b) non-implantable control circuitry, which is configured to drive the cathode and the anode to apply a pacing signal and to set parameters of the pacing signal, by wirelessly transferring energy from the energy-transmission coil to the prosthetic-valve coil by inductive coupling.

Inventive Concept 86. The valve prosthesis system according to Inventive Concept 85, wherein the prosthetic aortic valve comprises one or more elongate insulated electrical conductors, which directly couple the prosthetic-valve coil in the non-wireless electrical communication with the cathode and the anode.

Inventive Concept 87. The valve prosthesis system according to Inventive Concept 85, wherein respective ends of the prosthetic-valve coil are in the non-wireless electrical communication with the cathode and the anode.

Inventive Concept 88. The valve prosthesis system according to Inventive Concept 85, wherein respective non-electrically-insulated end portions of the prosthetic-valve coil define the cathode and the anode.

Inventive Concept 89. The valve prosthesis system according to Inventive Concept 85, wherein the non-implantable control circuitry is configured to set an amplitude of the pacing signal by modulating an amplitude of the energy wirelessly transferred from the energy-transmission coil to the prosthetic-valve coil.

Inventive Concept 90. The valve prosthesis system according to Inventive Concept 85, wherein the pacing signal includes pulses, and wherein the non-implantable control circuitry is configured to drive the cathode and the anode to (a) begin application of each pulse of the pacing signal by beginning wirelessly transferring energy from the energy-transmission coil to the prosthetic-valve coil, and (b) conclude the application of each pulse of the pacing signal by ceasing wirelessly transferring energy from the energy-transmission coil to the prosthetic-valve coil.

Inventive Concept 91. The valve prosthesis system according to Inventive Concept 85, wherein the frame is shaped so as to define: (1) an upstream inflow portion, (2) a downstream outflow portion, and (3) a constriction portion, which is axially between the upstream inflow portion and the downstream outflow portion, wherein the prosthetic leaflets are coupled to the constriction portion, and wherein the cathode is mechanically coupled to the upstream inflow portion of the frame.

Inventive Concept 92. The valve prosthesis system according to Inventive Concept 91, wherein the prosthetic-valve coil is disposed axially along the downstream outflow portion of the frame.

Inventive Concept 93. The valve prosthesis system according to Inventive Concept 85, wherein the cathode and the anode are disposed on the frame such that there is at least 15 mm between the cathode and the anode, when the prosthetic aortic valve is in an expanded fully-deployed configuration, the 15 mm measured along a central longitudinal axis of the frame when in the expanded fully-deployed configuration.

Inventive Concept 94. The valve prosthesis system according to Inventive Concept 85, wherein the non-implantable unit is an external unit, which is configured to be disposed outside a body of a subject in which the prosthetic aortic valve is disposed.

Inventive Concept 95. The valve prosthesis system according to Inventive Concept 85, wherein the non-implantable unit is a delivery system, which further comprises a delivery tube, and one or more wires, which pass along the delivery tube, wherein the energy-transmission coil is a delivery-system coil, wherein the non-implantable control circuitry is delivery-system control circuitry, which is in electrical communication with the delivery-system coil via the one or more wires, and wherein the delivery-system coil is coupled to the delivery tube at a distal site of the delivery tube.

Inventive Concept 96. The valve prosthesis system according to Inventive Concept 95, wherein the delivery-system control circuitry is configured to drive the cathode and the anode to apply rapid ventricular pacing, by wirelessly transferring the energy from the energy-transmission coil to the prosthetic-valve coil by inductive coupling.

Inventive Concept 97. The valve prosthesis system according to Inventive Concept 95, wherein the prosthetic aortic valve is (i) removably disposable in the delivery tube in a compressed delivery configuration and (ii) configured to assume:

(A) a partially-expanded partially-deployed configuration upon being partially released from a distal end of the delivery tube such that (1) at least the cathode is positioned outside the delivery tube, and (2) the prosthetic-valve coil is compressed within the delivery tube, and (B) an expanded fully-deployed configuration upon being fully released from the distal end of the delivery tube, and wherein the delivery-system control circuitry is configured to drive the cathode and the anode to apply the pacing signal and to set the parameters of the pacing signal, by wirelessly transferring the energy from the energy-transmission coil to the prosthetic-valve coil at least when the prosthetic aortic valve is in the partially-deployed configuration.

Inventive Concept 98. The valve prosthesis system according to Inventive Concept 97, further comprising an external unit, which is configured to be disposed outside a body of a subject in which the prosthetic aortic valve is disposed, and which comprises:

an external-unit coil; and external-unit control circuitry, which is configured to drive the external-unit coil to drive the cathode and the anode to apply the pacing signal and to set the parameters of the pacing signal, by wirelessly transferring energy, by inductive coupling, to the prosthetic-valve coil when the prosthetic aortic valve is in the expanded fully-deployed configuration.

There is additionally provided, in accordance with an Inventive Concept 99 of the present invention, a method comprising:

deploying, via vasculature of a patient, a prosthetic aortic valve of a valve prosthesis system in an aortic valve annulus, the prosthetic aortic valve including (a) a plurality of prosthetic leaflets, (b) a frame, (c) a cathode and an anode, which are mechanically coupled to the frame, and (d) a prosthetic-valve coil, which is in non-wireless electrical communication with the cathode and the anode; and activating non-implantable control circuitry of a non-implantable unit of the valve prosthesis system to drive the cathode and the anode to apply a pacing signal and to set parameters of the pacing signal, by wirelessly transferring energy from an energy-transmission coil of the non-implantable unit to the prosthetic-valve coil by inductive coupling.

Inventive Concept 100. The method according to Inventive Concept 99, wherein the prosthetic aortic valve includes one or more elongate insulated electrical conductors, which directly couple the prosthetic-valve coil in the non-wireless electrical communication with the cathode and the anode.

Inventive Concept 101. The method according to Inventive Concept 99, wherein respective ends of the prosthetic-valve coil are in the non-wireless electrical communication with the cathode and the anode.

Inventive Concept 102. The method according to Inventive Concept 99, wherein respective non-electrically-insulated end portions of the prosthetic-valve coil define the cathode and the anode.

Inventive Concept 103. The method according to Inventive Concept 99, wherein activating the non-implantable control circuitry to drive the cathode and the anode to apply the pacing signal comprises activating the non-implantable control circuitry to set an amplitude of the pacing signal by modulating an amplitude of the energy wirelessly transferred from the energy-transmission coil to the prosthetic-valve coil.

Inventive Concept 104. The method according to Inventive Concept 99, wherein the pacing signal includes pulses, and wherein activating the non-implantable control circuitry to drive the cathode and the anode to apply the pacing signal comprises activating the non-implantable control circuitry to drive the cathode and the anode to (a) begin application of each pulse of the pacing signal by beginning wirelessly transferring energy from the energy-transmission coil to the prosthetic-valve coil, and (b) conclude the application of each pulse of the pacing signal by ceasing wirelessly transferring energy from the energy-transmission coil to the prosthetic-valve coil.

Inventive Concept 105. The method according to Inventive Concept 99, wherein the frame is shaped so as to define: (1) an upstream inflow portion, (2) a downstream outflow portion, and (3) a constriction portion, which is axially between the upstream inflow portion and the downstream outflow portion, wherein the prosthetic leaflets are coupled to the constriction portion, and wherein the cathode is mechanically coupled to the upstream inflow portion of the frame.

Inventive Concept 106. The method according to Inventive Concept 105, wherein the prosthetic-valve coil is disposed axially along the downstream outflow portion of the frame.

Inventive Concept 107. The method according to Inventive Concept 99, wherein the cathode and the anode are disposed on the frame such that there is at least 15 mm between the cathode and the anode, when the prosthetic aortic valve is in an expanded fully-deployed configuration, the 15 mm measured along a central longitudinal axis of the frame when in the expanded fully-deployed configuration.

Inventive Concept 108. The method according to Inventive Concept 99, wherein the non-implantable unit is an external unit, which is disposed outside a body of a subject in which the prosthetic aortic valve is disposed.

Inventive Concept 109. The method according to Inventive Concept 99, wherein the non-implantable unit is a delivery system of the valve prosthesis system, and the energy-transmission coil is a delivery-system coil that is coupled to a delivery tube of the delivery system at a distal site of the delivery tube, wherein the non-implantable control circuitry is delivery-system control circuitry, which is in electrical communication with the delivery-system coil via one or more wires that pass along the delivery tube, wherein deploying the prosthetic aortic valve comprises:
advancing the delivery tube through the vasculature until a distal end of the delivery tube is disposed in an ascending aorta of the patient, while the prosthetic aortic valve is removably disposed in the delivery tube in a compressed delivery configuration; and
partially releasing the prosthetic aortic valve from the distal end of the delivery tube such that the prosthetic aortic valve assumes a partially-expanded partially-deployed configuration, in which (a) at least the cathode is positioned outside the delivery tube, and (b) the prosthetic-valve coil is compressed within the delivery tube;

wherein activating the non-implantable control circuitry comprises, after partially releasing the prosthetic aortic valve from the distal end of the delivery tube, activating the delivery-system control circuitry to drive the cathode and the anode to apply the pacing signal and to set the parameters of the pacing signal, by wirelessly transferring energy from the delivery-system coil to the prosthetic-valve coil by inductive coupling at least when the prosthetic aortic valve is in the partially-deployed configuration, and wherein deploying the prosthetic aortic valve further comprises, after activating the delivery-system control circuitry, fully releasing the prosthetic aortic valve from the distal end of the delivery tube such that the prosthetic aortic valve assumes an expanded fully-deployed configuration.

Inventive Concept 110. The method according to Inventive Concept 109, wherein activating the delivery-system control circuitry comprises activating the delivery-system control circuitry to drive the cathode and the anode to apply rapid ventricular pacing, by wirelessly transferring the energy from the energy-transmission coil to the prosthetic-valve coil by inductive coupling at least when the prosthetic aortic valve is in the partially-deployed configuration.

Inventive Concept 111. The method according to Inventive Concept 109, further comprising, after fully releasing the prosthetic aortic valve from the distal end of the delivery tube, activating external-unit control circuitry of an external unit to drive an external-unit coil of the external unit to drive the cathode and the anode to apply the pacing signal and to set the parameters of the pacing signal, by wirelessly transferring energy, by inductive coupling, to the prosthetic-valve coil when the prosthetic aortic valve is in the expanded fully-deployed configuration, wherein the external unit is disposed outside a body of a subject in which the prosthetic aortic valve is disposed.

Inventive Concept 112. The method according to Inventive Concept 109, wherein the delivery-system control circuitry is configured to cease driving the delivery-system coil to drive the cathode and the anode when the prosthetic aortic valve assumes the expanded fully-deployed configuration upon being fully released from the distal end of the delivery tube.

Inventive Concept 113. The method according to Inventive Concept 109, wherein partially releasing the prosthetic aortic valve from the distal end of the delivery tube comprises positioning the cathode adjacent to cardiac tissue near the bundle of His.

Inventive Concept 114. The method according to Inventive Concept 113, wherein positioning the cathode adjacent to the cardiac tissue near the bundle of His comprises rotating the prosthetic aortic valve if necessary during deployment such that the cathode is disposed against the cardiac tissue near the bundle of His.

There is yet additionally provided, in accordance with an Inventive Concept 115 of the present invention, a valve prosthesis system including:

(i) a prosthetic aortic valve, which is configured to be implanted in a native aortic valve of a patient, and which includes:
(a) a plurality of prosthetic leaflets;
(b) a frame;
(c) a cathode and an anode, which are mechanically coupled to the frame; and
(d) a prosthetic-valve coil, which is in non-wireless electrical communication with the cathode and the anode, wherein the prosthetic aortic valve does not include any active electronic components; and (ii) a non-implantable unit, which includes:

(a) an energy-transmission coil;
(b) at least two sensing skin ECG electrodes; and
(c) non-implantable control circuitry, which is configured to:
   drive the cathode and the anode to apply a pacing signal to a heart of the patient,
   detect at least one cardiac parameter using the at least two sensing skin ECG electrodes, and
   at least partially responsively to the detected at least one cardiac parameter, set parameters of the pacing signal, by wirelessly transferring energy from the energy-transmission coil to the prosthetic-valve coil by inductive coupling.

There is also provided, in accordance with an Inventive Concept 116 of the present invention, a valve prosthesis system including:

(i) a prosthetic aortic valve, which is configured to be implanted in a native aortic valve of a patient, and which includes:
   (a) a plurality of prosthetic leaflets;
   (b) a frame;
   (c) a cathode and an anode, which are mechanically coupled to the frame; and
   (d) a prosthetic-valve coil, which is in non-wireless electrical communication with the cathode and the anode, wherein the prosthetic aortic valve does not include any active electronic components; and
(ii) a non-implantable unit, which includes:
   (a) an energy-transmission coil;
   (b) a cardiac sensor; and
   (c) non-implantable control circuitry, which is configured to:
      drive the cathode and the anode to apply a pacing signal to a heart of the patient,
      detect at least one cardiac parameter using the cardiac sensor, and
      at least partially responsively to the detected at least one cardiac parameter, set parameters of the pacing signal, by wirelessly transferring energy from the energy-transmission coil to the prosthetic-valve coil by inductive coupling.

Inventive Concept 117. The valve prosthesis system according to any one of Inventive Concepts 115 and 116, wherein the non-implantable control circuitry is configured to:
   analyze the detected at least one cardiac parameter to assess a level of responsiveness of the heart to the pacing signal, and
   upon ascertaining that the level of responsiveness is unsatisfactory, increase a strength of the pacing signal responsively to the detected at least one cardiac parameter.

Inventive Concept 118. The valve prosthesis system according to any one of Inventive Concepts 115 and 116,
   wherein the at least one cardiac parameter includes at least one timing feature,
   wherein the parameters of the pacing signal include at least one timing parameter, and
   wherein the non-implantable control circuitry is configured to set the at least one timing parameter of the pacing signal responsively to the at least one timing feature of the detected at least one cardiac parameter.

Inventive Concept 119. The valve prosthesis system according to any one of Inventive Concepts 115 and 116, wherein the prosthetic aortic valve includes one or more elongate insulated electrical conductors, which directly couple the prosthetic-valve coil in the non-wireless electrical communication with the cathode and the anode.

Inventive Concept 120. The valve prosthesis system according to any one of Inventive Concepts 115 and 116, wherein respective non-electrically-insulated end portions of the prosthetic-valve coil define the cathode and the anode.

Inventive Concept 121. The valve prosthesis system according to any one of Inventive Concepts 115 and 116, wherein the non-implantable control circuitry is configured to set an amplitude of the pacing signal by modulating an amplitude of the energy wirelessly transferred from the energy-transmission coil to the prosthetic-valve coil.

Inventive Concept 122. The valve prosthesis system according to any one of Inventive Concepts 115 and 116, wherein the pacing signal includes pulses, and wherein the non-implantable control circuitry is configured to drive the cathode and the anode to (a) begin application of each pulse of the pacing signal by beginning wirelessly transferring energy from the energy-transmission coil to the prosthetic-valve coil, and (b) conclude the application of each pulse of the pacing signal by ceasing wirelessly transferring energy from the energy-transmission coil to the prosthetic-valve coil.

Inventive Concept 123. The valve prosthesis system according to any one of Inventive Concepts 115-122, wherein the non-implantable unit is an external unit, which is configured to be disposed outside a body of the patient.

Inventive Concept 124. The valve prosthesis system according to any one of Inventive Concepts 115-122,
   wherein the non-implantable unit is a delivery system, which further includes a delivery tube, and one or more wires, which pass along the delivery tube,
   wherein the energy-transmission coil is a delivery-system coil,
   wherein the non-implantable control circuitry is delivery-system control circuitry, which is in electrical communication with the delivery-system coil via the one or more wires, and
   wherein the delivery-system coil is coupled to the delivery tube at a distal site of the delivery tube.

Inventive Concept 125. The valve prosthesis system according to Inventive Concept 124, wherein the delivery-system control circuitry is configured to drive the cathode and the anode to apply rapid ventricular pacing, by wirelessly transferring the energy from the energy-transmission coil to the prosthetic-valve coil by inductive coupling.

Inventive Concept 126. The valve prosthesis system according to any one of Inventive Concepts 115-122,
   wherein the non-implantable control circuitry is configured to wirelessly transfer the energy by generating a plurality of AC pulses, each including a train of AC bursts, and
   wherein the prosthetic aortic valve includes a passive diode, which is coupled in electrical communication with the prosthetic-valve coil, and is configured to rectify current in the prosthetic-valve coil.

Inventive Concept 127. The valve prosthesis system according to inventive Concept 126, wherein the non-implantable control circuitry is configured to generate the train of AC bursts at a frequency of between 3 kHz and 130 kHz, such as between 3 kHz and 100 kHz, or between 100 kHz and 130 kHz.

Inventive Concept 128. The valve prosthesis system according to Inventive Concept 126, wherein the non-implantable control circuitry is configured to include 20-100 AC bursts in each of the AC pulses.

There is also provided, in accordance with an Inventive Concept 129 of the present invention, a method including:

implanting, in a native aortic valve of a patient, via vasculature of the patient, a prosthetic aortic valve of a valve prosthesis system in an aortic valve annulus, the prosthetic aortic valve including (a) a plurality of prosthetic leaflets, (b) a frame, (c) a cathode and an anode, which are mechanically coupled to the frame, and (d) a prosthetic-valve coil, which is in non-wireless electrical communication with the cathode and the anode, wherein the prosthetic aortic valve does not include any active electronic components; and activating non-implantable control circuitry of a non-implantable unit of the valve prosthesis system to drive the cathode and the anode to apply a pacing signal to a heart of the patient; detect at least one cardiac parameter using a cardiac sensor; and at least partially responsively to the detected at least one cardiac parameter, set parameters of the pacing signal, by wirelessly transferring energy from an energy-transmission coil of the non-implantable unit to the prosthetic-valve coil by inductive coupling.

Inventive Concept 130. The method according to Inventive Concept 129, wherein activating the non-implantable control circuitry includes activating the non-implantable control circuitry to:

analyze the detected at least one cardiac parameter to assess a level of responsiveness of the heart to the pacing signal, and upon ascertaining that the level of responsiveness is unsatisfactory, increase a strength of the pacing signal responsively to the detected at least one cardiac parameter.

Inventive Concept 131. The method according to Inventive Concept 129, wherein the at least one cardiac parameter includes at least one timing feature, wherein the parameters of the pacing signal include at least one timing parameter, and wherein activating the non-implantable control circuitry includes activating the non-implantable control circuitry to set the at least one timing parameter of the pacing signal responsively to the at least one timing feature of the detected at least one cardiac parameter.

Inventive Concept 132. The method according to Inventive Concept 129, wherein activating the non-implantable control circuitry to drive the cathode and the anode to apply the pacing signal includes activating the non-implantable control circuitry to set an amplitude of the pacing signal by modulating an amplitude of the energy wirelessly transferred from the energy-transmission coil to the prosthetic-valve coil.

Inventive Concept 133. The method according to Inventive Concept 129, wherein the pacing signal includes pulses, and wherein activating the non-implantable control circuitry to drive the cathode and the anode to apply the pacing signal includes activating the non-implantable control circuitry to drive the cathode and the anode to (a) begin application of each pulse of the pacing signal by beginning wirelessly transferring energy from the energy-transmission coil to the prosthetic-valve coil, and (b) conclude the application of each pulse of the pacing signal by ceasing wirelessly transferring energy from the energy-transmission coil to the prosthetic-valve coil.

Inventive Concept 134. The method according to Inventive Concept 129, wherein the non-implantable unit is an external unit, which is disposed outside a body of the patient.

Inventive Concept 135. The method according to Inventive Concept 129, wherein activating the non-implantable control circuitry includes activating the non-implantable control circuitry to wirelessly transfer the energy by generating a plurality of AC pulses, each including a train of AC bursts, and wherein the prosthetic aortic valve includes a passive diode, which is coupled in electrical communication with the prosthetic-valve coil, and is configured to rectify current in the prosthetic-valve coil.

Inventive Concept 136. The method according to Inventive Concept 135, wherein activating the non-implantable control circuitry includes activating the non-implantable control circuitry to generate the train of AC bursts at a frequency of between 3 kHz and 130 kHz, such as between 3 kHz and 100 kHz, or between 100 kHz and 130 kHz.

Inventive Concept 137. The method according to Inventive Concept 135, wherein activating the non-implantable control circuitry includes activating the non-implantable control circuitry to include 20-100 AC bursts in each of the AC pulses.

There is further provided, in accordance with an Inventive Concept 138 of the present invention, a valve prosthesis system comprising:

(i) a prosthetic aortic valve, which comprises:
(a) a plurality of prosthetic leaflets;
(b) a frame;
(c) a cathode and an anode, which are mechanically coupled to the frame; and
(d) a prosthetic-valve coil, which is in non-wireless electrical communication with the cathode and the anode; and (ii) a non-implantable unit, which comprises:
(a) an energy-transmission coil; and
(b) non-implantable control circuitry, which is configured to drive the cathode and the anode to:
apply a pacing signal, which includes pulses, and to set parameters of the pacing signal, by wirelessly transferring energy from the energy-transmission coil to the prosthetic-valve coil by inductive coupling,
begin application of each pulse of the pacing signal by beginning wirelessly transferring the energy from the energy-transmission coil to the prosthetic-valve coil, and
conclude the application of each pulse of the pacing signal by ceasing wirelessly transferring the energy from the energy-transmission coil to the prosthetic-valve coil.

Inventive Concept 139. The valve prosthesis system according to Inventive Concept 138, wherein the prosthetic aortic valve comprises one or more elongate insulated electrical conductors, which directly couple the prosthetic-valve coil in the non-wireless electrical communication with the cathode and the anode.

Inventive Concept 140. The valve prosthesis system according to Inventive Concept 138, wherein respective ends of the prosthetic-valve coil are in the non-wireless electrical communication with the cathode and the anode.

Inventive Concept 141. The valve prosthesis system according to Inventive Concept 138, wherein respective non-electrically-insulated end portions of the prosthetic-valve coil define the cathode and the anode.

Inventive Concept 142. The valve prosthesis system according to Inventive Concept 138, wherein the non-implantable control circuitry is configured to set an amplitude of the pacing signal by modulating an amplitude of the energy wirelessly transferred from the energy-transmission coil to the prosthetic-valve coil.

Inventive Concept 143. The valve prosthesis system according to Inventive Concept 138, wherein the frame is shaped so as to define: (1) an upstream inflow portion, (2) a downstream outflow portion, and (3) a constriction portion, which is axially between the upstream inflow portion and the downstream outflow portion, wherein the prosthetic leaflets are coupled to the constriction portion, and wherein the cathode is mechanically coupled to the upstream inflow portion of the frame.

Inventive Concept 144. The valve prosthesis system according to Inventive Concept 143, wherein the prosthetic-valve coil is disposed axially along the downstream outflow portion of the frame.

Inventive Concept 145. The valve prosthesis system according to Inventive Concept 138, wherein the cathode and the anode are disposed on the frame such that there is at least 15 mm between the cathode and the anode, when the prosthetic aortic valve is in an expanded fully-deployed configuration, the 15 mm measured along a central longitudinal axis of the frame when in the expanded fully-deployed configuration.

Inventive Concept 146. The valve prosthesis system according to any one of Inventive Concepts 138-145, wherein the non-implantable unit is an external unit, which is configured to be disposed outside a body of a subject in which the prosthetic aortic valve is disposed.

Inventive Concept 147. The valve prosthesis system according to any one of inventive Concepts 138-145, wherein the non-implantable unit is a delivery system, which further comprises a delivery tube, and one or more wires, which pass along the delivery tube, wherein the energy-transmission coil is a delivery-system coil, wherein the non-implantable control circuitry is delivery-system control circuitry, which is in electrical communication with the delivery-system coil via the one or more wires, and wherein the delivery-system coil is coupled to the delivery tube at a distal site of the delivery tube.

Inventive Concept 148. The valve prosthesis system according to Inventive Concept 147, wherein the delivery-system control circuitry is configured to drive the cathode and the anode to apply rapid ventricular pacing, by wirelessly transferring the energy from the energy-transmission coil to the prosthetic-valve coil by inductive coupling.

Inventive Concept 149. The valve prosthesis system according to Inventive Concept 147, wherein the prosthetic aortic valve is (i) removably disposable in the delivery tube in a compressed delivery configuration and (ii) configured to assume:

(A) a partially-expanded partially-deployed configuration upon being partially released from a distal end of the delivery tube such that (1) at least the cathode is positioned outside the delivery tube, and (2) the prosthetic-valve coil is compressed within the delivery tube, and (B) an expanded fully-deployed configuration upon being fully released from the distal end of the delivery tube, and wherein the delivery-system control circuitry is configured to drive the cathode and the anode to apply the pacing signal and to set the parameters of the pacing signal, by wirelessly transferring the energy from the energy-transmission coil to the prosthetic-valve coil at least when the prosthetic aortic valve is in the partially-deployed configuration.

Inventive Concept 150. The valve prosthesis system according to Inventive Concept 149, further comprising an external unit, which is configured to be disposed outside a body of a subject in which the prosthetic aortic valve is disposed, and which comprises:

an external-unit coil; and external-unit control circuitry, which is configured to drive the external-unit coil to drive the cathode and the anode to apply the pacing signal and to set the parameters of the pacing signal, by wirelessly transferring energy, by inductive coupling, to the prosthetic-valve coil when the prosthetic aortic valve is in the expanded fully-deployed configuration.

There is further provided, in accordance with an Inventive Concept 151 of the present invention, a prosthetic aortic valve, which is configured to be delivered to a native aortic valve of a patient in a constrained delivery configuration within a delivery sheath, and which includes:

a frame;

a plurality of prosthetic leaflets coupled to the frame;

a cathode and an anode, which are mechanically coupled to the frame; and a prosthetic-valve coil, which is coupled to the frame and is in non-wireless electrical communication with the cathode and the anode, wherein when the prosthetic aortic valve is in an expanded fully-deployed configuration upon release from the delivery sheath, (a) a line defined between upstream-most and downstream-most points of mechanical coupling between the prosthetic-valve coil and the frame and (b) a central longitudinal axis defined by the frame form an angle of between 20 and 70 degrees.

Inventive Concept 152. The prosthetic aortic valve according to Inventive Concept 151, wherein the angle is between 30 and 60 degrees.

Inventive Concept 153. The prosthetic aortic valve according to Inventive Concept 151, wherein respective non-electrically-insulated end portions of the prosthetic-valve coil define the cathode and the anode.

Inventive Concept 154. The prosthetic aortic valve according to Inventive Concept 151, wherein the prosthetic aortic valve does not include any active electronic components.

Inventive Concept 155. The prosthetic aortic valve according to Inventive Concept 151, wherein when the prosthetic aortic valve is in the expanded fully-deployed configuration, the central longitudinal axis passes through a space surrounded by the prosthetic-valve coil.

Inventive Concept 156. The prosthetic aortic valve according to Inventive Concept 151, wherein when the prosthetic aortic valve is in the expanded fully-deployed configuration, (a) a downstream-most point of mechanical coupling between the prosthetic-valve coil and the frame and (b) a centroid of the cathode are rotationally aligned with each other or rotationally offset from each other about the central longitudinal axis by less than 50 degrees.

Inventive Concept 157. The prosthetic aortic valve according to Inventive Concept 151, wherein the cathode is located upstream of the anode along the frame.

Inventive Concept 158. The prosthetic aortic valve according to any one of Inventive Concepts 151-157, wherein when the prosthetic aortic valve is in the expanded fully-deployed configuration, the frame is shaped so as to define:

(a) an upstream inflow portion, (b) a downstream outflow portion, and (c) a constriction portion, which is axially between the upstream inflow portion and the downstream outflow portion, wherein the prosthetic leaflets are coupled to the constriction portion, and wherein when the prosthetic aortic valve is in the expanded fully-deployed configuration, free edges of the prosthetic leaflets face toward the downstream outflow portion, and wherein the cathode is coupled to the upstream inflow portion of the frame.

Inventive Concept 159. The prosthetic aortic valve according to any one of Inventive Concepts 151-157, wherein when the prosthetic aortic valve is in the expanded fully-deployed configuration, the frame is shaped so as to define:

(a) an upstream inflow portion, (b) a downstream outflow portion, and (c) a constriction portion, which is axially between the upstream inflow portion and the downstream outflow portion, wherein the prosthetic leaflets are coupled to the constriction portion, and wherein when the prosthetic aortic valve is in the expanded fully-deployed configuration, (A) free edges of the prosthetic leaflets face toward the downstream outflow portion, and (B) a ring-shaped longitudinal border between the downstream outflow portion and the constriction portion is defined by a downstream-most point of the frame to which the prosthetic leaflets are coupled, and wherein a downstream-most point of mechanical coupling between the prosthetic-valve coil and the frame is located on the downstream outflow portion when the prosthetic aortic valve is in the expanded fully-deployed configuration.

Inventive Concept 160. The apparatus according to Inventive Concept 159, wherein an upstream-most point of mechanical coupling between the prosthetic-valve coil and the frame is located on the constriction portion when the prosthetic aortic valve is in the expanded fully-deployed configuration.

Inventive Concept 161. A valve prosthesis system including the prosthetic aortic valve according to any one of Inventive Concepts 151-157, the valve prosthesis system further including an external unit, which is configured to be disposed outside a body of the patient, and which includes:

an energy-transmission coil; and external-unit control circuitry, which is configured to drive the energy-transmission coil to wirelessly transfer energy to the prosthetic-valve coil by inductive coupling.

Inventive Concept 162. The valve prosthesis system according to Inventive Concept 161, wherein the external-unit control circuitry is configured to drive the cathode and the anode to apply a pacing signal to a heart of the patient, by wirelessly transferring the energy from the energy-transmission coil to the prosthetic-valve coil by inductive coupling.

Inventive Concept 163. The valve prosthesis system according to Inventive Concept 162, wherein the external unit further includes a cardiac sensor, and wherein the external-unit control circuitry is configured to:

detect at least one cardiac parameter using the cardiac sensor, and at least partially responsively to the detected at least one cardiac parameter, set parameters of the pacing signal, by wirelessly transferring the energy from the energy-transmission coil to the prosthetic-valve coil by inductive coupling.

Inventive Concept 164. The valve prosthesis system according to inventive Concept 163, wherein the cardiac sensor includes at least two sensing skin ECG electrodes.

Inventive Concept 165. The valve prosthesis system according to Inventive Concept 161, wherein the external-unit control circuitry is configured to wirelessly transfer the energy by generating a plurality of AC pulses, each including a train of AC bursts, and wherein the prosthetic aortic valve includes a passive diode, which is coupled in electrical communication with the prosthetic-valve coil, and is configured to rectify current in the prosthetic-valve coil.

Inventive Concept 166. The valve prosthesis system according to inventive Concept 165, wherein the external-unit control circuitry is configured to generate the train of AC bursts at a frequency of between 3 kHz and 130 kHz.

Inventive Concept 167. The valve prosthesis system according to Inventive Concept 165, wherein the external-unit control circuitry is configured to include 20-100 AC bursts in each of the AC pulses.

There is further provided, in accordance with an Inventive Concept 168 of the present invention, a method including:

delivering, to a native aortic valve of a patient, via vasculature of the patient, a prosthetic aortic valve while in a constrained delivery configuration within a delivery sheath, the prosthetic aortic valve including (a) a frame, (b) a plurality of prosthetic leaflets coupled to the frame, (c) a cathode and an anode, which are mechanically coupled to the frame, and (d) a prosthetic-valve coil, which is coupled to the frame in non-wireless electrical communication with the cathode and the anode; and releasing the prosthetic aortic valve from the delivery sheath, such that the prosthetic aortic valve transitions to an expanded fully-deployed configuration, in which (a) a line defined between upstream-most and downstream-most points of mechanical coupling between the prosthetic-valve coil and the frame and (b) a central longitudinal axis defined by the frame form an angle of between 20 and 70 degrees.

Inventive Concept 169. The method according to Inventive Concept 168, wherein the angle is between 30 and 60 degrees.

Inventive Concept 170. The method according to Inventive Concept 168, wherein the prosthetic aortic valve does not include any active electronic components.

Inventive Concept 172. The method according to Inventive Concept 168, wherein releasing the prosthetic aortic valve from the delivery sheath includes releasing the prosthetic aortic valve from the delivery sheath, such that the prosthetic aortic valve transitions to the expanded fully-deployed configuration, in which the central longitudinal axis passes through a space surrounded by the prosthetic-valve coil.

Inventive Concept 172. The method according to Inventive Concept 168, further including rotationally orienting the prosthetic aortic valve such that the prosthetic-valve coil faces generally anterio-superiorly toward a sternum of the patient.

Inventive Concept 173. The method according to Inventive Concept 172, wherein when the prosthetic aortic valve is in the expanded fully-deployed configuration, (a) a downstream-most point of mechanical coupling between the prosthetic-valve coil and the frame and (b) a centroid of the cathode are rotationally aligned with each other or rotationally offset from each other about the central longitudinal axis by less than 50 degrees, and wherein rotationally orienting the prosthetic aortic valve includes aligning the cathode adjacent to cardiac tissue near a bundle of His of the patient, so as to automatically align the prosthetic-valve coil facing generally anterio-superiorly toward a sternum of the patient.

Inventive Concept 174. The method according to Inventive Concept 168, wherein releasing the prosthetic aortic valve from the delivery sheath includes releasing the prosthetic aortic valve from the delivery sheath, such that the prosthetic aortic valve transitions to the expanded fully-deployed configuration, the cathode is located upstream of the anode along the frame.

Inventive Concept 175. The method according to Inventive Concept 168,
wherein releasing the prosthetic aortic valve from the delivery sheath includes releasing the prosthetic aortic valve from the delivery sheath, such that the prosthetic aortic valve transitions to the expanded fully-deployed configuration, in which the frame is shaped so as to define:
  (a) an upstream inflow portion,
  (b) a downstream outflow portion, and
  (c) a constriction portion, which is axially between the upstream inflow portion and the downstream outflow portion, wherein the prosthetic leaflets are coupled to the constriction portion, and wherein when the prosthetic aortic valve is in the expanded fully-deployed configuration, free edges of the prosthetic leaflets face toward the downstream outflow portion, and
wherein the cathode is coupled to the upstream inflow portion of the frame.

Inventive Concept 176. The method according to Inventive Concept 168,
wherein releasing the prosthetic aortic valve from the delivery sheath includes releasing the prosthetic aortic valve from the delivery sheath, such that the prosthetic aortic valve transitions to the expanded fully-deployed configuration, in which the frame is shaped so as to define:
  (a) an upstream inflow portion,
  (b) a downstream outflow portion, and
  (c) a constriction portion, which is axially between the upstream inflow portion and the downstream outflow portion, wherein the prosthetic leaflets are coupled to the constriction portion, and wherein when the prosthetic aortic valve is in the expanded fully-deployed configuration, (A) free edges of the prosthetic leaflets face toward the downstream outflow portion, and (B) a ring-shaped longitudinal border between the downstream outflow portion and the constriction portion is defined by a downstream-most point of the frame to which the prosthetic leaflets are coupled, and
wherein a downstream-most point of mechanical coupling between the prosthetic-valve coil and the frame is located on the downstream outflow portion.

Inventive Concept 177. The method according to Inventive Concept 176, wherein an upstream-most point of mechanical coupling between the prosthetic-valve coil and the frame is located on the constriction portion.

Inventive Concept 178. The method according to Inventive Concept 168, further including activating external-unit control circuitry of an external unit, disposed outside a body of the patient, to drive an energy-transmission coil of the external unit to wirelessly transfer energy to the prosthetic-valve coil by inductive coupling.

Inventive Concept 179. The method according to Inventive Concept 178, further including positioning the energy-transmission coil against a chest of the patient, over a sternum of the patient.

Inventive Concept 180. The method according to Inventive Concept 178, further including positioning the energy-transmission coil around a neck of the patient.

Inventive Concept 181. The method according to Inventive Concept 178, wherein activating the external-unit control circuitry includes activating the external-unit control circuitry to drive the cathode and the anode to apply a pacing signal to a heart of the patient, by wirelessly transferring the energy from the energy-transmission coil to the prosthetic-valve coil by inductive coupling.

Inventive Concept 182. The method according to Inventive Concept 181, wherein activating the external-unit control circuitry includes activating the external-unit control circuitry to:
  detect at least one cardiac parameter using a cardiac sensor, and
  at least partially responsively to the detected at least one cardiac parameter, set parameters of the pacing signal, by wirelessly transferring the energy from the energy-transmission coil to the prosthetic-valve coil by inductive coupling.

Inventive Concept 183. The method according to Inventive Concept 182, wherein the cardiac sensor includes at least two sensing skin ECG electrodes placed on skin of the patient.

Inventive Concept 184. The method according to Inventive Concept 178,
wherein activating the external-unit control circuitry includes activating the external-unit control circuitry to wirelessly transfer the energy by generating a plurality of AC pulses, each including a train of AC bursts, and
wherein the prosthetic aortic valve includes a passive diode, which is coupled in electrical communication with the prosthetic-valve coil, and is configured to rectify current in the prosthetic-valve coil.

Inventive Concept 185. The method according to Inventive Concept 184, wherein activating the external-unit control circuitry includes activating the external-unit control circuitry to generate the train of AC bursts at a frequency of between 3 kHz and 130 kHz.

Inventive Concept 186. The method according to Inventive Concept 184, wherein activating the external-unit control circuitry includes activating the external-unit control circuitry to include 20-100 AC bursts in each of the AC pulses.

There is still further provided, in accordance with an Inventive Concept 187 of the present invention, a prosthetic aortic valve, which is configured to be delivered to a native aortic valve of a patient in a constrained delivery configuration within a delivery sheath, and which comprises:
  a frame, which comprises interconnected stent struts arranged so as to define interconnected stent cells;
  a plurality of prosthetic leaflets coupled to the frame;
  a cathode and an anode, which are mechanically coupled to the frame; and
  a prosthetic-valve coil, which is in non-wireless electrical communication with the cathode and the anode, and is coupled to a plurality of the stent struts, running along the stent struts so as to surround a plurality of the stent cells when the prosthetic aortic valve is in an expanded fully-deployed configuration upon release from the delivery sheath.

Inventive Concept 188. The prosthetic aortic valve according to Inventive Concept 187, wherein the prosthetic-valve coil is shaped generally as a diamond when the prosthetic aortic valve is in the expanded fully-deployed configuration.

Inventive Concept 189. The prosthetic aortic valve according to Inventive Concept 187, wherein the prosthetic-valve coil is shaped so that no single line crosses, more than twice, a projection of the prosthetic-valve coil onto a best-fit plane when the prosthetic aortic valve is in the expanded fully-deployed configuration.

Inventive Concept 190. The prosthetic aortic valve according to Inventive Concept 187, wherein the prosthetic-valve coil is not shaped so as to define any zigzags when the prosthetic aortic valve is in the expanded fully-deployed configuration.

Inventive Concept 191. The prosthetic aortic valve according to Inventive Concept 187, wherein the plurality of the stent cells surrounded by the prosthetic-valve coil comprises at least 4 stent cells.

Inventive Concept 192. The prosthetic aortic valve according to Inventive Concept 191, wherein the plurality of the stent cells surrounded by the prosthetic-valve coil comprises at least 9 stent cells.

Inventive Concept 193. The prosthetic aortic valve according to Inventive Concept 192, wherein the plurality of the stent cells surrounded by the prosthetic-valve coil comprises at least 16 stent cells.

Inventive Concept 194. The prosthetic aortic valve according to Inventive Concept 187, wherein the plurality of the stent cells surrounded by the prosthetic-valve coil comprises no more than 32 stent cells.

Inventive Concept 195. The prosthetic aortic valve according to Inventive Concept 187, wherein the prosthetic-valve coil has a perimeter of between 4 and 8 cm when the prosthetic aortic valve is in the expanded fully-deployed configuration.

Inventive Concept 196. The prosthetic aortic valve according to Inventive Concept 187, wherein the prosthetic-valve coil is shaped so as to define 1 to 4 turns.

Inventive Concept 197. The prosthetic aortic valve according to Inventive Concept 187, wherein the prosthetic-valve coil has a first dimension of between 2 and 4 cm, the first dimension measured parallel to a central longitudinal axis defined by the frame when the prosthetic aortic valve is in the expanded fully-deployed configuration.

Inventive Concept 198. The prosthetic aortic valve according to Inventive Concept 187, wherein the prosthetic-valve coil has a second dimension of between 1 and 3 cm, the second dimension measured around a central longitudinal axis defined by the frame when the prosthetic aortic valve is in the expanded fully-deployed configuration.

Inventive Concept 199. The prosthetic aortic valve according to Inventive Concept 187, wherein the prosthetic-valve coil has a first dimension of between 2 and 4 cm and a second dimension of between 1 and 3 cm, the first dimension measured parallel to a central longitudinal axis defined by the frame, and the second dimension measured around the central longitudinal axis, when the prosthetic aortic valve is in the expanded fully-deployed configuration.

Inventive Concept 200. The prosthetic aortic valve according to Inventive Concept 187, wherein the prosthetic-valve coil has a second dimension of between 30 and 180 degrees, the second dimension measured in degrees around the frame with respect to a central longitudinal axis defined by the frame when the prosthetic aortic valve is in the expanded fully-deployed configuration.

Inventive Concept 201. The prosthetic aortic valve according to Inventive Concept 200, wherein the second dimension is between 30 and 150 degrees.

Inventive Concept 202. The prosthetic aortic valve according to Inventive Concept 200, wherein the second dimension is between 90 and 180 degrees.

Inventive Concept 203. The prosthetic aortic valve according to Inventive Concept 202, wherein the second dimension is between 90 and 150 degrees.

Inventive Concept 204. The prosthetic aortic valve according to Inventive Concept 187, wherein the prosthetic-valve coil surrounds an area of between 1 and 4 cm2 when the prosthetic aortic valve is in the expanded fully-deployed configuration.

Inventive Concept 205. The prosthetic aortic valve according to Inventive Concept 187, wherein the prosthetic-valve coil has a second dimension of between 1 and 3 cm, the second dimension measured around a central longitudinal axis defined by the frame when the prosthetic aortic valve is in the expanded fully-deployed configuration.

Inventive Concept 206. The prosthetic aortic valve according to Inventive Concept 187, wherein the stent struts comprise a shape-memory alloy.

Inventive Concept 207. The prosthetic aortic valve according to Inventive Concept 187, wherein the prosthetic aortic valve does not comprise any commissural posts.

Inventive Concept 208. The prosthetic aortic valve according to Inventive Concept 187, wherein respective non-electrically-insulated end portions of the prosthetic-valve coil define the cathode and the anode.

Inventive Concept 209. The prosthetic aortic valve according to Inventive Concept 187, wherein the cathode is located upstream of the anode along the frame.

Inventive Concept 210. The prosthetic aortic valve according to Inventive Concept 187,
   wherein when the prosthetic aortic valve is in the expanded fully-deployed configuration, the frame is shaped so as to define:
      (a) an upstream inflow portion,
      (b) a downstream outflow portion, and
      (c) a constriction portion, which is axially between the upstream inflow portion and the downstream outflow portion, wherein the prosthetic leaflets are coupled to the constriction portion, and wherein when the prosthetic aortic valve is in the expanded fully-deployed configuration, free edges of the prosthetic leaflets face toward the downstream outflow portion, and wherein the cathode is coupled to the upstream inflow portion of the frame.

Inventive Concept 211. The prosthetic aortic valve according to any one of Inventive Concepts 187-210, wherein the prosthetic aortic valve comprises exactly one prosthetic-valve coil.

Inventive Concept 212. The prosthetic aortic valve according to any one of Inventive Concepts 187-210,
   wherein the prosthetic-valve coil is a first prosthetic-valve coil, the plurality of the stent struts is a first plurality of the stent struts, and the plurality of the stent cells is a first plurality of the stent cells,
   wherein the prosthetic aortic valve further comprises a second prosthetic-valve coil, which is in non-wireless electrical communication with the cathode and the anode, and is coupled to a second plurality of the stent struts, running along the stent struts so as to surround a second plurality of the stent cells when the prosthetic aortic valve is in the expanded fully-deployed configuration, and
   wherein the first and the second pluralities of the stent cells do not include any common stent cells.

Inventive Concept 213. The prosthetic aortic valve according to Inventive Concept 212, wherein the first and the second prosthetic-valve coils comprise a single wire that is shaped so as to define both the first and the second prosthetic-valve coils.

Inventive Concept 214. The prosthetic aortic valve according to Inventive Concept 212, wherein respective centroids of the first and the second prosthetic-valve coils are offset from each other by at least 90 degrees around a central longitudinal axis defined by the frame when the prosthetic aortic valve is in the expanded fully-deployed configuration.

Inventive Concept 215. The prosthetic aortic valve according to Inventive Concept 214, wherein the respective centroids are offset from each other by 180 degrees around the central longitudinal axis when the prosthetic aortic valve is in the expanded fully-deployed configuration.

Inventive Concept 216. The prosthetic aortic valve according to any one of Inventive Concepts 187-210, wherein the prosthetic aortic valve does not comprise any active electronic components.

Inventive Concept 217. The prosthetic aortic valve according to any one of Inventive Concepts 187-210, wherein when the prosthetic aortic valve is in the expanded fully-deployed configuration, (a) a centroid of the prosthetic-valve coil and the frame and (b) a centroid of the cathode are rotationally offset from each other about a central longitudinal axis by an angle of at least 150 degrees when the prosthetic aortic valve is in the expanded fully-deployed configuration, the central longitudinal axis defined by the frame when the prosthetic aortic valve is in the expanded fully-deployed configuration.

Inventive Concept 218. The prosthetic aortic valve according to Inventive Concept 217, wherein the angle is at least 160 degrees.

Inventive Concept 219. A valve prosthesis system comprising the prosthetic aortic valve according to any one of Inventive Concepts 187-210, the valve prosthesis system further comprising an external unit, which is configured to be disposed outside a body of the patient, and which comprises:
  an energy-transmission coil; and
  external-unit control circuitry, which is configured to drive the energy-transmission coil to wirelessly transfer energy to the prosthetic-valve coil by inductive coupling.

Inventive Concept 220. The valve prosthesis system according to Inventive Concept 219, wherein the external-unit control circuitry is configured to drive the cathode and the anode to apply a pacing signal to a heart of the patient, by wirelessly transferring the energy from the energy-transmission coil to the prosthetic-valve coil by inductive coupling.

Inventive Concept 221. The valve prosthesis system according to Inventive Concept 220,
  wherein the external unit further comprises a cardiac sensor, and
  wherein the external-unit control circuitry is configured to:
    detect at least one cardiac parameter using the cardiac sensor, and
    at least partially responsively to the detected at least one cardiac parameter, set parameters of the pacing signal, by wirelessly transferring the energy from the energy-transmission coil to the prosthetic-valve coil by inductive coupling.

Inventive Concept 222. The valve prosthesis system according to Inventive Concept 221, wherein the cardiac sensor comprises at least two sensing skin ECG electrodes.

Inventive Concept 223. The valve prosthesis system according to Inventive Concept 219,
  wherein the external-unit control circuitry is configured to wirelessly transfer the energy by generating a plurality of AC pulses, each including a train of AC bursts, and
  wherein the prosthetic aortic valve comprises a passive diode, which is coupled in electrical communication with the prosthetic-valve coil, and is configured to rectify current in the prosthetic-valve coil.

Inventive Concept 224. The valve prosthesis system according to Inventive Concept 223, wherein the external-unit control circuitry is configured to generate the train of AC bursts at a frequency of between 12 and 20 MHz.

Inventive Concept 225. The valve prosthesis system according to Inventive Concept 223, wherein the external-unit control circuitry is configured to include 20-100 AC bursts in each of the AC pulses.

There is additionally provided, in accordance with an Inventive Concept 226 of the present invention, a method comprising:
  delivering, to a native aortic valve of a patient, via vasculature of the patient, a prosthetic aortic valve while in a constrained delivery configuration within a delivery sheath, the prosthetic aortic valve including (a) a frame, which comprises interconnected stent struts arranged so as to define interconnected stent cells, (b) a plurality of prosthetic leaflets coupled to the frame, (c) a cathode and an anode, which are mechanically coupled to the frame, and (d) a prosthetic-valve coil, which is in non-wireless electrical communication with the cathode and the anode, and is coupled to a plurality of the stent struts, running along the stent struts; and
  releasing the prosthetic aortic valve from the delivery sheath, such that the prosthetic aortic valve transitions to an expanded fully-deployed configuration, in which the prosthetic-valve coil surrounds a plurality of the stent cells.

Inventive Concept 227. The method according to Inventive Concept 226, further comprising rotationally orienting the prosthetic aortic valve such that the prosthetic-valve coil faces generally anterio-superiorly toward a sternum of the patient.

Inventive Concept 228. The method according to Inventive Concept 227,
  wherein when the prosthetic aortic valve is in the expanded fully-deployed configuration, (a) a centroid of the prosthetic-valve coil and (b) a centroid of the cathode are rotationally offset from each other about a central longitudinal axis by an angle of at least 150 degrees when the prosthetic aortic valve is in the expanded fully-deployed configuration, the central longitudinal axis defined by the frame when the prosthetic aortic valve is in the expanded fully-deployed configuration, and
  wherein rotationally orienting the prosthetic aortic valve comprises aligning the cathode adjacent to cardiac tissue near a bundle of His of the patient, so as to automatically align the prosthetic-valve coil facing generally anterio-superiorly toward a sternum of the patient.

Inventive Concept 229. The method according to Inventive Concept 226, further comprising activating external-unit control circuitry of an external unit, disposed outside a body of the patient, to drive an energy-transmission coil of the external unit to wirelessly transfer energy to the prosthetic-valve coil by inductive coupling.

Inventive Concept 230. The method according to Inventive Concept 229, further comprising positioning the energy-transmission coil against a chest of the patient, over a sternum of the patient.

Inventive Concept 231. The method according to Inventive Concept 229, further comprising positioning the energy-transmission coil around a neck of the patient.

Inventive Concept 232. The method according to Inventive Concept 229, wherein activating the external-unit control circuitry comprises activating the external-unit control circuitry to drive the cathode and the anode to apply a pacing signal to a heart of the patient, by wirelessly transferring the energy from the energy-transmission coil to the prosthetic-valve coil by inductive coupling.

The present invention will be more fully understood from the following detailed description of embodiments thereof, taken together with the drawings, in which:

BRIEF DESCRIPTION OF THE DRAWINGS

FIGS. 14A-C are schematic illustrations of respective configurations of another prosthetic aortic valve, in accordance with respective applications of the present invention.

DETAILED DESCRIPTION OF APPLICATIONS

Figure 1A:
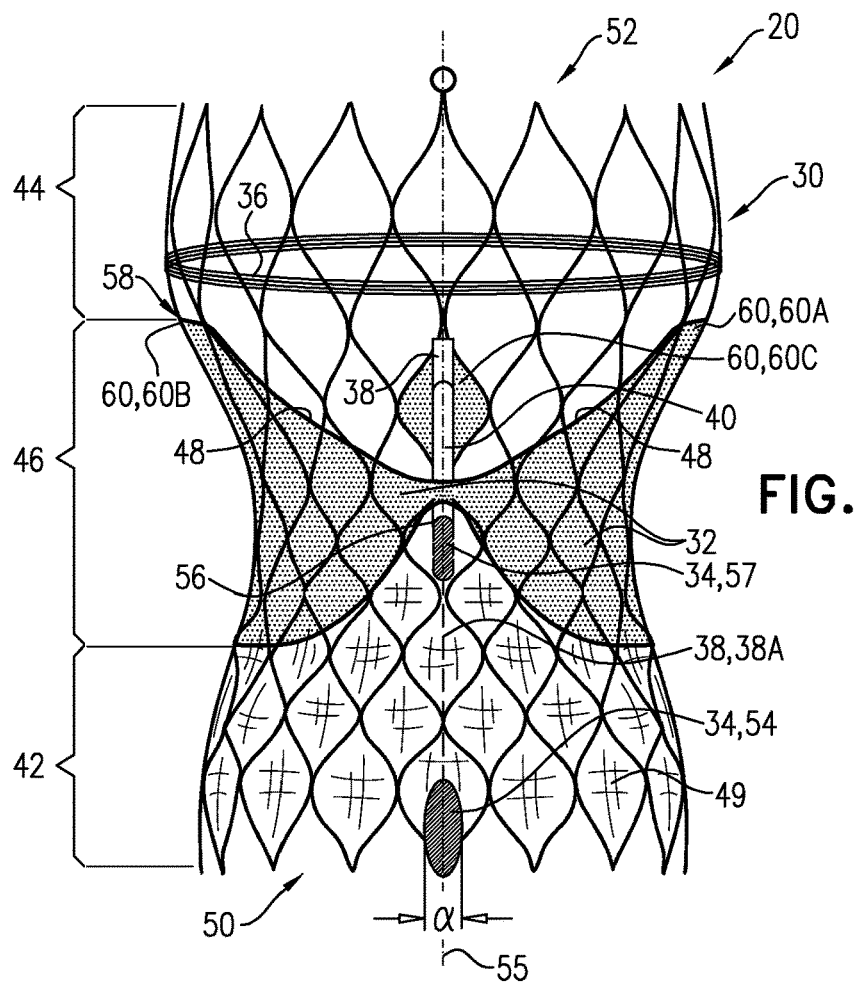
FIGS. 1A and 1B are schematic illustrations of a prosthetic aortic valve, in accordance with an application of the present invention.
Figure 1B:
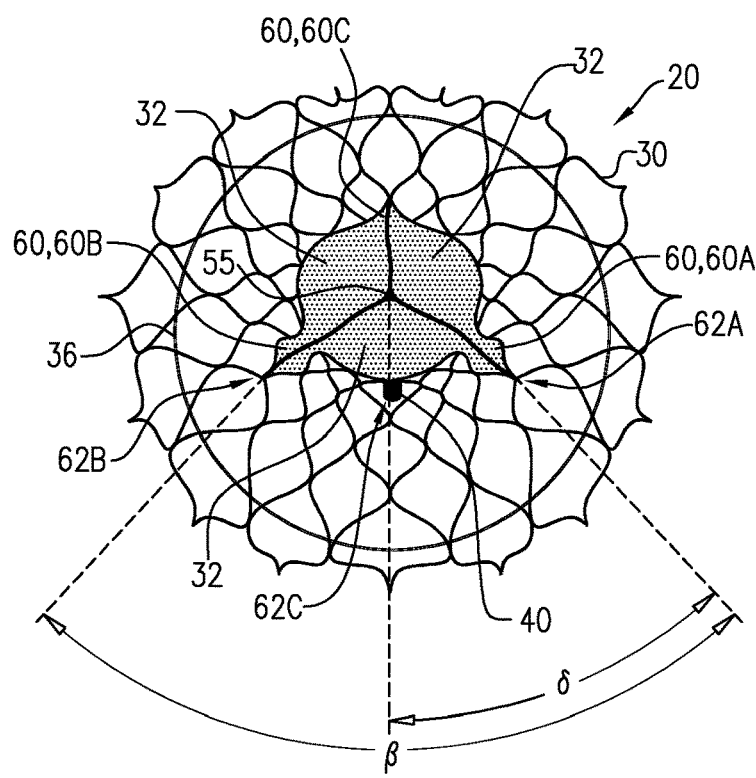

FIGS. 1A and 1B are schematic illustrations of a prosthetic aortic valve 20, in accordance with an application of the present invention. Prosthetic aortic valve 20 is shown in FIGS. 1A-B in an expanded configuration, which is similar to the expanded fully-deployed configuration described hereinbelow with reference to FIG. 4C, except that in FIGS. 1A-B expansion of prosthetic aortic valve 20 is not limited by anatomy of a patient. FIG. 1B is a view of prosthetic aortic valve 20 from a downstream outflow end 52, as described hereinbelow.

Prosthetic aortic valve 20 comprises:
- a frame 30;
- a plurality of prosthetic leaflets 32 coupled to frame 30;
- one or more electrodes 34 coupled to frame 30; and
- a prosthetic-valve coil 36 coupled to frame 30 and in non-wireless electrical communication with the one or more electrodes 34, optionally by one or more elongate insulated electrical conductors 38, e.g., wires.

Frame 30 typically comprises a stent or other structure, which is typically self-expanding, and may be formed by laser cutting or etching a metal alloy tube comprising, for example, stainless steel or a shape memory material such as Nitinol. For some applications, one or more of electrodes 34 are coupled to frame 30 using techniques described in U.S. Pat. No. 9,526,637 to Dagan et al. and/or US 2016/0278951 to Dagan et al., both of which are incorporated herein by reference. For some applications, prosthetic-valve coil 36 comprises gold wire, in order to provide low resistance.

For some applications, prosthetic aortic valve 20 further comprises prosthetic-aortic-valve control circuitry 40, which is coupled to frame 30 and which is in non-wireless electrical communication with the one or more electrodes 34. In these applications, prosthetic-valve coil 36 is in non-wireless electrical communication with prosthetic-aortic-valve control circuitry 40, such that prosthetic-valve coil 36 is in non-wireless electrical communication with the one or more electrodes 34 via prosthetic-aortic-valve control circuitry 40. One or more of the one or more electrodes 34 may be directly attached in non-wireless electrical communication to prosthetic-aortic-valve control circuitry 40, and/or may be attached in non-wireless electrical communication to prosthetic-aortic-valve control circuitry 40 by the one or more elongate insulated electrical conductors 38. Typically, prosthetic-aortic-valve control circuitry 40 is flexible, and has a thin, linear packaging, and may implement techniques described hereinbelow with reference to FIG. 5. The thinness of control circuitry 40 allows it to be compressed in a delivery tube during deployment of prosthetic aortic valve 20, without the need to increase the diameter of the delivery tube. In addition, the flexibility of control circuitry 40 prevents damage to the control circuitry when it is crimped when compressed into the delivery tube.

For some applications, frame 30 is shaped so as to define an upstream inflow portion 42, a downstream outflow portion 44, and a constriction portion 46, which is axially between upstream inflow portion 42 and downstream outflow portion 44. Prosthetic leaflets 32 are coupled to constriction portion 46 such that free edges 48 of prosthetic leaflets 32 face toward downstream outflow portion 44 when prosthetic aortic valve 20 is in the expanded fully-deployed configuration described hereinbelow with reference to FIG. 4C. Prosthetic leaflets 32 are not coupled to downstream outflow portion 44; therefore, a ring-shaped longitudinal border 58 between downstream outflow portion 44 and constriction portion 46 is defined by a downstream-most point of frame 30 to which prosthetic leaflets 32 are coupled (for example, prosthetic leaflets 32 may be coupled to the downstream-most point of frame 30 at commissures 60, described immediately hereinbelow). (Ring-shaped longitudinal border 58 is at the same longitudinal location around frame 30.) Typically, prosthetic aortic valve 20 further comprises a skirt 49 coupled to upstream inflow portion 42 of frame 30, and prosthetic leaflets 32 are attached along their bases to skirt 49, for example, using sutures or a suitable biocompatible adhesive. Adjoining pairs of leaflets are attached to one another at their lateral ends to form commissures 60, with free edges 48 of the prosthetic leaflets forming coaptation edges that meet one another. Skirt 49 and prosthetic leaflets 32 typically comprise a sheet of animal pericardial tissue, such as porcine pericardial tissue, or synthetic or polymeric material.

For some applications, prosthetic-valve coil 36 is disposed no more than 1 mm upstream of ring-shaped longitudinal border 58 between downstream outflow portion 44 and constriction portion 46, typically axially along downstream outflow portion 44. Such placement allows prosthetic aortic valve 20 to be crimped (compressed) into a delivery tube during deployment of prosthetic aortic valve 20, without requiring a larger-diameter delivery tube to accommodate prosthetic-valve coil 36. This is possible because downstream outflow portion 44 does not include material of prosthetic leaflets 32, and thus can accommodate prosthetic-valve coil 36 without causing downstream outflow portion 44 to have a greater compressed diameter than the other axial portions of prosthetic aortic valve 20. Typically, prosthetic-valve coil 36 is not disposed axially along constriction portion 46 and is not disposed axially along upstream inflow portion 42. In addition, placement of prosthetic-valve coil 36 axially along downstream outflow portion 44 improves transmission efficiency because downstream outflow portion 44 typically has a greater diameter than each of constriction portion 46 and upstream inflow portion 42. In addition, constriction portion 46 typically has a lesser diameter than each of upstream inflow portion 42 and downstream outflow portion 44.

Typically, at least one of the one or more electrodes 34 is coupled to upstream inflow portion 42 of frame 30, such as exactly one of the one or more electrodes 34. For some applications, the one or more electrodes 34 comprise a cathode 54 that is coupled to upstream inflow portion 42 of frame 30, and prosthetic-aortic-valve control circuitry 40 is configured to drive cathode 54 to apply a cathodic current. For some applications, cathode 54 has a lateral dimension a (alpha), measured in degrees around frame 30 with respect to a central longitudinal axis 55 of frame 30, of between 10 and 40 degrees, e.g., between 20 and 40 degrees, such as 30 degrees, in order to accommodate rotational misplacement of frame 30 with respect to the bundle of His. Typically, prosthetic aortic valve 20 is deployed using imaging, such as fluoroscopy, and is rotated if necessary during the deployment such that cathode 54 is disposed against tissue of the annulus that is near the bundle of His. For some applications, prosthetic aortic valve 20 comprises a plurality of cathodes 54 (e.g., two or three, or more), which are disposed at a respective plurality of angular locations around frame 30 (e.g., 10-15 degrees apart). After implantation of prosthetic aortic valve 20, the cathode 54 that is has the most accurate angular location is activated to apply a pacing signal and/or sense, either by prosthetic-aortic-valve control circuitry 40 or external control circuitry, such as external-unit control circuitry 104, described hereinbelow with reference to FIG. 4C. Alternatively or additionally, for some applications, cathode 54 has an axial length of at least 10 mm, in order to accommodate axial misplacement of frame 30 with respect to the annulus of the natural aortic valve, and thus with respect to the bundle of His. As used in the present application, including in the claims, an "axial length" is a length of a structure measured along central longitudinal axis 55.

For some applications, cathode 54 has a thickness of between 75 and 125 microns, e.g., about 100 microns, and/or a surface area of at least 2.5 mm2, in order to provide adequate stimulation. For some applications, cathode 54 comprises titanium nitride (TiN). For some applications, skirt 49 is coupled to an external surface of upstream inflow portion 42 of frame 30, and cathode 54 is disposed on an external surface of skirt 49. As used in the present application, including in the claims, the "central longitudinal axis" 55 of frame 30 is the set of all centroids of transverse cross-sectional sections of frame 30 along frame 30. Thus the cross-sectional sections are locally perpendicular to the central longitudinal axis, which runs along frame 30. (For applications in which frame 30 is circular in cross-section, the centroids correspond with the centers of the circular cross-sectional sections.)

For some applications, when prosthetic aortic valve 20 is in the expanded fully-deployed configuration described hereinbelow with reference to FIG. 4C:
frame 30 has an inflow end 50 at upstream inflow portion 42 and downstream outflow end 52 at downstream outflow portion 44, and an axial length, measured between inflow end 50 and downstream outflow end 52, and
at least one of (e.g., exactly one of, e.g., cathode 54) the one or more electrodes 34 is coupled to upstream inflow portion 42 within a distance from inflow end 50, the distance equal to 10% of the axial length of frame 30 (the distance is measured (a) along central longitudinal axis 55 of frame 30 when in the expanded fully-deployed configuration, and (b) between inflow end 50 and an upstream-most point of the at least one electrode).

Typically, prosthetic-aortic-valve control circuitry 40 is coupled to frame 30 such that upstream-most point 56 of prosthetic-aortic-valve control circuitry 40 is disposed axially along constriction portion 46 and/or downstream outflow portion 44 of frame 30.

Typically, prosthetic-aortic-valve control circuitry 40 is coupled to frame 30 inside frame 30, which may prevent friction between prosthetic-aortic-valve control circuitry 40 and delivery tube 72 during deployment of prosthetic aortic valve 20, described hereinbelow with reference to FIGS. 4A-C. It is noted that for applications in which upstream-most point 56 is disposed no more upstream than 1 mm upstream of ring-shaped longitudinal border 58, such as described above, there is generally enough space inside frame 30 to accommodate prosthetic-aortic-valve control circuitry 40.

For some applications, prosthetic leaflets 32 are coupled to frame 30 at at least first and second commissures 60A and 60B of prosthetic aortic valve 20 that are located at respective first and second angular locations 62A and 62B around frame 30. The first and second angular locations 62A and 62B are separated by a first angular offset β (beta) around frame 30 when prosthetic aortic valve 20 is in the expanded fully-deployed configuration described hereinbelow with reference to FIG. 4C. Prosthetic-aortic-valve control circuitry 40 is coupled to frame 30 at a third angular location 62C around frame 30 that is separated from first angular location 62A by a second angular offset δ (delta) that equals between 40% and 601% (e.g., 50%) of the first angular offset β (beta) when prosthetic aortic valve 20 is in the expanded fully-deployed configuration described hereinbelow with reference to FIG. 4C. At the third angular location 62C around frame 30, the frame is more flexible than at the more rigid commissures. As used in the present application, including in the claims, an "angular location" is a location on frame 30 at a particular location around central longitudinal axis 55, i.e., at a particular "o'clock" with respect to central longitudinal axis 55. (It is noted that a third commissure 60C is shown in FIG. 1A on the far side of the frame, i.e., 180 degrees from circuitry 40.)

Figure 2:
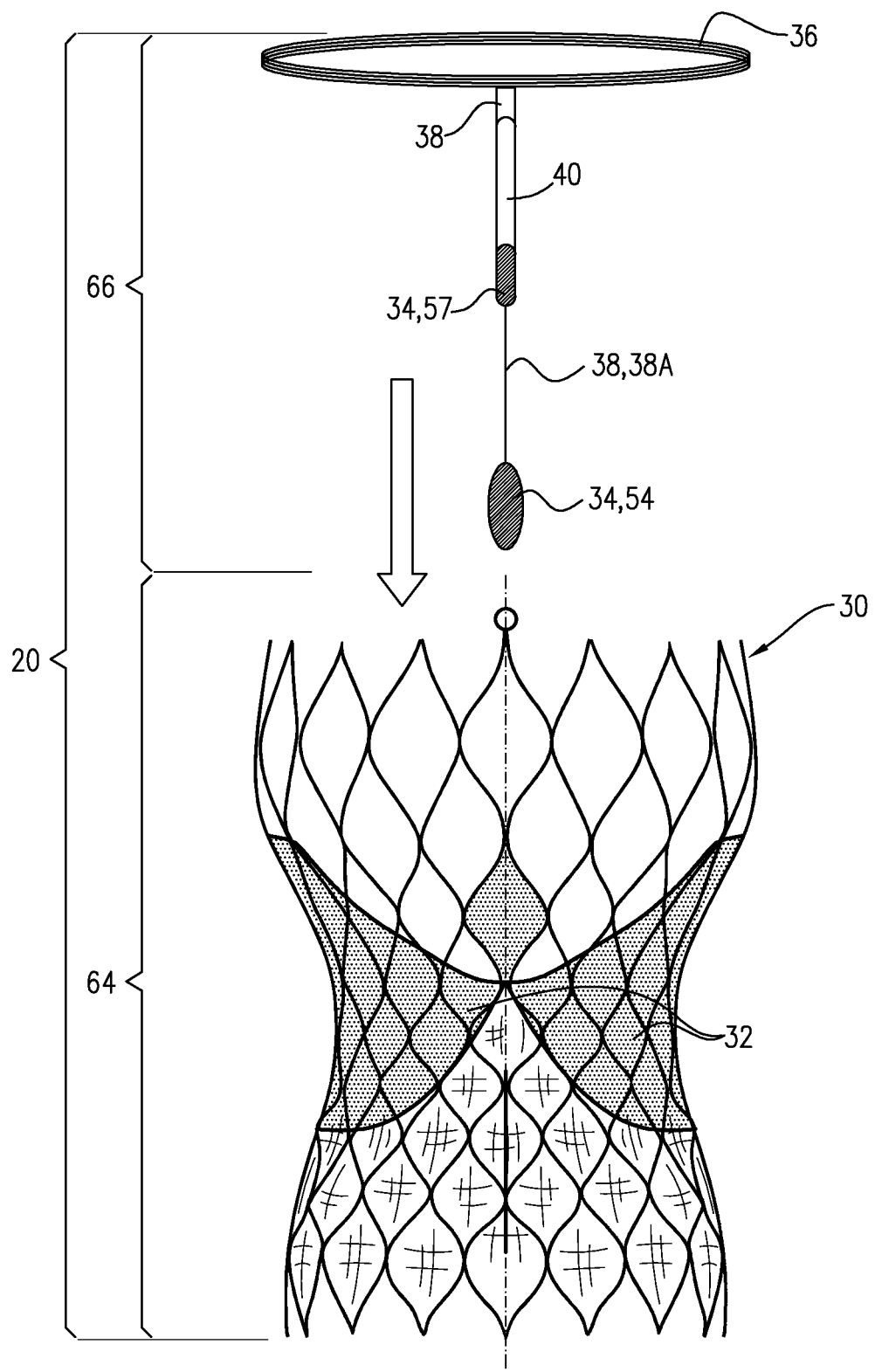
FIG. 2 is a schematic illustration of components of the prosthetic aortic valve of FIGS. 1A-B before complete assembly, in accordance with an application of the present invention.

Reference is now made to FIG. 2, which is a schematic illustration of components of prosthetic aortic valve 20 before complete assembly, in accordance with an application of the present invention. The components comprise a valve component 64 and an electronics component 66. Valve component 64 typically consists of a heart valve prosthesis known in the art, which comprises at least frame 30 and prosthetic leaflets 32. For example, the known heart valve prosthesis may comprise a CoreValve™ Evolut™ R prothesis (Medtronic, Inc., Minneapolis, Minn., USA), a CoreValve™ Evolut™ PRO prosthesis (Medtronic, Inc.), a LOTUS Edge™ Aortic Valve (Boston Scientific Corporation, Marlborough, Mass., USA), or an ACURATE Neo™ Aortic Valve (Boston Scientific Corporation). Electronics component 66 comprises at least the one or more electrodes 34 and prosthetic-valve coil 36, and optionally prosthetic-aortic-valve control circuitry 40.

During assembly of prosthetic aortic valve 20, electronics component 66 is inserted into valve component 64. For some applications, a first portion of electronics component 66, such as prosthetic-valve coil 36, prosthetic-aortic-valve control circuitry 40, and one of the one or more electrodes 34, is coupled to an inner surface of frame 30, and a second portion of electronics component 66, such as cathode 54, is coupled to an external surface of frame 30. For example, one 38A of one or more elongate insulated electrical conductors 38 may electrically couple cathode 54 to prosthetic-aortic-valve control circuitry 40, and the conductor 38A may pass from inside to outside frame 30, typically through skirt 49. (Coupling one of the one or more electrodes 34 to the inner surface of frame 30 may expose the electrode to blood of the subject upon implantation of the assembled prosthetic aortic valve 20. Coupling cathode 54 to the external surface of frame 30 may dispose the cathode against tissue, such as tissue of the annulus that is near the bundle of His, upon implantation of the assembled prosthetic aortic valve 20, such as described herein.) Optionally, the components of electronics component 66 may be stitched to frame 30 and/or skirt 49.

For some applications, whether prosthetic-valve coil 36 is coupled to an inner or an external surface of frame 30, prosthetic-valve coil 36 is electrically isolated from frame 30, such as by isolation material (e.g., a sheet of material or a coating) disposed between prosthetic-valve coil 36 and frame 30. For example, the isolation material may comprise a non-conductive polymer.

The above-mentioned assembly of prosthetic aortic valve 20 is typically performed in a manufacturing facility, and thereafter the assembled prosthetic aortic valve 20 is packaged and shipped to a healthcare facility for implantation. The method of assembling prosthetic aortic valve 20 is thus non-surgical.

Figure 3A:
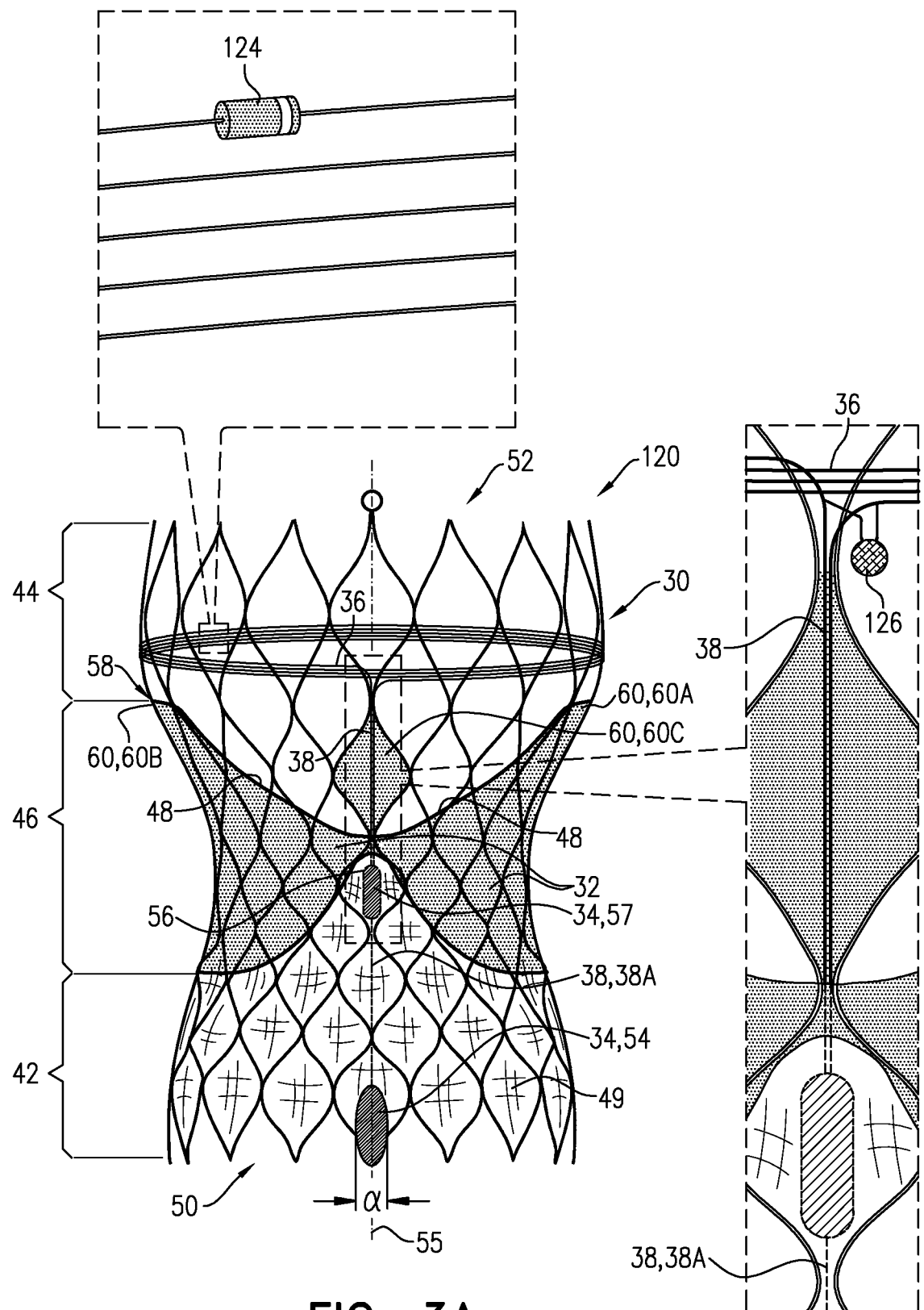
FIG. 3A is a schematic illustration of another prosthetic aortic valve, in accordance with an application of the present invention.

FIG. 3A is a schematic illustration of a prosthetic aortic valve 120, in accordance with an application of the present invention. Prosthetic aortic valve 120 is shown in FIG. 3A in an expanded configuration, which is similar to the expanded fully-deployed configuration of prosthetic aortic valve 20 described hereinbelow with reference to FIG. 4C, except that in FIG. 3A expansion of prosthetic aortic valve 120 is not limited by anatomy of a patient. Other than as described hereinbelow, prosthetic aortic valve 120 is identical to prosthetic aortic valve 20 described herein with reference to FIGS. 1A-B and 2, and like reference numerals refer to like parts. Prosthetic aortic valve 120 may be assembled as described hereinabove with reference to FIG. 2 for prosthetic aortic valve 20, mutatis mutandis.

Figure 3B:
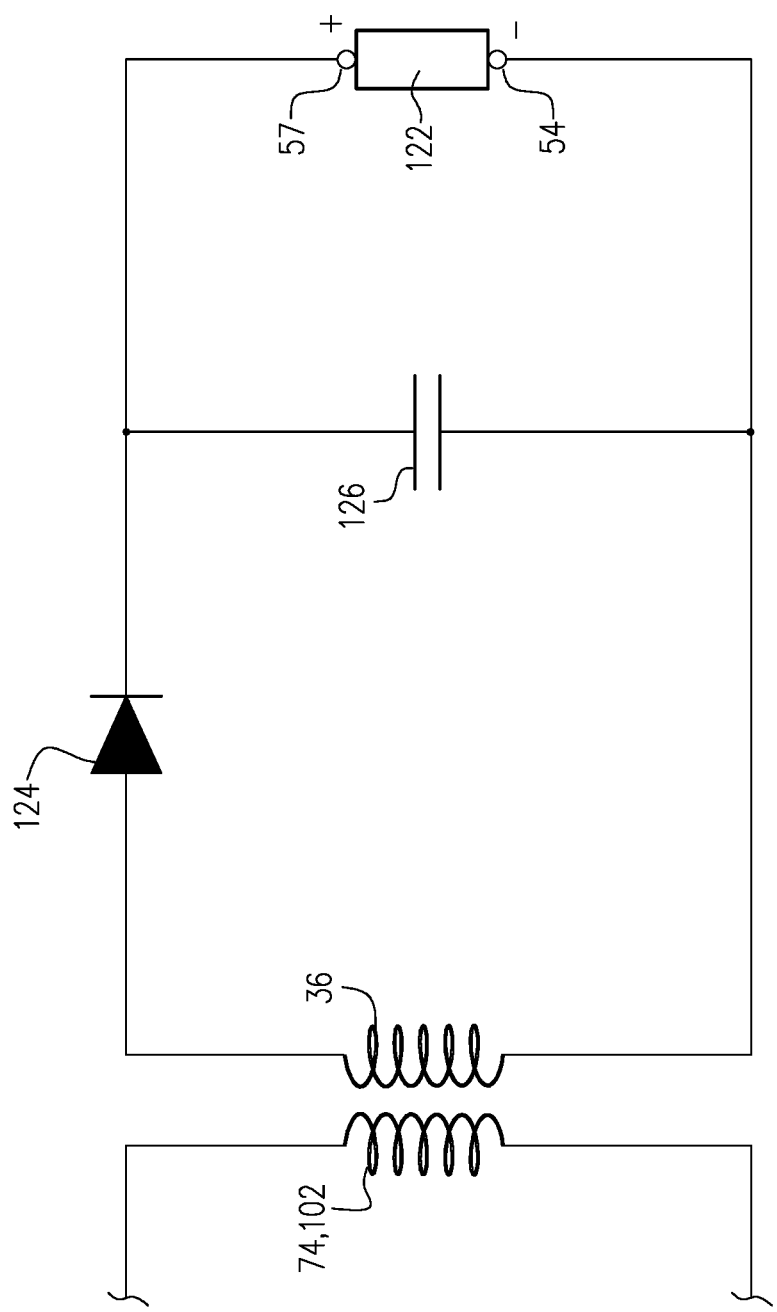
FIG. 3B is a schematic illustration of passive electrical components of the prosthetic aortic valve of FIG. 3A and cardiac tissue, in accordance with an application of the present invention.

Reference is also made to FIG. 3B, which is a schematic illustration of passive electrical components of prosthetic aortic valve 120 and tissue 122, in accordance with an application of the present invention. Tissue 122 includes cardiac tissue and blood. Cathode 54 is configured to be in contact with the cardiac tissue, and anode 57 is configured to be in contact with the blood. As is known in the art, cardiac tissue acts as a resistor.

For some applications, prosthetic aortic valve 120 comprises a passive diode 124 (shown highly schematically in the upper exploded view in FIG. 3A, as well as in FIG. 3B), which is coupled in electrical communication with prosthetic-valve coil 36 and rectifies current in the prosthetic-valve coil. For example, diode 124 may be positioned at one end of the coil or adjacent to cathode 54 or anode 57, or (as shown in FIG. 3A) at some point along prosthetic-valve coil 36. Non-implantable control circuitry (such as delivery-system control circuitry 80 (FIG. 4B) or external-unit control circuitry 104 (FIG. 4C)) typically wirelessly transfers energy to prosthetic-valve coil 36 by generating a plurality of AC pulses, each AC pulse including a train of AC bursts. The train of AC bursts may be generated, for example, at a frequency of between 3 kHz and 130 kHz (e.g., between 3 kHz and 100 kHz, or between 100 kHz and 130 kHz), or a frequency of between 12 and 20 MHz, such as between 13 and 20 MHz, e.g., 13.56 MHz, for improved efficiency. For some applications, there are 20-100 AC bursts in each of the AC pulses. Other frequencies and number of bursts are within the scope of the present invention. For some applications, non-implantable control circuitry (such as delivery-system control circuitry 80 (FIG. 4B) or external-unit control circuitry 104 (FIG. 4C)) is configured to wirelessly transfers, to prosthetic-valve coil 36, energy that generates between 5 and 10 V in prosthetic-valve coil 36.

For some applications, prosthetic aortic valve 120 comprises exactly one passive diode 124, which provides half-wave rectification of the AC pulses. For other applications, prosthetic aortic valve 120 comprises a plurality of passive diodes 124, which provide full-wave rectification of the AC pulses; for example, prosthetic aortic valve 120 may comprise four passive diodes 124 arranged in a bridge configuration, as is known in the electronics art.

For some applications, prosthetic aortic valve 120 comprises a capacitor 126 (shown highly schematically in the exploded view to the right in FIG. 3A, as well as in FIG. 3B), which is in electrical communication with cathode 54 and anode 57 (parallel to cardiac tissue 122 in the circuit made upon implantation of the electrodes). Capacitor 126 typically increases the efficiency of the circuit by delivering a larger proportion of the received energy into tissue 122. (As is known in the electronics art, a capacitor is a passive electrical component.)

Optionally, prosthetic aortic valve 120 comprises additional passive electrical components, such as one or more resistors.

As described hereinbelow with reference to FIG. 4B regarding prosthetic aortic valve 20, for some applications, delivery-system control circuitry 80 is configured to drive the one or more electrodes 34 to apply the rapid ventricular pacing; in this configuration, prosthetic-aortic-valve control circuitry 40, if even provided, is generally passive, i.e., delivery-system control circuitry 80 sets the parameters of the pacing signal. Prosthetic aortic valve 120, shown in FIG. 3A, is one implementation of this configuration; unlike the configuration of prosthetic aortic valve 20 illustrated in FIGS. 1A-B and 2, prosthetic aortic valve 120 does not comprise prosthetic-aortic-valve control circuitry 40 or any other active electronic components.

A valve prosthesis system is provided that comprises (a) prosthetic aortic valve 120 and (b) a non-implantable unit, such as delivery system 70, described hereinbelow with reference to FIGS. 4A-C, or external unit 100, described hereinbelow with reference to FIG. 4C. Non-implantable control circuitry (such as delivery-system control circuitry 80 or external-unit control circuitry 104 of external unit 100, as appropriate) is configured to drive cathode 54 and anode 57 to apply a pacing signal and to set parameters of the pacing signal (e.g., to be a standard, chronic pacing signal, or a rapid ventricular pacing signal), by wirelessly transferring energy from an energy-transmission coil (such as delivery-system coil 74 or external-unit coil 102, described hereinbelow with reference to FIG. 4C, as appropriate) to prosthetic-valve coil 36 by inductive coupling. The applied pacing is typically bipolar.

For some applications, the wireless transfer of energy by inductive coupling described herein utilizes resonant inductive wireless energy transfer, as is known in the art.

Optionally, the valve prosthesis system comprises two non-implantable units: (1) delivery system 70, described hereinbelow with reference to FIGS. 4A-C, and (2) external unit 100, described hereinbelow with reference to FIG. 4C, which comprise respective control circuitry and energy-transmission coils. Delivery-system control circuitry 80 is configured to drive delivery-system coil 74 to drive cathode 54 and anode 57 to apply the pacing signal and to set the parameters of the pacing signal, by wirelessly transferring energy, by inductive coupling, to prosthetic-valve coil 36 when prosthetic aortic valve 120 is in the partially-deployed configuration, such as described hereinbelow with reference to FIG. 4B. External-unit control circuitry 104 is configured to drive external-unit coil 102, described hereinbelow with reference to FIG. 4C, to drive cathode 54 and anode 57 to apply the pacing signal and to set the parameters of the pacing signal, by wirelessly transferring energy, by inductive coupling, to prosthetic-valve coil 36 when prosthetic aortic valve 120 is in the expanded fully-deployed configuration, such as described hereinbelow with reference to FIG. 4C.

Typically, respective ends of prosthetic-valve coil 36 are in the non-wireless electrical communication with cathode 54 and anode 57.

For some applications, respective non-electrically-insulated end portions of prosthetic-valve coil 36 define cathode 54 and anode 57. In these applications, prosthetic aortic valve 120 typically does not comprise elongate insulated electrical conductors 38. Instead, respective insulated end portions of prosthetic-valve coil 36 bend away from prosthetic-valve coil 36 along the paths of elongate insulated electrical conductors 38 shown in FIG. 3A, such that the respective non-electrically-insulated end portions of prosthetic-valve coil 36 are located at the locations at which cathode 54 and anode 57 are shown in FIG. 3A, respectively.

As mentioned above, the non-implantable control circuitry is configured to drive cathode 54 and anode 57 to set parameters of the pacing signal. For example, the non-implantable control circuitry may be configured to set an amplitude of the pacing signal by modulating an amplitude of the energy wirelessly transferred from the energy-transmission coil to prosthetic-valve coil 36. Alternatively or additionally, for example, the non-implantable control circuitry may be configured to drive cathode 54 and anode 57 to (a) begin application of each pulse of the pacing signal by beginning wirelessly transferring energy from the energy-transmission coil to prosthetic-valve coil 36, and (b) conclude the application of each pulse of the pacing signal by ceasing wirelessly transferring energy from the energy-transmission coil to prosthetic-valve coil 36.

The inventor has determined that, in some configurations, it is difficult to assess suitable pacing parameters, e.g., due to patient size or patient body mass distribution, or for example due to technical issues such as variable electrical impedance between heart tissue and cathode 54 and anode 57, or the variable relative orientation of external-unit coil 102 and prosthetic-valve coil 36. For some applications, therefore, the non-implantable unit comprises an energy-transmission coil (e.g., external-unit coil 102, as shown in FIG. 4C), and at least two sensing skin ECG electrodes 106, placed on the patient's skin 108, e.g., on the chest as shown in FIG. 4C. The non-implantable control circuitry (e.g., external-unit control circuitry 104) drives cathode 54 and anode 57 to apply a pacing signal to the patient's heart, and to detect at least one cardiac parameter using sensing skin ECG electrodes 106. The non-implantable control circuitry, at least partially responsively to the detected cardiac parameter, sets parameters of the pacing signal, by wirelessly transferring energy from the energy-transmission coil to prosthetic-valve coil 36 by inductive coupling. Because prosthetic aortic valve 120 typically does not comprise any active electronic components, the wireless transfer of energy from the energy-transmission coil to prosthetic-valve coil 36 by inductive coupling itself inductively drives the pacing current through prosthetic-valve coil 36.

Alternatively, the non-implantable unit comprises another type of cardiac sensor, instead of sensing skin ECG electrodes 106. For example, the cardiac sensor may comprise a heart rate sensor, such as an optical heart rate sensor (e.g., which uses photoplethysmography), or an ECG sensor, such as an optical ECG sensor (e.g., a single channel ECG sensor, such as the Si1172 or Si1173 biometric modules, manufactured by Silicon Laboratories Inc., Austin, Tex., USA).

The non-implantable control circuitry typically analyzes the detected cardiac parameter to assess a level of responsiveness of the heart to the pacing signal. Upon ascertaining that the level of responsiveness is unsatisfactory, the non-implantable control circuitry increases the strength of the pacing signal responsively to the detected cardiac parameter (e.g., by increasing the amplitude or the duration of the pacing signal). For example, the pulse width (typically 0.1-1 ms, e.g., 0.25-0.8 ms) of pulses of the pacing signal, or current amplitude in the energy-transmission coil may be iteratively increased, until a determination is made that the heart is suitably responding to the pacing pulses applied to the tissue. At this point, optionally, the strength of the pacing signal is further increased, e.g., by 50-150%, for example by 100%.

For some applications, the detected cardiac parameter is a timing feature of cardiac activity (e.g., heart rate, or the timing of a particular feature of the cardiac cycle). In this case, the parameters of the pacing signal may include a timing parameter of the pacing signal, and the non-implantable control circuitry sets the timing parameter of the pacing signal responsively to the timing feature of the detected cardiac parameter.

It is noted that, as appropriate for a given patient, pacing of the heart may be applied in a manner that is synchronized to the cardiac cycle of the patient (based on the signals received by sensing skin ECG electrodes 106), or the pacing may not be synchronized with the cardiac cycle of the patient.

Sensing skin ECG electrodes 106 are typically suction ECG electrodes or configured to be electrically coupled to the skin by an adhesive. In general, conventional ECG electrodes are suitable to be used for sensing skin ECG electrodes 106. It is noted that although conventional ECG electrodes may be used, complete ECG analysis as is known in the field of electrocardiography typically is not performed in order to implement the functions of the non-implantable control circuitry described hereinabove.

Figure 4A:
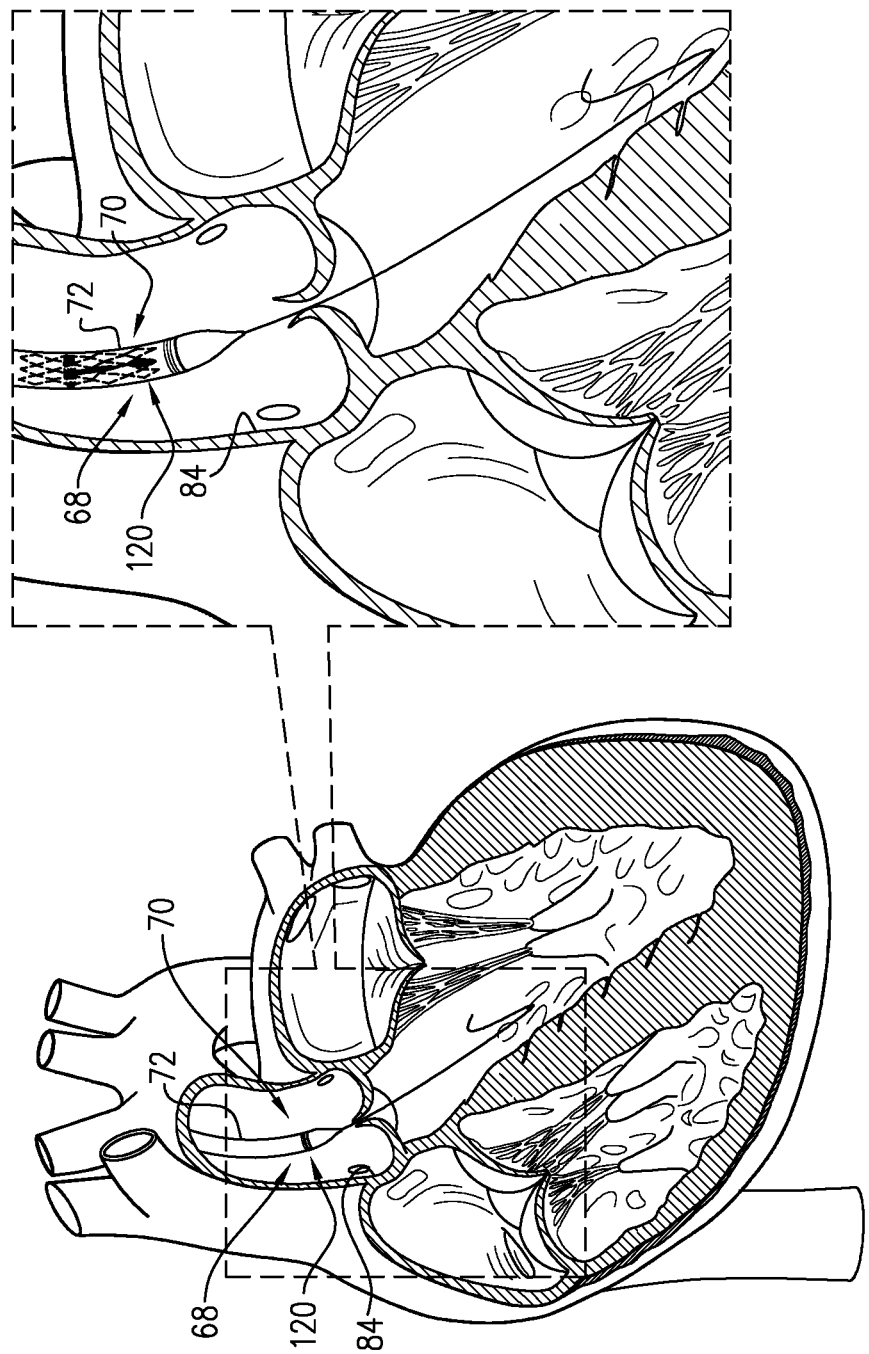
FIGS. 4A-C are schematic illustrations of a valve prosthesis system and a method of using the system, in accordance with respective applications of the present invention.
Figure 4B:
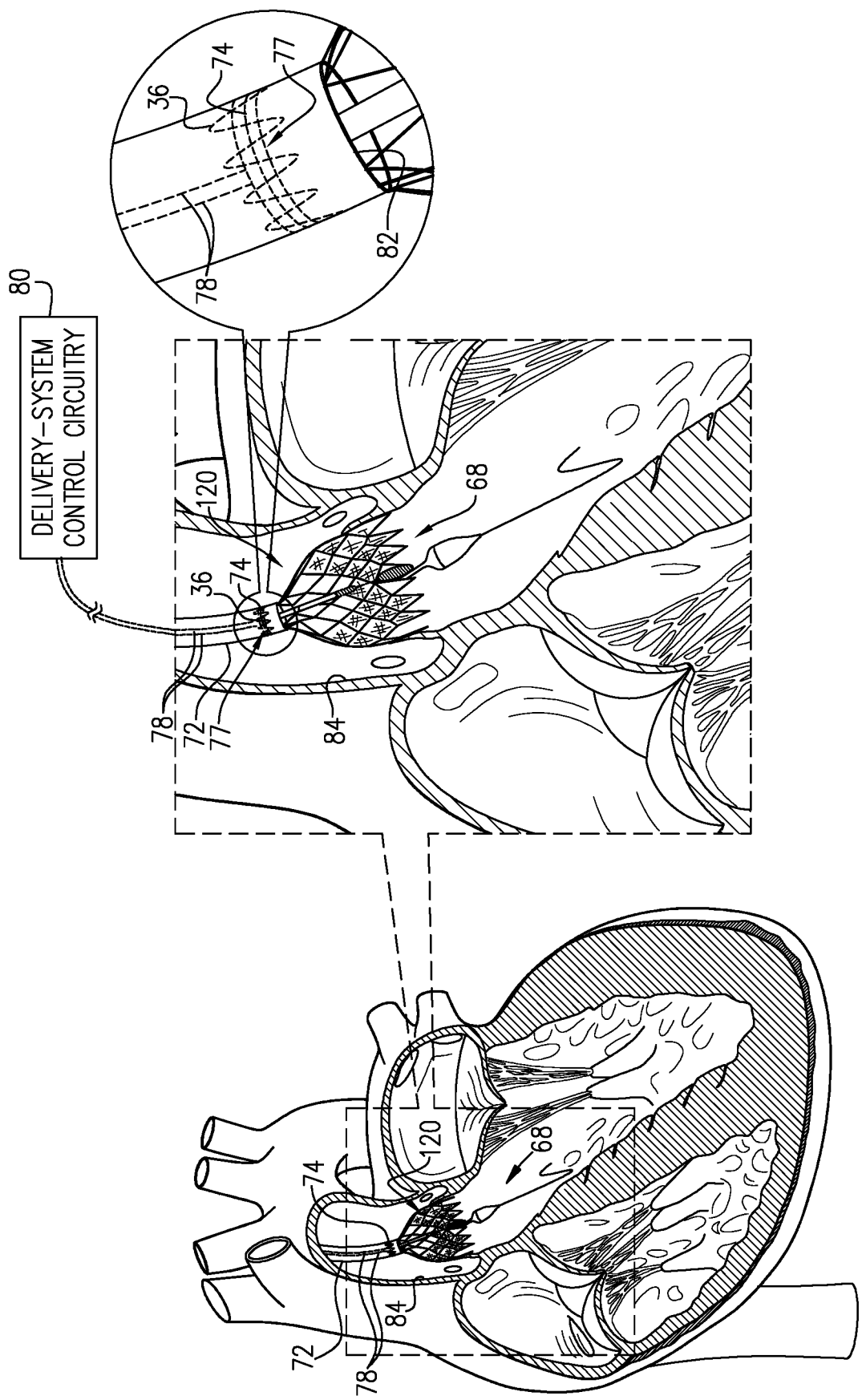
Figure 4C:
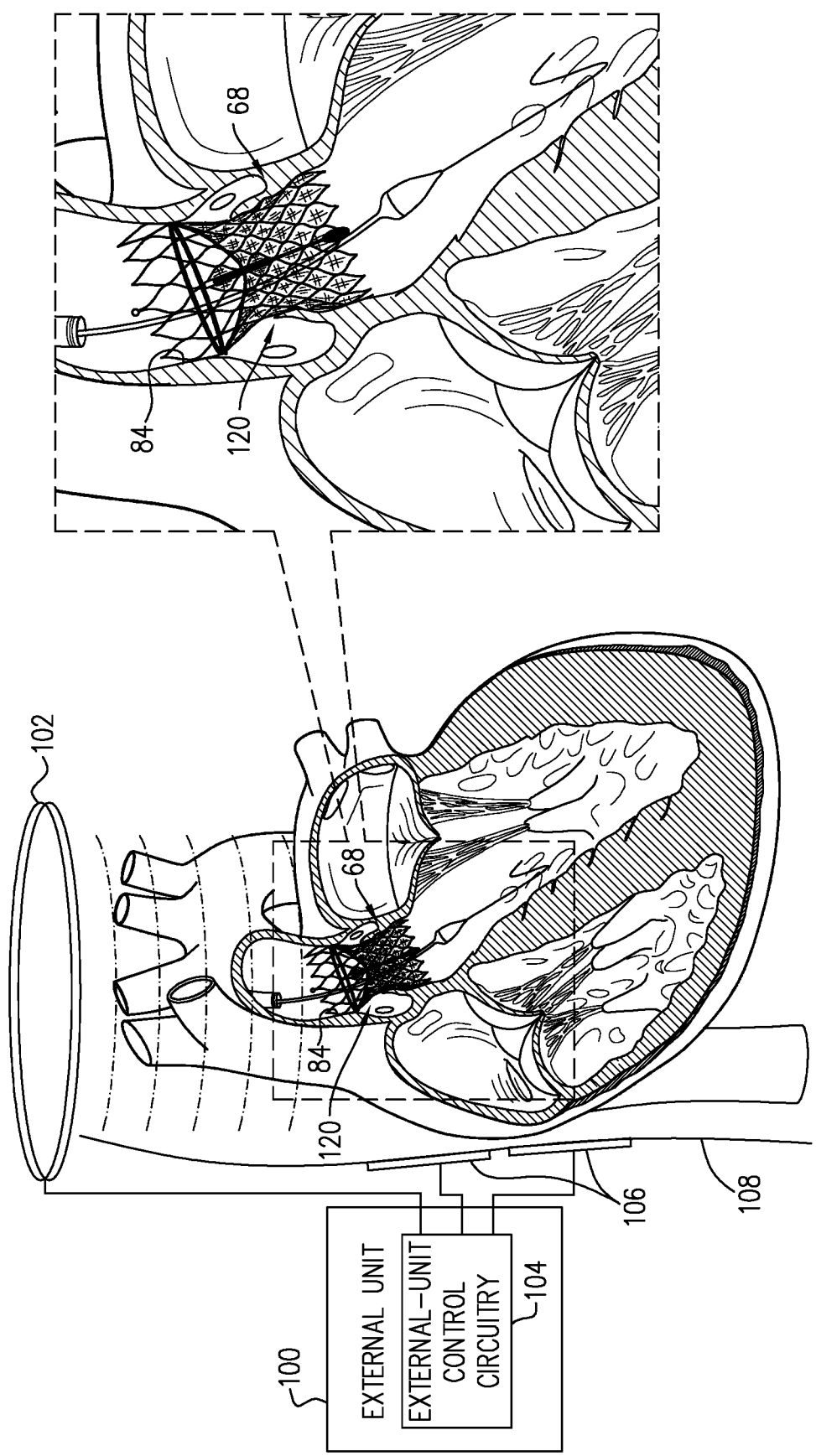

Reference is made to FIGS. 1A-B, 2, and 3A, and is additionally made to FIGS. 4A-C, which are schematic illustrations of a valve prosthesis system 68 and a method of using the system, in accordance with respective applications of the present invention. Although the techniques described with reference to FIGS. 4A-C are generally described regarding prosthetic aortic valve 120, the techniques are equally applicable to prosthetic aortic valve 20, mutatis mutandis. The rotational orientation of the prosthetic aortic valve is shown schematically in FIGS. 4A-C, in order to illustrate the components of the prosthetic aortic valve; as described below, in actual use, the prosthetic aortic valve is typically rotationally oriented such that cathode 54 is positioned adjacent to cardiac tissue near the bundle of His.

Valve prosthesis system 68 comprises prosthetic aortic valve 20 or prosthetic aortic valve 120 and a delivery system 70.

Delivery system 70 comprises:
a delivery tube 72;
a delivery-system coil 74, which is coupled to delivery tube 72 at a distal site 76 of delivery tube 72; for example, a distal-most portion 77 of delivery-system coil 74 may be disposed within 10 mm of a distal end 82 of delivery tube 72;
one or more wires 78, which pass along delivery tube 72, e.g., attached to an outer or inner surface of delivery tube 72, or embedded in the wall of delivery tube 72; and
delivery-system control circuitry 80, which is in electrical communication with delivery-system coil 74 via the one or more wires 78.

Delivery-system control circuitry 80 is configured to drive delivery-system coil 74 to wirelessly transfer energy, by inductive coupling, to prosthetic-valve coil 36 at least when prosthetic aortic valve 120 is in the partially-deployed configuration described hereinbelow with reference to FIG. 4B.

As shown in FIG. 4A, prosthetic aortic valve 120 is removably disposable in delivery tube 72 in a compressed delivery configuration. During an implantation procedure, delivery tube 72 is advanced through vasculature of a patient, until distal end 82 of delivery tube 72 is disposed in an ascending aorta 84 of the patient, while prosthetic aortic valve 120 is removably disposed in delivery tube 72 in the compressed delivery configuration.

As shown in FIG. 4B, prosthetic aortic valve 120 is also configured to assume a partially-expanded partially-deployed configuration upon being partially released from distal end 82 of delivery tube 72 such that (a) at least one of the one or more electrodes 34 is positioned outside delivery tube 72, such as cathode 54, in the vicinity of (e.g., touching) target tissue, such as the natural aortic valve annulus, and (b) prosthetic-valve coil 36 is compressed within delivery tube 72. Typically, delivery-system coil 74 surrounds compressed prosthetic-valve coil 36, which provides high transmission efficiency even though prosthetic-valve coil 36 is still compressed. After prosthetic aortic valve 120 has assumed the partially-expanded partially-deployed configuration, delivery-system control circuitry 80 is activated to drive delivery-system coil 74 to wirelessly transfer energy, by inductive coupling, to prosthetic-valve coil 36. By contrast, transmission of power from an external coil to compressed prosthetic-valve coil 36 would be quite inefficient because of the greater distance between the transmitting and receiving coils and the compression of prosthetic-valve coil 36.

For some applications in which valve prosthesis system 68 comprises prosthetic aortic valve 20, described hereinabove with reference to FIGS. 1A-B and 2, prosthetic-aortic-valve control circuitry 40 is configured to drive the one or more electrodes 34 to apply rapid ventricular pacing. Such pacing may temporarily reduce left ventricular output, in order to enable more accurate placement of prosthetic aortic valve 20. Alternatively, such as described hereinabove with reference to FIG. 3A, delivery-system control circuitry 80 is configured to drive the one or more electrodes 34 to apply the rapid ventricular pacing; in this configuration, prosthetic-aortic-valve control circuitry 40, if even provided (as in prosthetic aortic valve 20), is generally passive, or prosthetic-aortic-valve control circuitry 40 is not provided (as in prosthetic aortic valve 120), i.e., delivery-system control circuitry 80 sets the parameters of the pacing signal. Alternatively, prosthetic aortic valve 20 or 120 is not used for applying rapid ventricular pacing, and may instead be used for applying pacing post-implantation, such as described below, and/or for post-implantation sensing, such as described below.

As described hereinabove with reference to FIGS. 1A-B, for some applications, the one or more electrodes 34 comprise cathode 54 that is coupled to upstream inflow portion 42 of frame 30. When prosthetic aortic valve 120 is in the partially-expanded partially-deployed configuration shown in FIG. 4B, cathode 54 is positioned adjacent to cardiac tissue near the bundle of His, in order to pace the heart by stimulating the cardiac tissue with cathodic current. For some applications, the one or more electrodes further comprise an anode 57, which may be used for bipolar sensing and/or pacing, as known in the art. Typically, cathode 54 and anode 57 are disposed on frame 30 such that there is at least 15 mm between the cathode and the anode, when prosthetic aortic valve 120 is in the expanded fully-deployed configuration described hereinbelow with reference to FIG. 4C (the 15 mm is measured along central longitudinal axis 55 of frame 30 when in the expanded fully-deployed configuration).

As shown in FIG. 4C, prosthetic aortic valve 120 is also configured to assume an expanded fully-deployed configuration upon being fully released from distal end 82 of delivery tube 72. For some applications, delivery-system control circuitry 80 is configured to cease driving delivery-system coil 74 to wirelessly transfer the energy when prosthetic aortic valve 120 assumes the expanded fully-deployed configuration upon being fully released from distal end 82 of delivery tube 72.

For some applications, as shown in FIG. 4C, valve prosthesis system 68 further comprises an external unit 100, which comprises (a) an external-unit coil 102, and (b) external-unit control circuitry 104, which is configured to drive external-unit coil 102 to wirelessly transfer energy, by inductive coupling, to prosthetic-valve coil 36 when prosthetic aortic valve 120 is in the expanded fully-deployed configuration. In these applications, after prosthetic aortic valve 120 is fully released from distal end 82 of delivery tube 72, external-unit control circuitry 104 is activated to drive external-unit coil 102 to wirelessly transfer energy, by inductive coupling, to prosthetic-valve coil 36 when prosthetic aortic valve 120 is in the expanded fully-deployed configuration.

For some applications, external-unit coil 102 is incorporated into a collar configured to be worn around the patient's neck or placed on the patient's chest, such as described in PCT Publication WO 2016/157183 to Dagan et al., which is incorporated herein by reference, and/or incorporated into a band configured to be worn around the patient's chest or a necklace configured to be worn around the patient's neck. This positioning of external-unit coil 102 provides high transmission efficiency, because the respective axes of external-unit coil 102 and prosthetic-valve coil 36 are generally aligned.

Alternatively or additionally, for some applications, external unit 100 is incorporated into a belt or strap configured to be worn around the patient's chest.

For some applications in which valve prosthesis system 68 comprises prosthetic aortic valve 20, described hereinabove with reference to FIGS. 1A-B and 2, prosthetic-aortic-valve control circuitry 40 is configured to use the received energy to drive the one or more electrodes 34 to perform pacing post-implantation, e.g., for several months. Such pacing may employ any standard pacing protocol. For some applications, the pacing is VVI pacing, which is only applied when a QRS complex is not sensed in the ventricle. Alternatively, for some applications in which valve prosthesis system 68 comprises prosthetic aortic valve 120, described hereinabove with reference to FIG. 3A, external-unit control circuitry 104 is configured to drive the one or more electrodes 34 to apply the pacing signal; in this configuration, prosthetic-aortic-valve control circuitry 40 is not provided (or if provided, is generally passive), i.e., external-unit control circuitry 104 sets the parameters of the pacing signal.

Alternatively, for some applications in which valve prosthesis system 68 comprises prosthetic aortic valve 20, described hereinabove with reference to FIGS. 1A-B and 2, prosthetic-aortic-valve control circuitry 40 is configured to (a) use the one or more electrodes 34 to sense a cardiac signal, and (b) drive prosthetic-valve coil 36 to transmit a wireless signal indicative of the sensed cardiac signal. For some applications, the cardiac sensing is performed using techniques described in U.S. Pat. No. 9,005,106 to Gross et al., which is incorporated herein by reference. In these applications, the one or more electrodes 34 are typically not used to apply pacing, any thus need not be configured as a cathode and an anode. Such sensing may enable early discharge of the patient from the hospital after implantation of prosthetic aortic valve 20, before the possible development of left bundle branch block (LBBB). If LBBB develops, as it does in approximately 20-30% of patients, the LBBB is detected by the sensing, an alert is generated, and the LBBB may be treated as appropriate.

Figure 5:
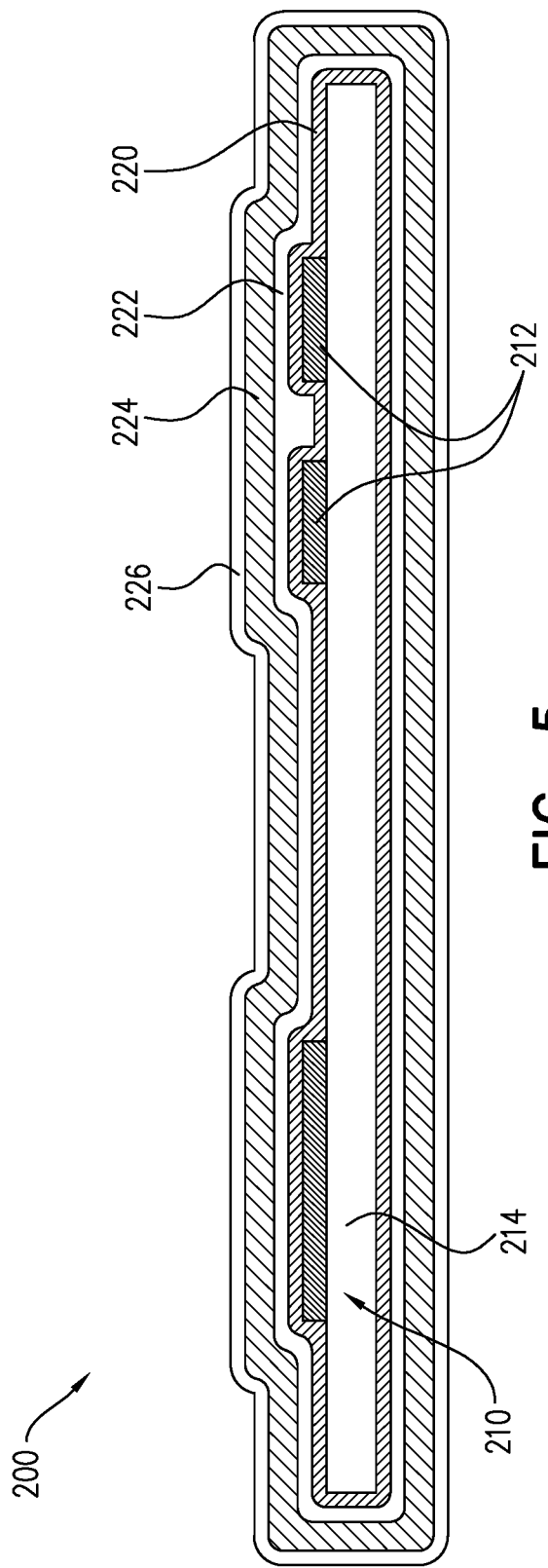
FIG. 5 is a schematic illustration of an electronic implant, in accordance with an application of the present invention.

Reference is now made to FIG. 5, which is a schematic illustration of an electronic implant 200, in accordance with an application of the present invention. Prosthetic-aortic-valve control circuitry 40, described hereinabove with reference to FIGS. 1A-2, may implement features of electronic implant 200.

Electronic implant 200 comprises circuitry 210, which comprises electronic components 212, typically mounted on a long and flexible printed circuit board (PCB) 214. Electronic implant 200 further comprises a multi-layer protective coating, which comprises the following layers in the following order:

- a first inner aluminum oxide (AlOx) film layer 220 deposited on circuitry 210, e.g., using atomic layer deposition (ALD);
- a second parylene layer 222 deposited (typically, vapor-deposited in a vacuum) on first inner AlOx film layer 220; second parylene layer 222 provides chemical protection for circuitry 210;
- optionally, a third layer 224 disposed (typically cast onto) on second parylene layer 222, the third layer, for example, comprising a polymer, such as a polymer selected from the group consisting of: silicone and PTFE; third layer 224 typically has a thickness of between 100 and 200 microns, and is configured to provide mechanical protection for circuitry 210; and
- optionally, a fourth outer parylene layer 226 deposited (typically, vapor-deposited in a vacuum) on third layer 224; fourth outer parylene layer 226 provides chemical protection for circuitry 210 and third layer 224.

Electronic implant 200 and the layers are drawn highly schematically in FIG. 5, and are not drawn to scale; in particular, the layers are actually much thinner than shown, and the relative thicknesses are different from those shown.

Typically, circuitry 210 is not encased in a case, but is only coated with layers, as described above. A "case" is an enclosure, typically comprising glass and/or metal, that has a structure before circuitry is disposed therein; by contrast, a coating takes the shape of the circuitry to which the coating is applied. By contrast, encasement in a case is standard in the field of implantable circuitry. The lack of such a case allows electronic implant 200 to be thin and flexible, with the tradeoff of shorter lifespan. For prosthetic-aortic-valve control circuitry 40, the shorter lifespan is generally not an issue, because prosthetic-aortic-valve control circuitry 40 is typically only used for several months.

For applications in which prosthetic-aortic-valve control circuitry 40 implements features of electronic implant 200, the one or more electrodes 34 are masked during application of the coatings. Thus, prosthetic-aortic-valve control circuitry 40, the one or more elongate insulated electrical conductors 38 (e.g., wires), and prosthetic-valve coil 36 are all coated in the same coating procedure.

Figure 6:
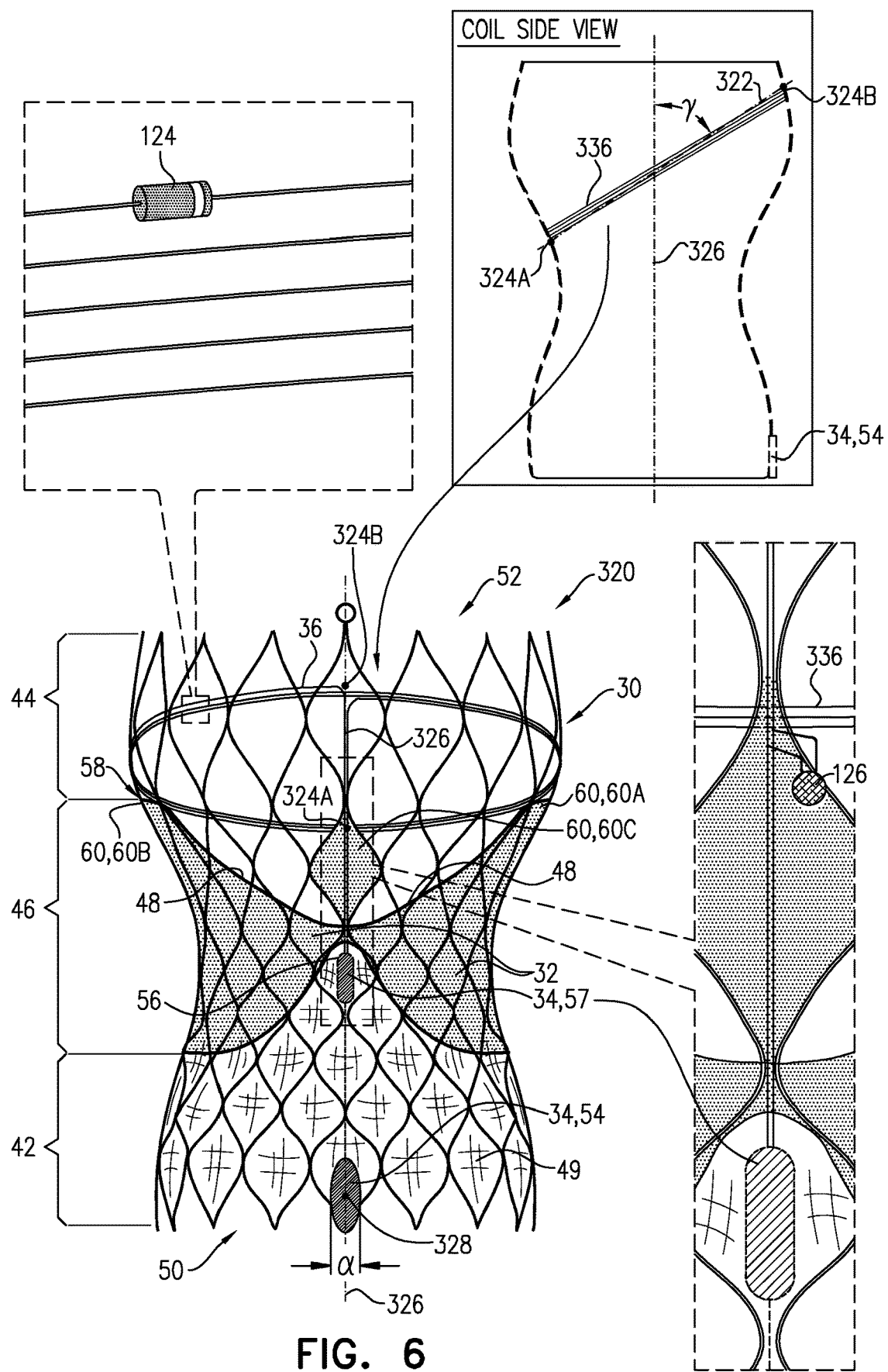
FIG. 6 is a schematic illustration of a prosthetic aortic valve, in accordance with an application of the present invention.

Reference is now made to FIG. 6, which is a schematic illustration of a prosthetic aortic valve 320, in accordance with an application of the present invention. Other than as described hereinbelow, prosthetic aortic valve 320 is generally similar to prosthetic aortic valve 120, described hereinabove with reference to FIGS. 3A-B, and may implement any of the features thereof, mutatis mutandis.

Figure 7:
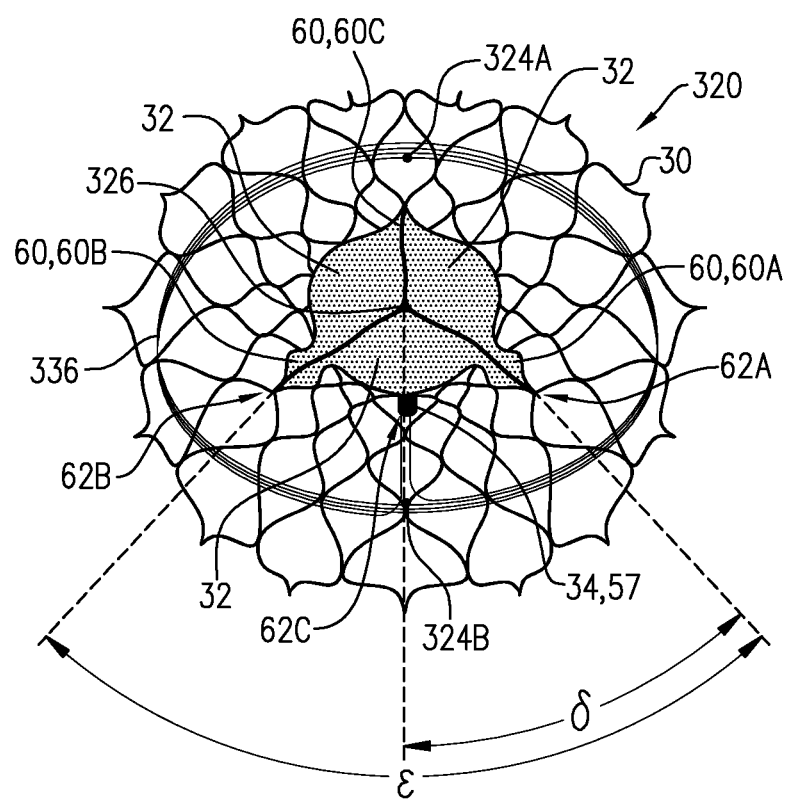
FIG. 7 is a schematic illustration of the prosthetic aortic valve of FIG. 6 viewed from a downstream outflow end of the prosthetic aortic valve, in accordance with an application of the present invention.

Reference is also made to FIG. 7, which is a schematic illustration of prosthetic aortic valve 320 viewed from downstream outflow end 52 of prosthetic aortic valve 320, as described hereinbelow, in accordance with an application of the present invention.

Prosthetic aortic valve 320 is shown in FIGS. 6 and 7 in an expanded configuration, which is similar to the expanded fully-deployed configuration described hereinbelow with reference to FIGS. 10C-D, except that in FIGS. 6 and 7 expansion of prosthetic aortic valve 320 is not limited by anatomy of a patient.

Prosthetic aortic valve 320 comprises:
- frame 30;
- plurality of prosthetic leaflets 32 coupled to frame 30;
- electrodes 34, which include cathode 54 and anode 57, and which are mechanically coupled to frame 30; and a prosthetic-valve coil 336 coupled to frame 30 in non-wireless electrical communication with cathode 54 and anode 57.

Frame 30 typically comprises a stent or other structure, which is typically self-expanding, and may be formed by laser cutting or etching a metal alloy tube comprising, for example, stainless steel or a shape memory material such as Nitinol. For some applications, one or more of electrodes 34 are coupled to frame 30 using techniques described in U.S. Pat. No. 9,526,637 to Dagan et al. and/or US 2016/0278951 to Dagan et al., both of which are incorporated herein by reference. For some applications, prosthetic-valve coil 336 comprises gold wire, in order to provide low resistance.

Prosthetic-valve coil 336 may be coupled to frame 30 either inside the frame or outside the frame, or partially inside and partially outside the frame.

Prosthetic aortic valve 320 is configured to be delivered to a native aortic valve of a patient in a constrained delivery configuration within delivery sheath 372, such as described hereinbelow with reference to FIGS. 10A-B.

For some applications, when prosthetic aortic valve 320 is in an expanded fully-deployed configuration upon release from delivery sheath 372, such as shown in FIGS. 6, 7, and 10C-D, (a) a line 322 defined between upstream-most and downstream-most points 324A and 324B of mechanical coupling between prosthetic-valve coil 336 and frame 30 and (b) a central longitudinal axis 326 defined by frame 30 form an angle γ (gamma) of between 20 and 70 degrees, such as between 30 and 60 degrees, e.g., between 40 and 50 degrees, such as 45 degrees. This angle provides good coupling between prosthetic-valve coil 336 and an energy-transmission coil, such as described hereinbelow with reference to FIG. 10D.

For some applications, when prosthetic aortic valve 320 is in the expanded fully-deployed configuration, such as shown in FIGS. 6, 7, and 10C-D, central longitudinal axis 326 passes through a space surrounded by prosthetic-valve coil 336, such as shown in the figures.

Alternatively or additionally, for some applications, prosthetic-valve coil 336 is shaped so as to define a best-fit plane that forms angle γ (gamma) with central longitudinal axis 326 of frame 30.

As used in the present application, including in the claims and Inventive Concepts, the "central longitudinal axis" 326 of frame 30 is the set of all centroids of transverse cross-sectional sections of frame 30 along frame 30. Thus the cross-sectional sections are locally perpendicular to the central longitudinal axis, which runs along frame 30. (For applications in which frame 30 is circular in cross-section, the centroids correspond with the centers of the circular cross-sectional sections.) As used in the present application, including in the claims and Inventive Concepts, a "best-fit plane" is the plane that most closely matches the shape of prosthetic-valve coil 336, i.e., the plane that results in the minimal sum of squares of distances between the plane and prosthetic-valve coil 336. As used in the present application, including in the claims and Inventive Concepts, an angle between two lines or between a line and a plane is the smaller of the two supplementary angles between the two lines or the line and the plane, or equals 90 degrees if the two lines or the line and the plane are perpendicular.

This angling of prosthetic-valve coil 336 with respect to central longitudinal axis 326 of frame 30 allows more compact crimping (compression) of prosthetic-valve coil 336 into delivery sheath 372, such as described hereinbelow with reference to FIGS. 10A-B, than in an alternate configuration in which prosthetic-valve coil 336 is perpendicular to central longitudinal axis 326 of frame 30, because the metal of prosthetic-valve coil 336 is more axially distributed along frame 30.

For other applications, prosthetic-valve coil 336 is angled at a different angle with respect to central longitudinal axis 326 of frame 30. For example, prosthetic-valve coil 336 may be perpendicular to central longitudinal axis 326 of frame 30, such as shown in FIG. 1A.

For some applications, when prosthetic aortic valve 320 is in the expanded fully-deployed configuration, such as shown in FIGS. 6, 7, and 10C-D (a) downstream-most point 324B of mechanical coupling between prosthetic-valve coil 336 and frame 30 and (b) a centroid 328 of cathode 54 are rotationally aligned with each other or rotationally offset from each other about central longitudinal axis 326 by less than 50 degrees, such as less than 30 degrees. A reason for this rotational alignment is provided hereinbelow with reference to FIGS. 10B and 10D.

For some applications, cathode 54 is located upstream of anode 57 along frame 30.

For some applications, cathode 54 and anode 57 are used for bipolar sensing and/or pacing, as known in the art.

For some applications, cathode 54 and anode 57 are disposed on frame 30 such that there is at least 15 mm between the cathode and the anode, when prosthetic aortic valve 320 is in the expanded fully-deployed configuration described hereinbelow with reference to FIGS. 10C-D (the 15 mm is measured along central longitudinal axis 326 of frame 30 when in the expanded fully-deployed configuration).

For some applications, respective non-electrically-insulated end portions of prosthetic-valve coil 336 define cathode 54 and anode 57. In these applications, prosthetic aortic valve 320 typically does not comprise elongate insulated electrical conductors, described hereinbelow with reference to FIG. 8. Instead, respective insulated end portions of prosthetic-valve coil 336 bend away from prosthetic-valve coil 336 along the paths of elongate insulated electrical conductors 438 described hereinbelow with reference to FIG. 9, such that the respective non-electrically-insulated end portions of prosthetic-valve coil 336 are located at the locations at which cathode 54 and anode 57 are shown in FIG. 6, respectively.

For other applications, prosthetic aortic valve 320 further comprises one or more elongate insulated electrical conductors 438, e.g., wires, which couple prosthetic-valve coil 336 in the non-wireless electrical communication with cathode 54 and anode 57, such as described hereinbelow with reference to FIG. 9, mutatis mutandis.

For some applications, prosthetic aortic valve 320 does not comprise any active electronic components.

For some applications, when prosthetic aortic valve 320 is in the expanded fully-deployed configuration, frame 30 is shaped so as to define upstream inflow portion 42, downstream outflow portion 44, and constriction portion 46, which is axially between upstream inflow portion 42 and downstream outflow portion 44. Prosthetic leaflets 32 are coupled to constriction portion 46 such that free edges 48 of prosthetic leaflets 32 face toward downstream outflow portion 44 when prosthetic aortic valve 320 is in the expanded fully-deployed configuration described hereinbelow with reference to FIGS. 10C-D. Prosthetic leaflets 32 are not coupled to downstream outflow portion 44; therefore, ring-shaped longitudinal border 58 between downstream outflow portion 44 and constriction portion 46 is defined by a downstream-most point of frame 30 to which prosthetic leaflets 32 are coupled (for example, prosthetic leaflets 32 may be coupled to the downstream-most point of frame 30 at commissures 60, described immediately hereinbelow). (Ring-shaped longitudinal border 58 is at the same longitudinal location around frame 30.) Typically, prosthetic aortic valve 320 further comprises skirt 49 coupled to upstream inflow portion 42 of frame 30, and prosthetic leaflets 32 are attached along their bases to skirt 49, for example, using sutures or a suitable biocompatible adhesive. Adjoining pairs of leaflets are attached to one another at their lateral ends to form commissures 60, with free edges 48 of the prosthetic leaflets forming coaptation edges that meet one another. Skirt 49 and prosthetic leaflets 32 typically comprise a sheet of animal pericardial tissue, such as porcine pericardial tissue, or synthetic or polymeric material.

For some applications, cathode 54 is coupled to upstream inflow portion 42 of frame 30.

For some applications, cathode 54 has lateral dimension a (alpha), measured in degrees around frame 30 with respect to central longitudinal axis 326 of frame 30, of between 10 and 40 degrees, e.g., between 20 and 40 degrees, such as 30 degrees, in order to accommodate rotational misplacement of frame 30 with respect to the bundle of His. Typically, prosthetic aortic valve 320 is deployed using imaging, such as fluoroscopy, and is rotated if necessary during the deployment such that cathode 54 is disposed against tissue of the annulus that is near the bundle of His. For some applications, prosthetic aortic valve 320 comprises a plurality of cathodes 54 (e.g., two or three, or more), which are disposed at a respective plurality of angular locations around frame 30 (e.g., 10-15 degrees apart). After implantation of prosthetic aortic valve 320, the cathode 54 that has the most accurate angular location is activated to apply a pacing signal and/or sense, either by (a) external control circuitry, such as external-unit control circuitry 104, described hereinbelow with reference to FIG. 10D, or (b) prosthetic-aortic-valve control circuitry 440, if provided, such as described hereinbelow with reference to FIG. 9. Alternatively or additionally, for some applications, cathode 54 has an axial length of at least 10 mm, in order to accommodate axial misplacement of frame 30 with respect to the annulus of the natural aortic valve, and thus with respect to the bundle of His. As used in the present application, including in the claims and Inventive Concepts, an "axial length" is a length of a structure measured along central longitudinal axis 326.

For some applications, cathode 54 has a thickness of between 75 and 125 microns, e.g., about 100 microns, and/or a surface area of at least 2.5 mm2, in order to provide adequate stimulation. For some applications, cathode 54 comprises titanium nitride (TiN). For some applications, skirt 49 is coupled to an external surface of upstream inflow portion 42 of frame 30, and cathode 54 is disposed on an external surface of skirt 49.

For some applications, when prosthetic aortic valve 320 is in the expanded fully-deployed configuration described hereinbelow with reference to FIGS. 10C-D:

frame 30 has an inflow end 50 at upstream inflow portion 42 and downstream outflow end 52 at downstream outflow portion 44, and an axial length, measured between inflow end 50 and downstream outflow end 52, and at least one of (e.g., exactly one of, e.g., cathode 54) the one or more electrodes 34 is coupled to upstream inflow portion 42 within a distance from inflow end 50, the distance equal to 10% of the axial length of frame 30 (the distance is measured (a) along central longitudinal axis 326 of frame 30 when in the expanded fully-deployed configuration, and (b) between inflow end 50 and an upstream-most point of the at least one electrode).

For some applications, downstream-most point 324B of mechanical coupling between prosthetic-valve coil 336 and frame 30 is located on downstream outflow portion 44 when prosthetic aortic valve 320 is in the expanded fully-deployed configuration.

For some applications, upstream-most point 324A of mechanical coupling between prosthetic-valve coil 336 and frame 30 is located on constriction portion 46 when prosthetic aortic valve 320 is in the expanded fully-deployed configuration.

For some applications, prosthetic leaflets 32 are coupled to frame 30 at at least first and second commissures 60A and 60B of prosthetic aortic valve 320 that are located at respective first and second angular locations 62A and 62B around frame 30. The first and second angular locations 62A and 62B are separated by a first angular offset ε (epsilon) around frame 30 (labeled in FIG. 7) when prosthetic aortic valve 320 is in the expanded fully-deployed configuration described hereinbelow with reference to FIGS. 10C-D. Cathode 54 is coupled to frame 30 at a third angular location 62C around frame 30 that is separated from first angular location 62A by a second angular offset δ (delta) that equals between 40% and 60% (e.g., 50%) of the first angular offset ε (epsilon) when prosthetic aortic valve 320 is in the expanded fully-deployed configuration described hereinbelow with reference to FIG. 10C-D. At the third angular location 62C around frame 30, the frame is more flexible than at the more rigid commissures. As used in the present application, including in the claims and Inventive Concepts, an "angular location" is a location on frame 30 at a particular location around central longitudinal axis 326, i.e., at a particular "o'clock" with respect to central longitudinal axis 326. (It is noted that a third commissure 60C is shown in FIG. 1A on the far side of the frame, i.e., 180 degrees from cathode 54.)

Reference is again made to FIG. 6, and is additionally again made to FIG. 3B, which, as described hereinabove, is a schematic illustration of passive electrical components of prosthetic aortic valve 120, described hereinabove with reference to FIGS. 3A-B, and tissue 122, in accordance with an application of the present invention. For some applications, prosthetic aortic valve 320 implements the techniques of prosthetic aortic valve 120 described with reference to FIG. 3B. External-unit control circuitry 104 (shown in FIG. 10D) typically wirelessly transfers energy to prosthetic-valve coil 336 by generating a plurality of AC pulses, each AC pulse including a train of AC bursts. The train of AC bursts may be generated, for example, at a frequency of between 3 kHz and 130 kHz (e.g., between 3 kHz and 100 kHz, or between 100 kHz and 130 kHz), or a frequency of between 12 and 20 MHz, such as between 13 and 20 MHz, e.g., 13.56 MHz, for improved efficiency. For some applications, there are 20-100 AC bursts in each of the AC pulses. Other frequencies and number of bursts are within the scope of the present invention. For some applications, external-unit control circuitry 104 is configured to wirelessly transfer, to prosthetic-valve coil 336, energy that generates between 5 and 10 V in prosthetic-valve coil 336.

For some applications, prosthetic aortic valve 320 comprises exactly one passive diode 124, which provides half-wave rectification of the AC pulses. For other applications, prosthetic aortic valve 320 comprises a plurality of passive diodes 124, which provides full-wave rectification of the AC pulses; for example, prosthetic aortic valve 320 may comprise four passive diodes 124 arranged in a bridge configuration, as is known in the electronics arts.

For some applications, prosthetic aortic valve 320 comprises capacitor 126 (shown highly schematically in the exploded view to the right in FIG. 6, as well as in FIG. 3B), which is in electrical communication with cathode 54 and anode 57 (parallel to tissue 122 in the circuit made upon implantation of the electrodes). Capacitor 126 typically increases the efficiency of the circuit by delivering a larger proportion of the received energy into tissue 122. (As is known in the electronics art, a capacitor is a passive electrical component.)

Optionally, prosthetic aortic valve 320 comprises additional passive electrical components, such as one or more resistors.

Figure 8:
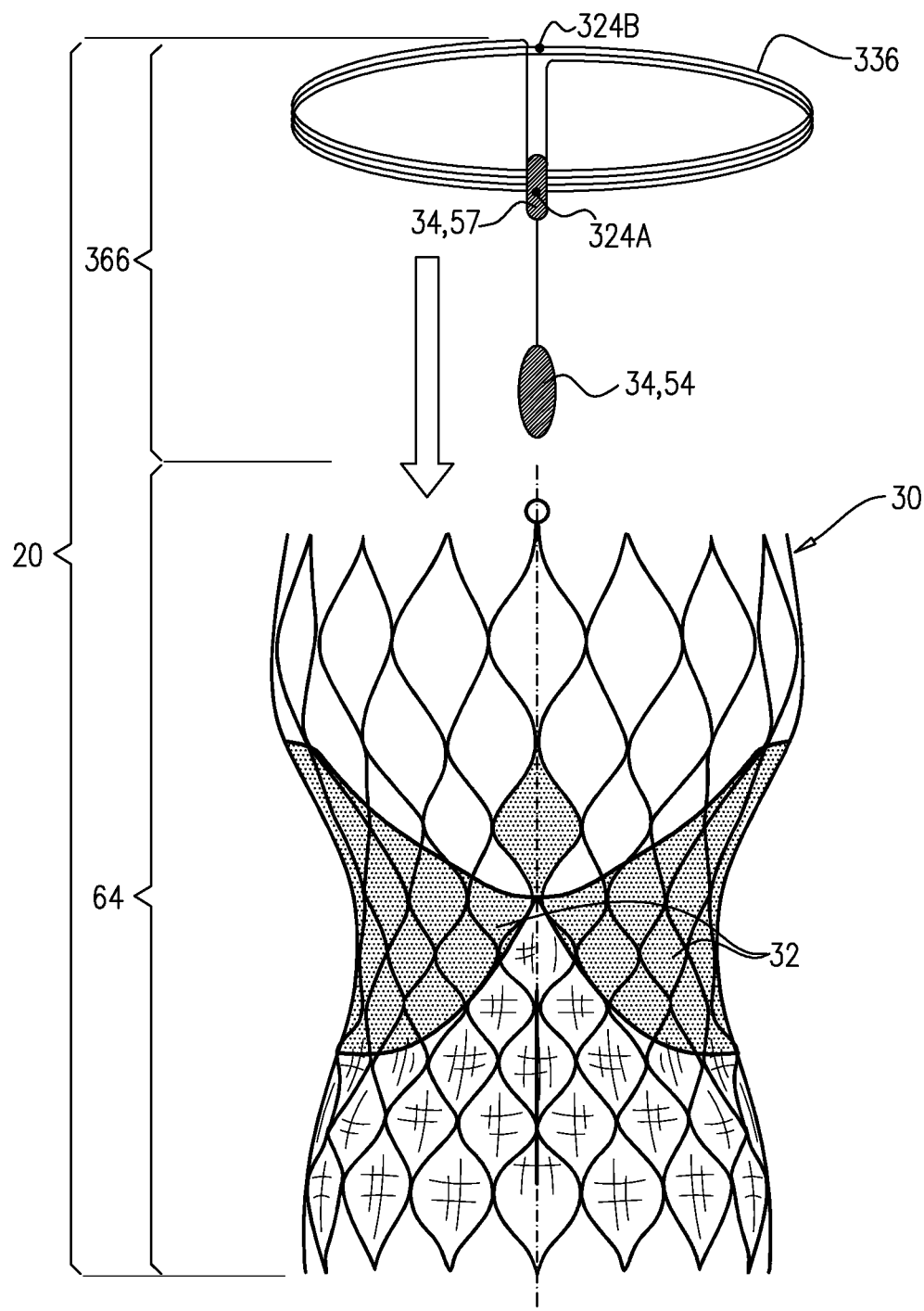
FIG. 8 is a schematic illustration of components of the prosthetic aortic valve of FIG. 6 before complete assembly, in accordance with an application of the present invention.

Reference is now made to FIG. 8, which is a schematic illustration of components of prosthetic aortic valve 320 before complete assembly, in accordance with an application of the present invention. The components comprise valve component 64 and an electronics component 366. Valve component 64 typically consists of a heart valve prosthesis known in the art, which comprises at least frame 30 and prosthetic leaflets 32. For example, the known heart valve prosthesis may comprise a CoreValve™ Evolut™ R prothesis (Medtronic, Inc., Minneapolis, Minn., USA), a CoreValve™ Evolut™ PRO prosthesis (Medtronic, Inc.), a LOTUS Edge™ Aortic Valve (Boston Scientific Corporation, Marlborough, Mass., USA), or an ACURATE Neo™ Aortic Valve (Boston Scientific Corporation). Electronics component 366 comprises at least the one or more electrodes 34 and prosthetic-valve coil 336, and optionally, in the configuration described hereinbelow with reference to FIG. 9, prosthetic-aortic-valve control circuitry 440.

During assembly of prosthetic aortic valve 320, electronics component 366 is inserted into valve component 64. For some applications, a first portion of electronics component 366, such as prosthetic-valve coil 336 and one of the one or more electrodes 34, is coupled to an inner surface of frame 30, and a second portion of electronics component 366, such as cathode 54, is coupled to an external surface of frame 30. For example, one of the non-electrically-insulated end portions of prosthetic-valve coil 336 may (a) electrically couple prosthetic-valve coil 336 to cathode 54 and (b) pass from inside to outside frame 30, typically through skirt 49. (Coupling one of the one or more electrodes 34 to the inner surface of frame 30 may expose the electrode to blood of the subject upon implantation of the assembled prosthetic aortic valve 320. Coupling cathode 54 to the external surface of frame 30 may dispose the cathode against tissue, such as tissue of the annulus that is near the bundle of His, upon implantation of the assembled prosthetic aortic valve 320, such as described herein.) Optionally, the components of electronics component 366 may be stitched to frame 30 and/or skirt 49.

For some applications, whether prosthetic-valve coil 336 is coupled to an inner or an external surface of frame 30, prosthetic-valve coil 336 is electrically isolated from frame 30, such as by isolation material (e.g., a sheet of material or a coating) disposed between prosthetic-valve coil 336 and frame 30. For example, the isolation material may comprise a non-conductive polymer.

The above-mentioned assembly of prosthetic aortic valve 320 is typically performed in a manufacturing facility, and thereafter the assembled prosthetic aortic valve 320 is packaged and shipped to a healthcare facility for implantation. The method of assembling prosthetic aortic valve 320 is thus non-surgical.

Figure 9:
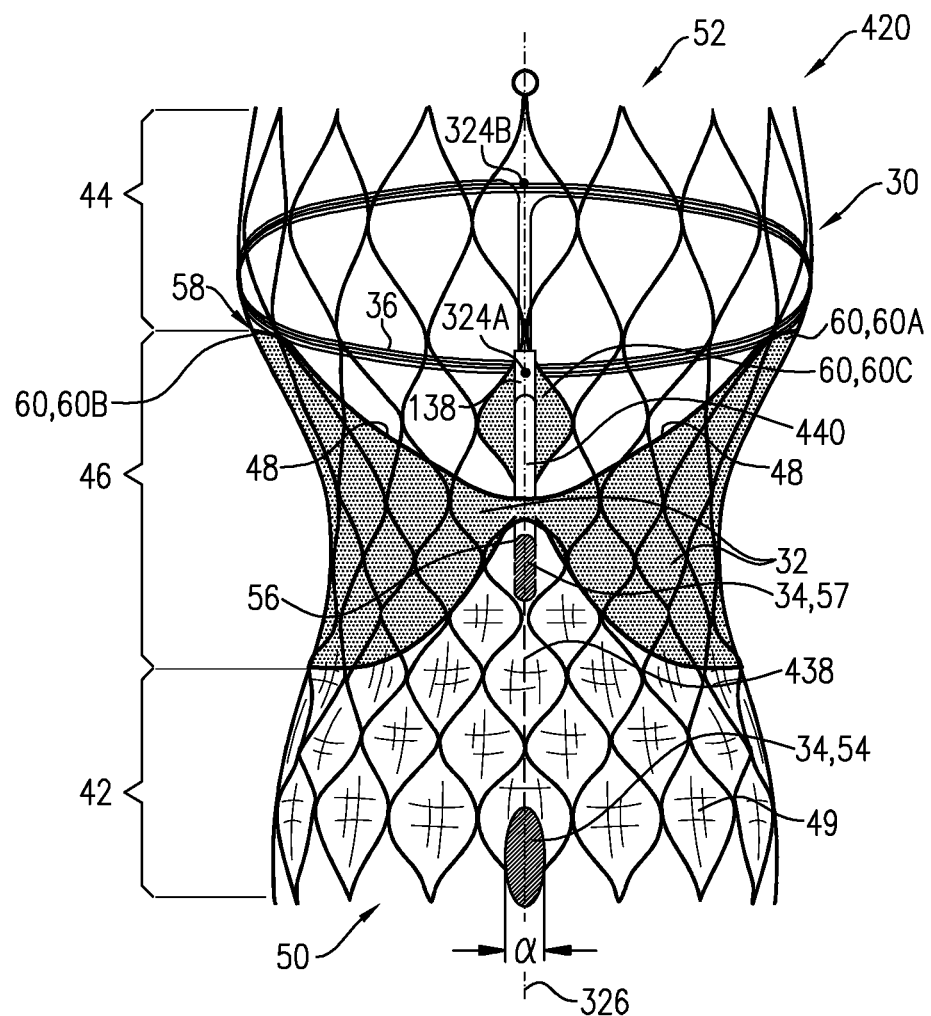
FIG. 9 is a schematic illustration of another prosthetic aortic valve, in accordance with an application of the present invention.

Reference is now made to FIG. 9, which is a schematic illustration of a prosthetic aortic valve 420, in accordance with an application of the present invention. Prosthetic aortic valve 420 is shown in FIG. 9 in an expanded configuration, which is similar to the expanded fully-deployed configuration of prosthetic aortic valve 320 described hereinbelow with reference to FIGS. 10C-D, except that in FIG. 9 expansion of prosthetic aortic valve 420 is not limited by anatomy of a patient. Other than as described hereinbelow, prosthetic aortic valve 420 is identical to prosthetic aortic valve 320 described herein with reference to FIGS. 6-8, and like reference numerals refer to like parts. Prosthetic aortic valve 420 may be assembled as described hereinabove with reference to FIG. 8 for prosthetic aortic valve 320, mutatis mutandis.

Prosthetic aortic valve 420 further comprises prosthetic-aortic-valve control circuitry 440, which is coupled to frame 30 and which is in non-wireless electrical communication with the one or more electrodes 34. In these applications, prosthetic-valve coil 336 is in non-wireless electrical communication with prosthetic-aortic-valve control circuitry 440, such that prosthetic-valve coil 336 is in non-wireless electrical communication with the one or more electrodes 34 via prosthetic-aortic-valve control circuitry 440. One or more of the one or more electrodes 34 may be directly attached in non-wireless electrical communication to prosthetic-aortic-valve control circuitry 440, and/or may be attached in non-wireless electrical communication to prosthetic-aortic-valve control circuitry 440 by the one or more elongate insulated electrical conductors 438. Typically, prosthetic-aortic-valve control circuitry 440 is flexible, and has a thin, linear packaging, and may implement, mutatis mutandis, techniques described with reference to FIG. 5. The thinness of control circuitry 440 allows it to be compressed in delivery sheath 372 during deployment of prosthetic aortic valve 420, without the need to increase the diameter of the delivery sheath. In addition, the flexibility of control circuitry 440 prevents damage to the control circuitry when it is crimped when compressed into the delivery sheath.

Typically, prosthetic-aortic-valve control circuitry 440 is coupled to frame 30 such that upstream-most point 56 of prosthetic-aortic-valve control circuitry 440 is disposed axially along constriction portion 46 and/or downstream outflow portion 44 of frame 30.

Typically, prosthetic-aortic-valve control circuitry 440 is coupled to frame 30 inside frame 30, which may prevent friction between prosthetic-aortic-valve control circuitry 440 and delivery sheath 372 during deployment of prosthetic aortic valve 320, described hereinbelow with reference to FIGS. 10A-D regarding prosthetic aortic valve 320, mutatis mutandis.

For some applications, prosthetic-aortic-valve control circuitry 440 is coupled to frame 30 at third angular location 62C around frame 30, described hereinabove with reference to FIG. 7.

Figure 10A:
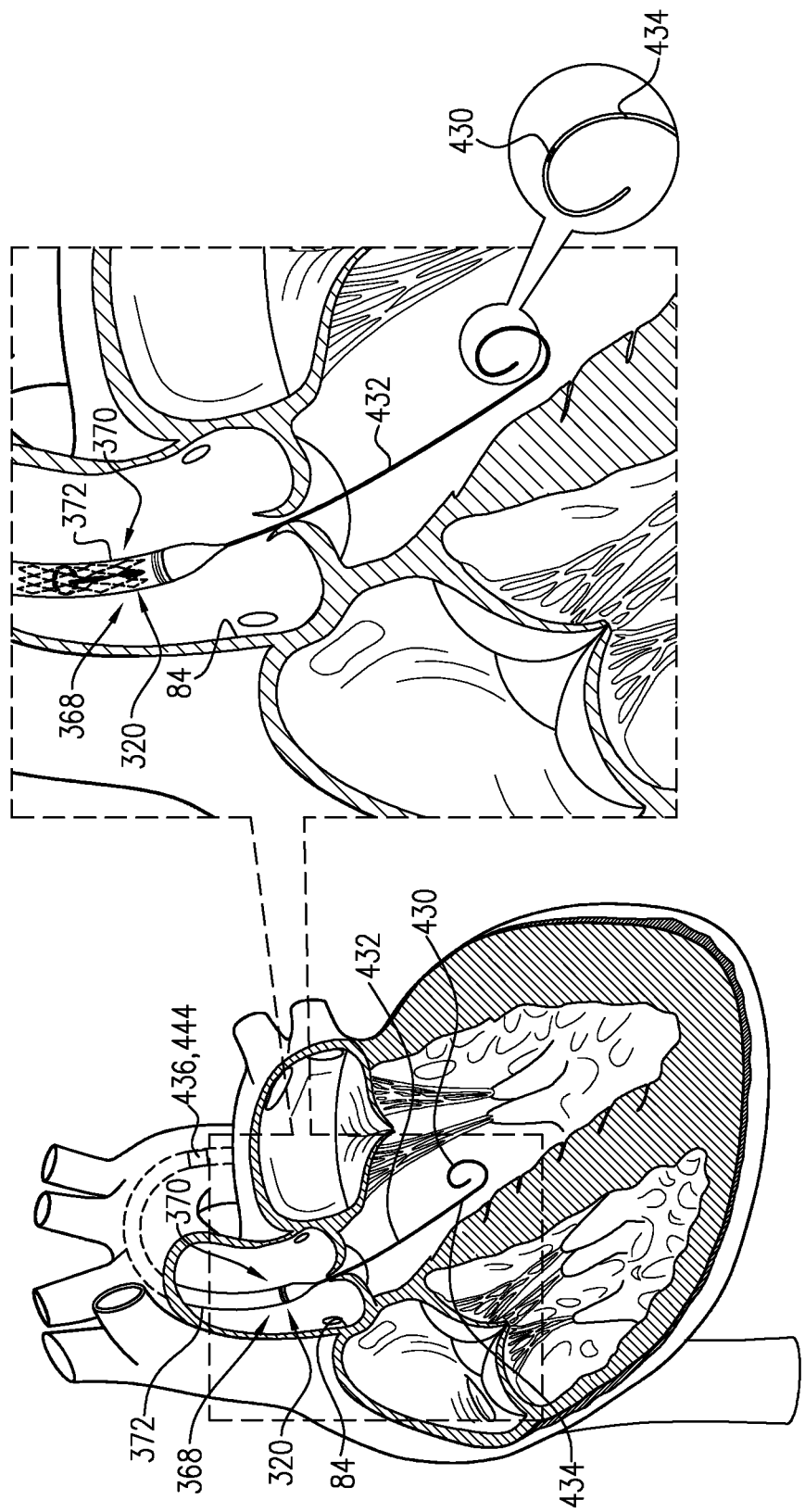
FIGS. 10A-D are schematic illustrations of a valve prosthesis system and a method of using the system, in accordance with respective applications of the present invention.
Figure 10B:
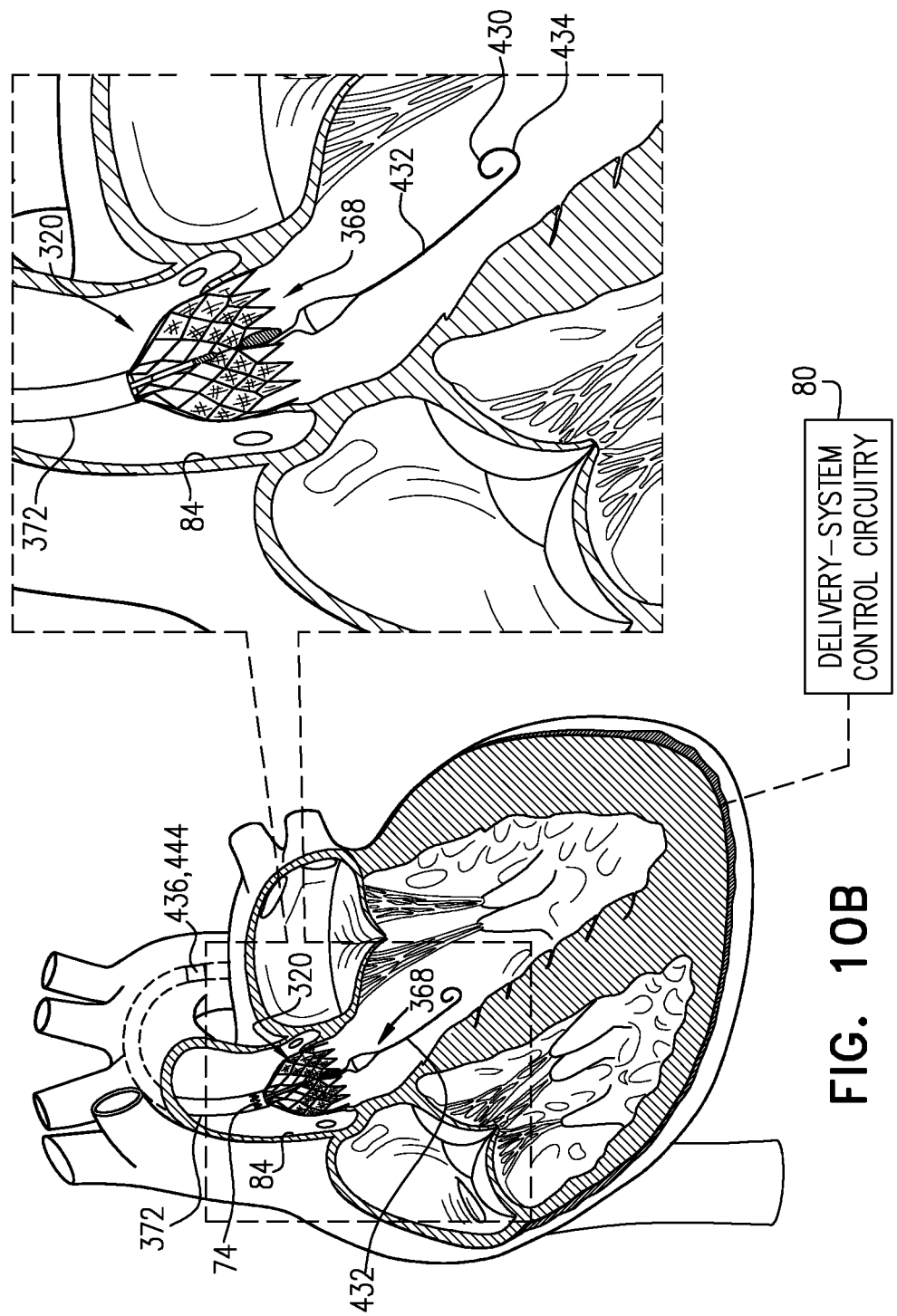
Figure 10C:
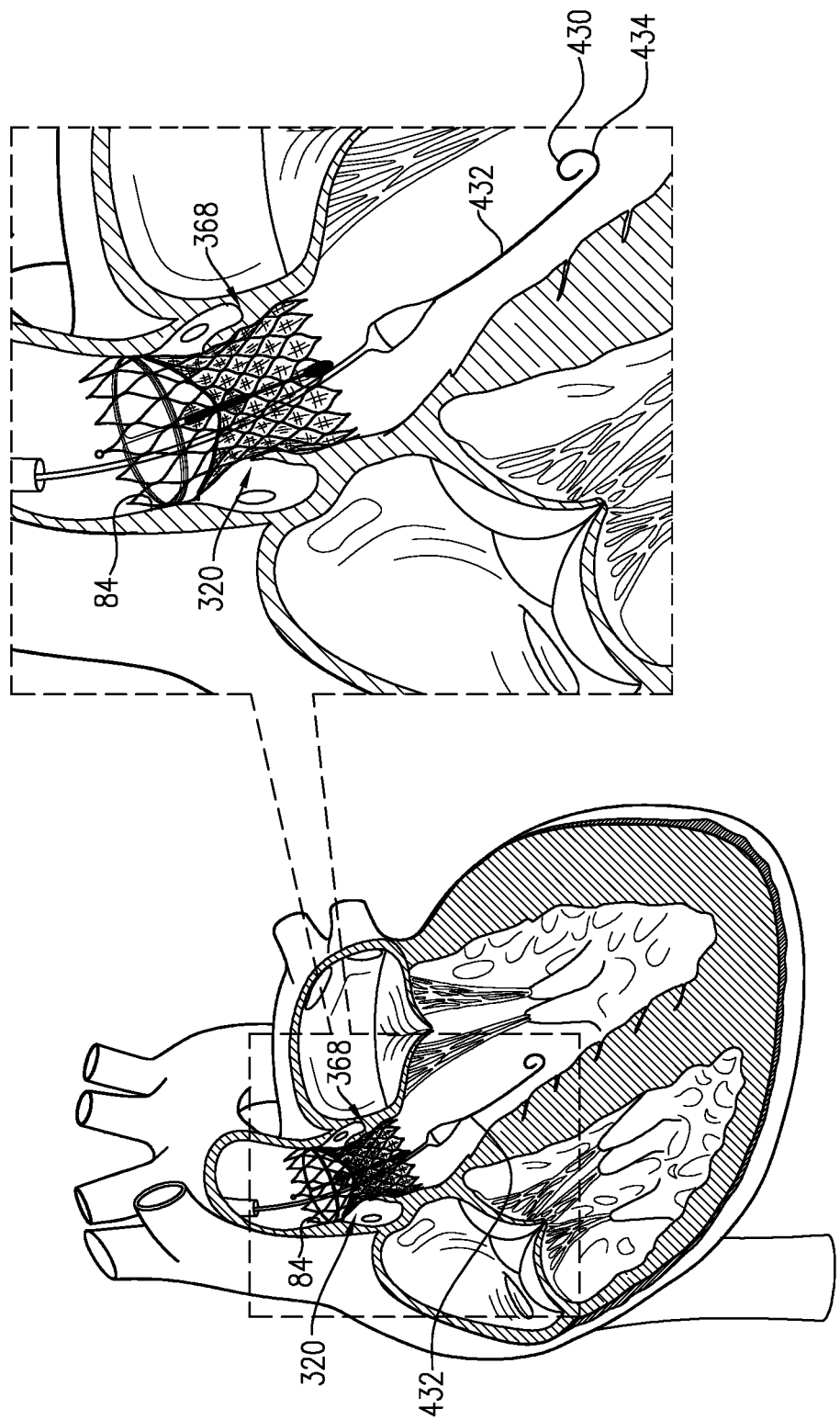
Figure 10D:
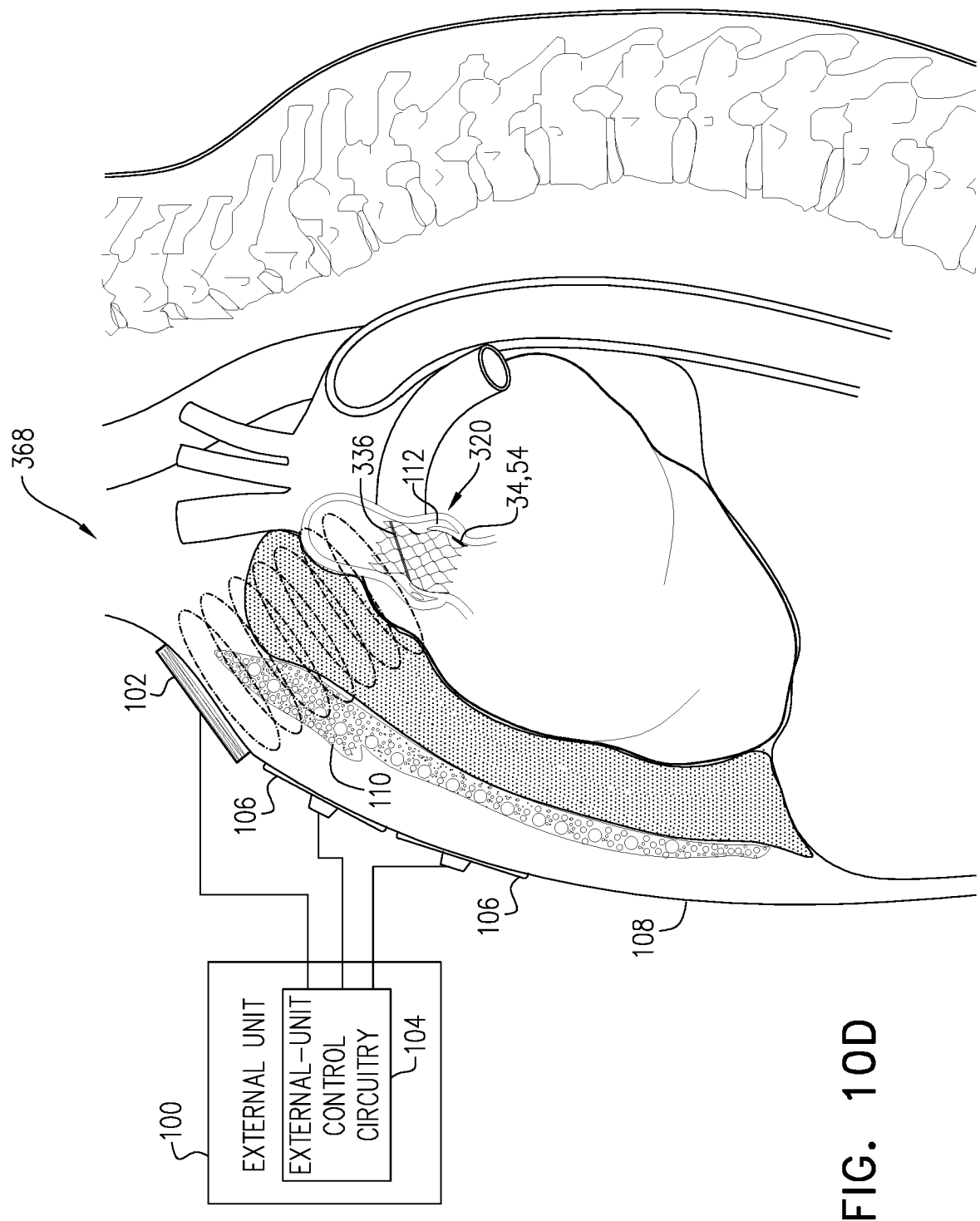

Reference is now made to FIGS. 10A-D, which are schematic illustrations of a valve prosthesis system 368 and a method of using the system, in accordance with respective applications of the present invention. Although the techniques described with reference to FIGS. 10A-D are generally described regarding prosthetic aortic valve 320, the techniques are equally applicable to prosthetic aortic valves 20, 120, 420, and 820, mutatis mutandis. The rotational orientation of the prosthetic aortic valve is shown schematically in FIGS. 10A-C, in order to illustrate the components of the prosthetic aortic valve; as described below, in actual use, the prosthetic aortic valve is typically rotationally oriented such that cathode 54 is positioned adjacent to cardiac tissue near the bundle of His, such as shown in FIG. 10D.

Valve prosthesis system 368 comprises (a) prosthetic aortic valve 320 or prosthetic aortic valve 420 and (b) a delivery system 370.

Delivery system 370 comprises:

delivery sheath 372;

one or more wires 78, which pass along delivery sheath 372, e.g., attached to an outer or inner surface of delivery sheath 372, or embedded in the wall of delivery sheath 372; and optionally, delivery-system control circuitry 80, which is in electrical communication with delivery-system coil 74 via the one or more wires 78.

As shown in FIG. 10A, prosthetic aortic valve 320 is removably disposable in delivery sheath 372 in a compressed delivery configuration. During an implantation procedure, delivery sheath 372 is advanced through vasculature of a patient, until distal end 82 of delivery sheath 372 is disposed in an ascending aorta 84 of the patient, while prosthetic aortic valve 320 is removably disposed in delivery sheath 372 in the compressed delivery configuration.

As described hereinabove with reference to FIGS. 6-7, for some applications, the one or more electrodes 34 comprise cathode 54 that is coupled to upstream inflow portion 42 of frame 30. Before deployment, the prosthetic aortic valve is rotated (such as under guidance using imaging, e.g., fluoroscopy, such as of a marker on delivery sheath 372) such that cathode 54 is positioned adjacent to cardiac tissue near the bundle of His (near a non-coronary cusp 112 of the native aortic valve (labeled in FIG. 10D)), in order to pace the heart by stimulating the cardiac tissue with cathodic current.

Because of the rotational alignment of angled prosthetic-valve coil 336 with respect to cathode 54 described hereinabove with reference to FIGS. 6-7, the alignment of cathode 54 adjacent to cardiac tissue near the bundle of His (facing generally posteriorly) automatically aligns prosthetic-valve coil 336 facing generally in the opposite direction, facing generally anterio-superiorly, such as shown in FIG. 10D. This orientation provides good wireless coupling with an energy-transmission coil 102, such as described hereinbelow with reference to FIG. 10D.

For some applications, delivery system 370 comprises a cathode 430 separate from prosthetic aortic valve 320 or prosthetic aortic valve 420. For some applications, the separate cathode is disposed on a guidewire 432 used to introduce prosthetic aortic valve 320 or prosthetic aortic valve 420 into the native aortic valve. For example, cathode 430 may be located on a pigtail 434 of guidewire 432. To this end, pigtail 434 may optionally comprise an internal electrically-conductive wire coated with a non-conductive insulation, and cathode 430 may be defined by a non-insulated portion of pigtail 434. Delivery system 370 is configured to use this guidewire cathode 430 for applying rapid ventricular pacing (rather than cathode 54 of prosthetic aortic valve 320 or prosthetic aortic valve 420). In this case, cathode 54 of prosthetic aortic valve 320 or prosthetic aortic valve 420 is still typically used for applying post-implantation chronic pacing using external unit 100, such as described below.

For some applications, such as those in which delivery system 370 comprises cathode 430 separate from prosthetic aortic valve 320 or prosthetic aortic valve 420, delivery system 370 comprises an anode 436 separate from prosthetic aortic valve 320 or prosthetic aortic valve 420, and is configured to use this separate anode 436 for applying rapid ventricular pacing (rather than anode 57 of prosthetic aortic valve 320 or prosthetic aortic valve 420). In this case, anode 57 of prosthetic aortic valve 320 or prosthetic aortic valve 420 is still typically used for applying post-implantation chronic pacing using external unit 100, such as described below.

For some applications, the separate anode 436 of delivery system 370 comprises:

a skin electrode 442 (shown in FIGS. 12 and 13B, described hereinbelow), e.g., a patch electrode, configured to be placed on skin of the patient; the patch electrode may have a relatively large surface area, e.g., a diameter of 6 to 10 cm (e.g., 8 cm), in order to provide good conduction; optionally, the patch electrode is incorporated into shirt 600, described hereinbelow with reference to FIGS. 13A-B (such as embedded into the shirt, or attached to an inner surface of the shirt), a sheath electrode 444, e.g., a conductive coating, disposed along delivery sheath 372, such as along a proximal portion of the sheath that is configured to be disposed in the aorta, e.g., the descending aorta, when distal end 82 of delivery sheath 372 is disposed in an ascending aorta 84 for deployment of the prosthetic aortic valve, or a sheath-introducer electrode, disposed on an introducer used to introduce the sheath into the vasculature at the vascular access site (e.g., the femoral vascular access site), typically, the sheath-introducer electrode is disposed along the introducer.

For some applications, delivery-system control circuitry 80 is configured to drive cathode 430 to apply unipolar rapid ventricular pacing, using anode 436 as the return electrode. Such pacing may temporarily reduce left ventricular output, in order to enable more accurate placement of the prosthetic aortic valve. Delivery-system control circuitry 80 sets the parameters of the pacing signal.

As shown in FIGS. 10C-D, prosthetic aortic valve 320 is also configured to assume an expanded fully-deployed configuration upon being fully released from distal end 82 of delivery sheath 372.

For some applications, as shown in FIG. 10D, valve prosthesis system 368 further comprises external unit 100. External unit 100 is configured to be disposed outside a body of the patient and comprises (a) energy-transmission coil 102, and (b) external-unit control circuitry 104, which is configured to drive energy-transmission coil 102 to wirelessly transfer energy, by inductive coupling, to prosthetic-valve coil 336 when prosthetic aortic valve 320 is in the expanded fully-deployed configuration, as shown in FIG. 10D. In these applications, after prosthetic aortic valve 320 is fully released from distal end 82 of delivery sheath 372, external-unit control circuitry 104 is activated to drive energy-transmission coil 102 to wirelessly transfer energy, by inductive coupling, to prosthetic-valve coil 336 when prosthetic aortic valve 320 is in the expanded fully-deployed configuration.

Alternatively, valve prosthesis system 368 comprises external unit 100, and does not comprise delivery system 370.

Further alternatively, in some applications, a single external unit may be provided that provides the functionality of both delivery system 370 and external unit 100. The single external unit may comprise control circuitry that is configured to provide the functionality of both delivery-system control circuitry 80 of delivery system 370 and external-unit control circuitry 104 of external unit 100. The single external unit may be configured to operate in a delivery mode and a post-delivery mode. A user control may be provided to switch between the two modes of operation, or the control circuitry may be configured to automatically switch between the two modes of operation.

For some applications, energy-transmission coil 102 is configured to be positioned against the patient's chest, typically over a sternum 110. This positioning of energy-transmission coil 102 provides high transmission efficiency, because the respective axes of energy-transmission coil 102 and prosthetic-valve coil 336 are generally aligned, because of the angle γ (gamma) formed between prosthetic-valve coil 336 and central longitudinal axis 326 of frame 30 described hereinabove with reference to FIGS. 6-7. This high transmission efficiency may allow prosthetic-valve coil 336 and/or energy-transmission coil 102 to include fewer turns of the coil(s) and/or to have smaller diameters. Alternatively or additionally, this high transmission efficiency may allow external unit 100 to use less power to induce the same amount of current in prosthetic-valve coil 336.

For other applications, energy-transmission coil 102 is configured to be positioned around the patient's neck, such as described hereinbelow with reference to FIG. 13C. This positioning of energy-transmission coil 102 provides high transmission efficiency (although perhaps not as high as when against the patient's chest), because the respective axes of energy-transmission coil 102 and prosthetic-valve coil 336 are generally aligned, because of the angle γ (gamma) formed between prosthetic-valve coil 336 and central longitudinal axis 326 of frame 30 described hereinabove with reference to FIGS. 6-7.

Further alternatively, for some applications, energy-transmission coil 102 is configured to be positioned on the patient's back. In this configuration, prosthetic-valve coil 336 may be angled to face generally posterio-superiorly, rather than generally anterio-superiorly as shown in the figures. For example, (a) upstream-most point 324A of mechanical coupling between prosthetic-valve coil 336 and frame 30 and (b) centroid 328 of cathode 54 may be rotationally aligned with each other or rotationally offset from each other about central longitudinal axis 326 by less than 50 degrees, such as less than 30 degrees. This positioning of energy-transmission coil 102 provides high transmission efficiency (although perhaps not as high as when against the patient's chest), because the respective axes of energy-transmission coil 102 and prosthetic-valve coil 336 are generally aligned, because of the angle γ (gamma) formed between prosthetic-valve coil 336 and central longitudinal axis 326 of frame 30 described hereinabove with reference to FIGS. 6-7.

Optionally, energy-transmission coil 102 is shaped so as to define 4-10 turns.

Optionally, energy-transmission coil 102 has a diameter of 15-20 cm.

For some applications in which valve prosthesis system 368 comprises prosthetic aortic valve 120, described hereinabove with reference to FIGS. 3A-B, or prosthetic aortic valve 320, described hereinabove with reference to FIGS. 6-8, external-unit control circuitry 104 is configured to drive cathode 54 to apply a cathodic current. For some applications in which valve prosthesis system 368 comprises prosthetic aortic valve 20, described hereinabove with reference to FIGS. 1A-2, or prosthetic aortic valve 420, described hereinabove with reference to FIG. 9, prosthetic-aortic-valve control circuitry 40 or 440 is configured to drive cathode 54 to apply a cathodic current.

For some applications in which valve prosthesis system 368 comprises prosthetic aortic valve 120, described hereinabove with reference to FIGS. 3A-B, or prosthetic aortic valve 320, described hereinabove with reference to FIGS. 6-8, external-unit control circuitry 104 is configured to drive the one or more electrodes 34 to perform pacing post-implantation, e.g., for several months, by applying a pacing signal, such as a standard, chronic pacing signal. External-unit control circuitry 104 sets the parameters of the pacing signal. Such pacing may employ any standard pacing protocol. Such pacing is typically bipolar. For some applications, the pacing is VVI pacing, which is only applied when a QRS complex is not sensed in the ventricle.

For some applications in which valve prosthesis system 368 comprises prosthetic aortic valve 20, described hereinabove with reference to FIGS. 1A-2, or prosthetic aortic valve 420, described hereinabove with reference to FIG. 9, prosthetic-aortic-valve control circuitry 40 or 440 is configured to use the energy received from external-unit control circuitry 104 to drive the one or more electrodes 34 to perform the post-implantation pacing. Alternatively, for some applications in which valve prosthesis system 368 comprises prosthetic aortic valve 20, described hereinabove with reference to FIGS. 1A-2, or prosthetic aortic valve 420, described hereinabove with reference to FIG. 9, prosthetic-aortic-valve control circuitry 40 or 440 is configured to (a) use the one or more electrodes 34 to sense a cardiac signal, and (b) drive prosthetic-valve coil 336 to transmit a wireless signal indicative of the sensed cardiac signal. For some applications, the cardiac sensing is performed using techniques described in U.S. Pat. No. 9,005,106 to Gross et al., which is incorporated herein by reference. In these applications, the one or more electrodes 34 are typically not used to apply pacing, any thus need not be configured as a cathode and an anode. Such sensing may enable early discharge of the patient from the hospital after implantation of prosthetic aortic valve 320, before the possible development of left bundle branch block (LBBB). If LBBB develops, as it does in approximately 20-30% of patients, the LBBB is detected by the sensing, an alert is generated, and the LBBB may be treated as appropriate.

For some applications in which valve prosthesis system 368 comprises prosthetic aortic valve 120, described hereinabove with reference to FIGS. 3A-B, or prosthetic aortic valve 320, described hereinabove with reference to FIGS. 6-8, external-unit control circuitry 104 (FIG. 10D)) is configured to drive cathode 54 and anode 57 to set parameters of the pacing signal. For example, external-unit control circuitry 104 may be configured to set an amplitude of the pacing signal by modulating an amplitude of the energy wirelessly transferred from the energy-transmission coil to prosthetic-valve coil 336. Alternatively or additionally, for example, external-unit control circuitry 104 may be configured to drive cathode 54 and anode 57 to (a) begin application of each pulse of the pacing signal by beginning wirelessly transferring energy from the energy-transmission coil to prosthetic-valve coil 336, and (b) conclude the application of each pulse of the pacing signal by ceasing wirelessly transferring energy from the energy-transmission coil to prosthetic-valve coil 336.

The inventor has determined that, in some configurations, it is difficult to assess suitable pacing parameters, e.g., due to patient size or patient body mass distribution, or for example due to technical issues such as variable electrical impedance between heart tissue and cathode 54 and anode 57, or the variable relative orientation of energy-transmission coil 102 and prosthetic-valve coil 336. For some applications, therefore, external unit 100 further comprises at least two sensing skin ECG electrodes 106, placed on the patient's skin 108, e.g., on the chest as shown in FIG. 10D. External-unit control circuitry 104 drives cathode 54 and anode 57 to apply a pacing signal to the patient's heart, and to detect at least one cardiac parameter using sensing skin ECG electrodes 106. External-unit control circuitry 104, at least partially responsively to the detected cardiac parameter, sets parameters of the pacing signal, by wirelessly transferring energy from energy-transmission coil 102 to prosthetic-valve coil 336 by inductive coupling. Because prosthetic aortic valves 120 and 320 typically do not comprise any active electronic components, the wireless transfer of energy from the energy-transmission coil to prosthetic-valve coil 36 or prosthetic-valve coil 336 by inductive coupling itself inductively drives the pacing current through prosthetic-valve coil 36 or 336.

Alternatively, external unit 100 comprises another type of cardiac sensor, instead of sensing skin ECG electrodes 106. For example, the cardiac sensor may comprise a heart rate sensor, such as an optical heart rate sensor (e.g., which uses photoplethysmography), or an ECG sensor, such as an optical ECG sensor (e.g., a single channel ECG sensor, such as the Si1172 or Si1173 biometric modules, manufactured by Silicon Laboratories Inc., Austin, Tex., USA).

External-unit control circuitry 104 typically analyzes the detected cardiac parameter to assess a level of responsiveness of the heart to the pacing signal. Upon ascertaining that the level of responsiveness is unsatisfactory, external-unit control circuitry 104 increases the strength of the pacing signal responsively to the detected cardiac parameter (e.g., by increasing the amplitude or the duration of the pacing signal). For example, the pulse width (typically 0.1-1 ms, e.g., 0.25-0.8 ms) of pulses of the pacing signal, or current amplitude in the energy-transmission coil may be iteratively increased, until a determination is made that the heart is suitably responding to the pacing pulses applied to the tissue. At this point, optionally, the strength of the pacing signal is further increased, e.g., by 50-150%, for example by 100%.

For some applications, the detected cardiac parameter is a timing feature of cardiac activity (e.g., heart rate, or the timing of a particular feature of the cardiac cycle). In this case, the parameters of the pacing signal may include a timing parameter of the pacing signal, and external-unit control circuitry 104 sets the timing parameter of the pacing signal responsively to the timing feature of the detected cardiac parameter.

It is noted that, as appropriate for a given patient, pacing of the heart may be applied in a manner that is synchronized to the cardiac cycle of the patient (based on the signals received by sensing skin ECG electrodes 106 or the other cardiac sensor), or the pacing may not be synchronized with the cardiac cycle of the patient.

Sensing skin ECG electrodes 106 are typically suction ECG electrodes or configured to be electrically coupled to the skin by an adhesive. In general, conventional ECG electrodes are suitable to be used for sensing skin ECG electrodes 106. It is noted that although conventional ECG electrodes may be used, complete ECG analysis as is known in the field of electrocardiography typically is not performed in order to implement the functions of external-unit control circuitry 104 described hereinabove.

For some applications, energy-transmission coil 102 and/or ECG electrodes 106 (or another cardiac sensor) are incorporated into shirt 600 configured to be worn by the patient (such as embedded into the shirt, or attached to an inner surface of the shirt), such as described hereinbelow with reference to FIGS. 13A-B, and/or incorporated into a band configured to be worn around the patient's chest or as a necklace 700 configured to be worn around the patient's neck, such as described hereinbelow with reference to FIG. 13C. Alternatively or additionally, for some applications, external unit 100 is incorporated into a belt or strap configured to be worn around the patient's chest.

Figure 11:
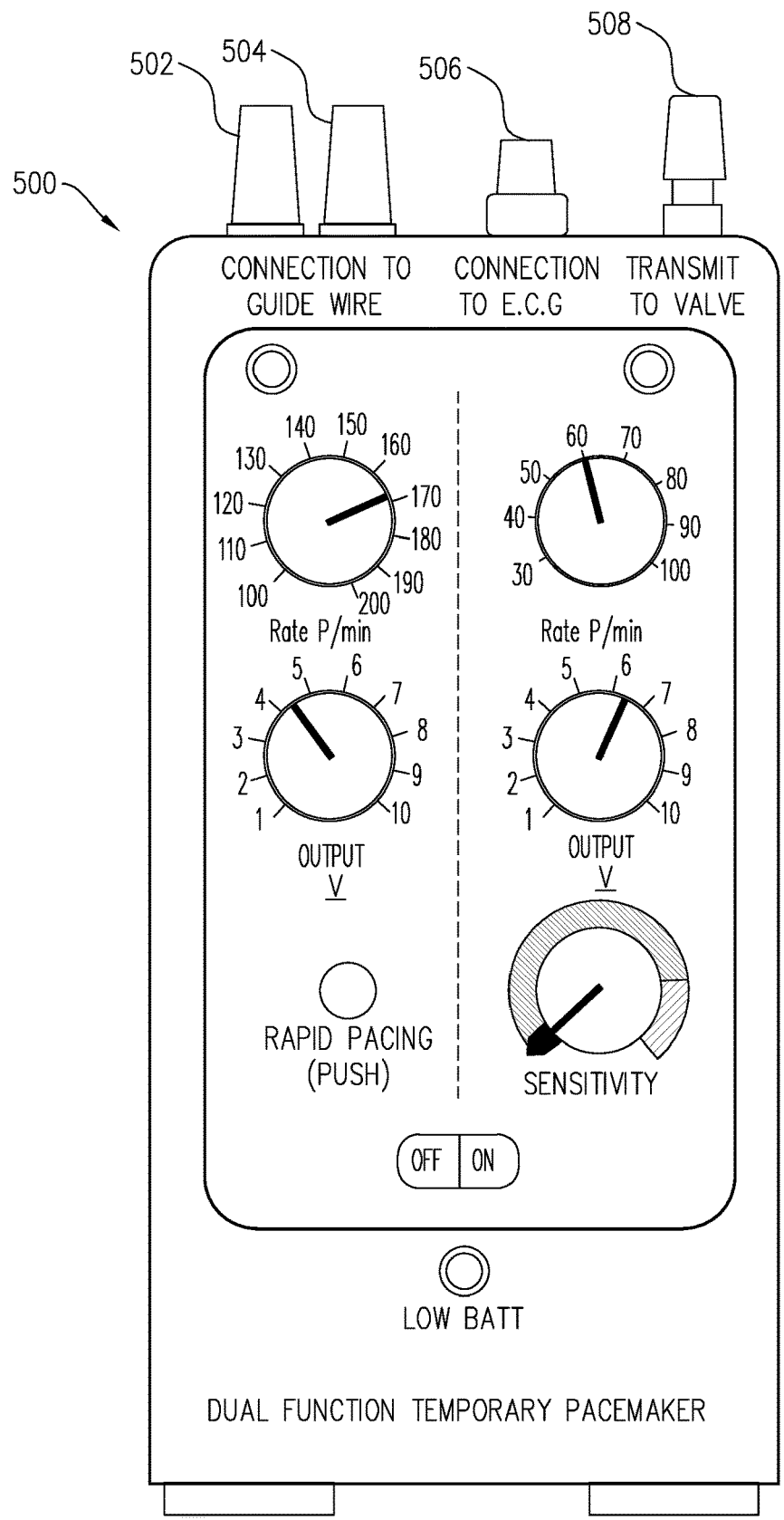
FIG. 11 is a schematic illustration of an external control unit, in accordance with an application of the present invention.

Reference is now made to FIG. 11, which is a schematic illustration of an external control unit 500, in accordance with an application of the present invention. For some applications, external control unit 500 may be configured to provide user-selectable dual-mode pacing, including rapid ventricular pacing for application during an implantation procedure, as described hereinabove with reference to FIGS. 10A-B, and post-implantation chronic bipolar pacing, such as described hereinabove with reference to FIG. 10D. External control unit 500 typically comprises delivery-system control circuitry 80, described hereinabove with reference to FIGS. 10A-B, and external-unit control circuitry 104. As such, external control unit 500 serves the dual role of both a component of delivery system 370, described hereinabove with reference to FIGS. 10A-C, and external unit 100, described hereinabove with reference to FIG. 10D.

External control unit 500 typically includes several electrical connectors, to which connection may be made, for example, using connector clips, as known in the art:
  an anode connector 502, for connection to anode 436 of delivery system 370;
  a cathode connector 504, for connection to cathode 430 of delivery system 370;
  an ECG connector 506, for connection to sensing skin ECG electrodes 106; and
  a coil connector 508, for connection to energy-transmission coil 102.

Figure 12:
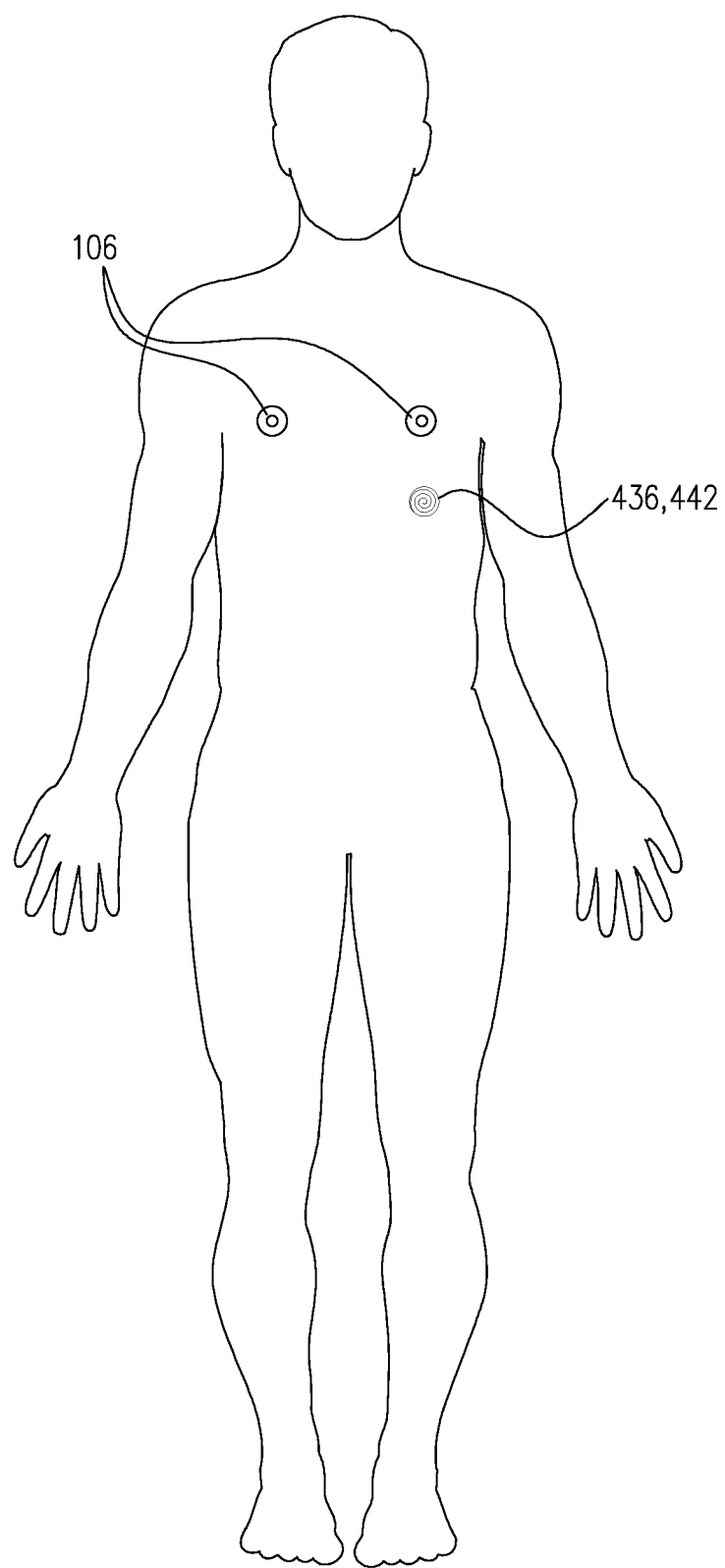
FIG. 12 is a schematic diagram of a patient showing exemplary locations of skin electrodes, in accordance with an application of the present invention.

Reference is now made to FIG. 12, which is a schematic diagram of a patient showing exemplary locations of skin electrodes, in accordance with an application of the present invention. FIG. 12 shows exemplary locations of sensing skin ECG electrodes 106, described hereinabove with reference to FIG. 10D, and anode skin electrode 442, described hereinabove with reference to FIGS. 10A-B.

Figure 13A:
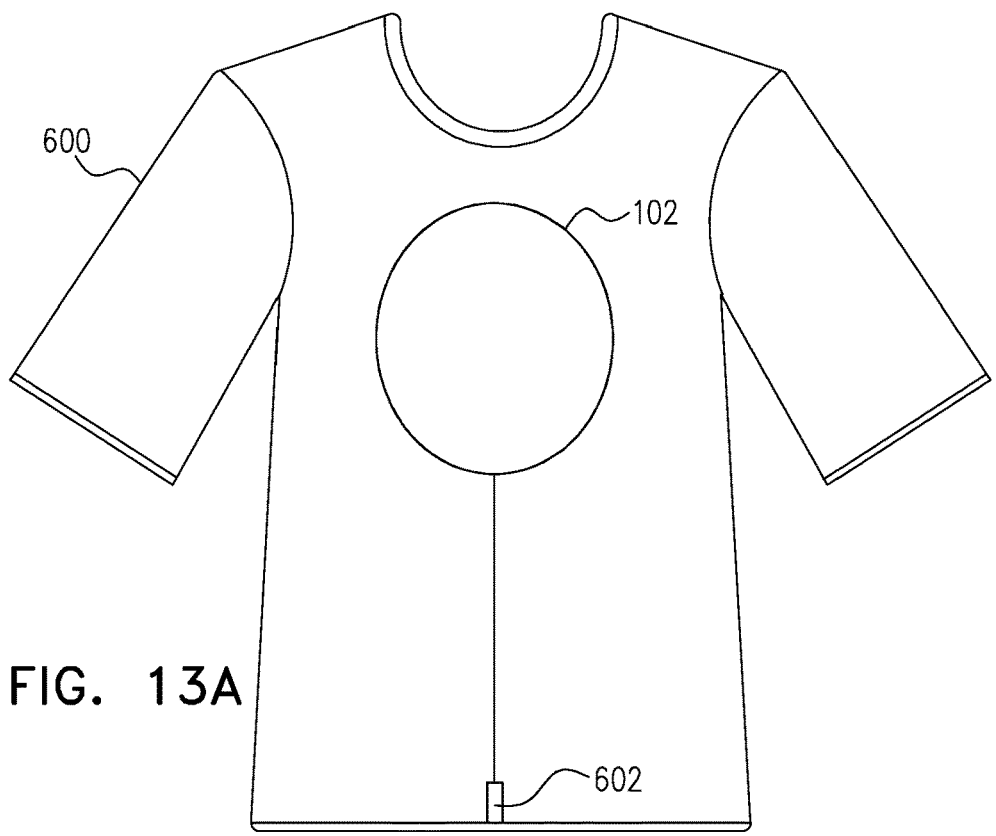
FIGS. 13A-B are schematic illustrations of a shirt with integrated components, in accordance with an application of the present invention.
Figure 13B:
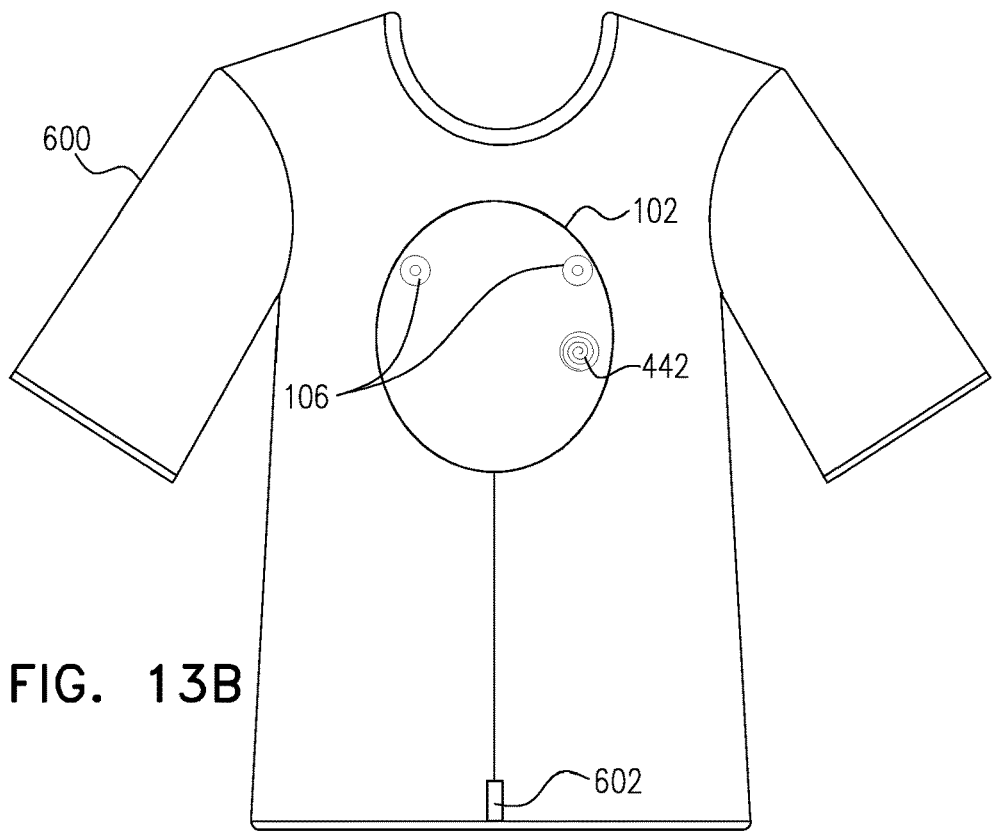

Reference is now made to FIGS. 13A-B, which are schematic illustrations of a shirt 600 with integrated components, in accordance with an application of the present invention. The components may be attached to a surface of the shirt, such as an inner surface, or embedded in the shirt. The components may include:
  transmission coil 102, described hereinabove with reference to FIG. 10D;
  sensing skin ECG electrodes 106, described hereinabove with reference to FIG. 10D; and/or
  anode skin electrode 442, described hereinabove with reference to FIGS. 10A-B.

Typically, shirt 600 further comprises a connector 602, for electrical connection to external control unit 500, described hereinabove with reference to FIG. 11.

Figure 13C:
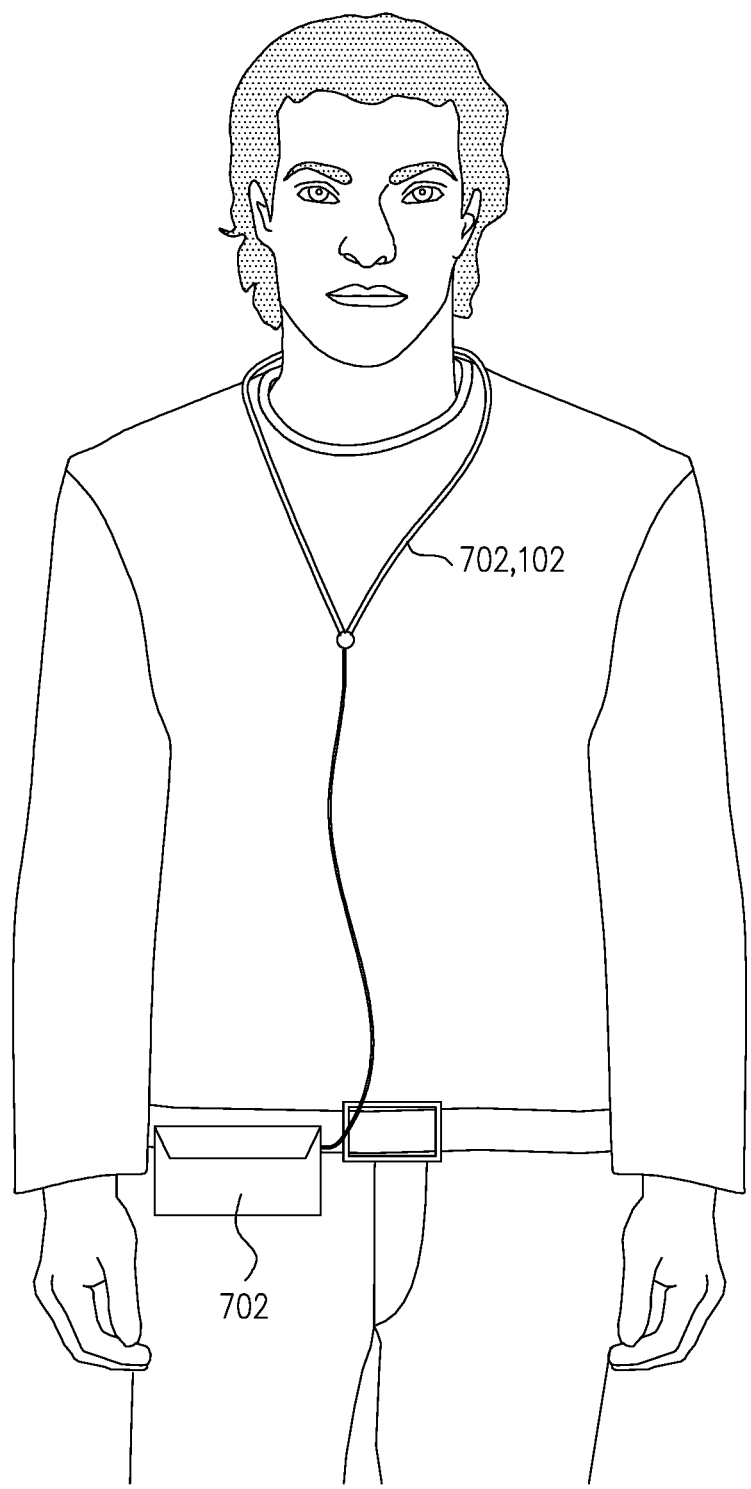
FIG. 13C is a schematic illustration of a necklace, in accordance with an application of the present invention.

Reference is now made to FIG. 13C, which is a schematic illustration of a necklace 700, in accordance with an application of the present invention. As described hereinabove with reference to FIG. 10B, necklace 700 comprises an integrated energy-transmission coil 102.

Alternatively, energy-transmission coil 102 may be integrated into a shirt around the collar, for placement around the patients neck.

A temporary pacemaker 702 may also be provided.

Figure 14A:
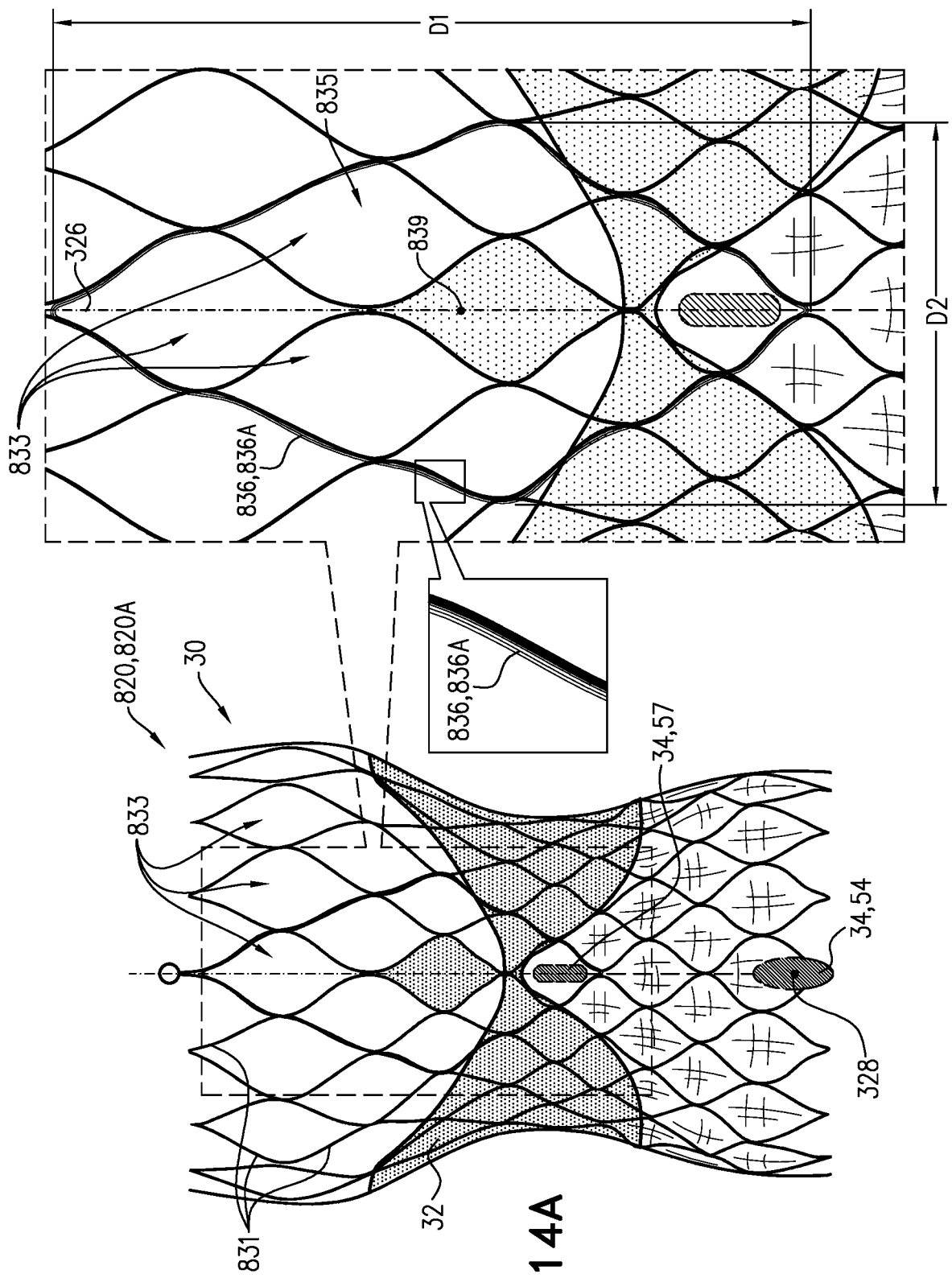
Figure 14B:
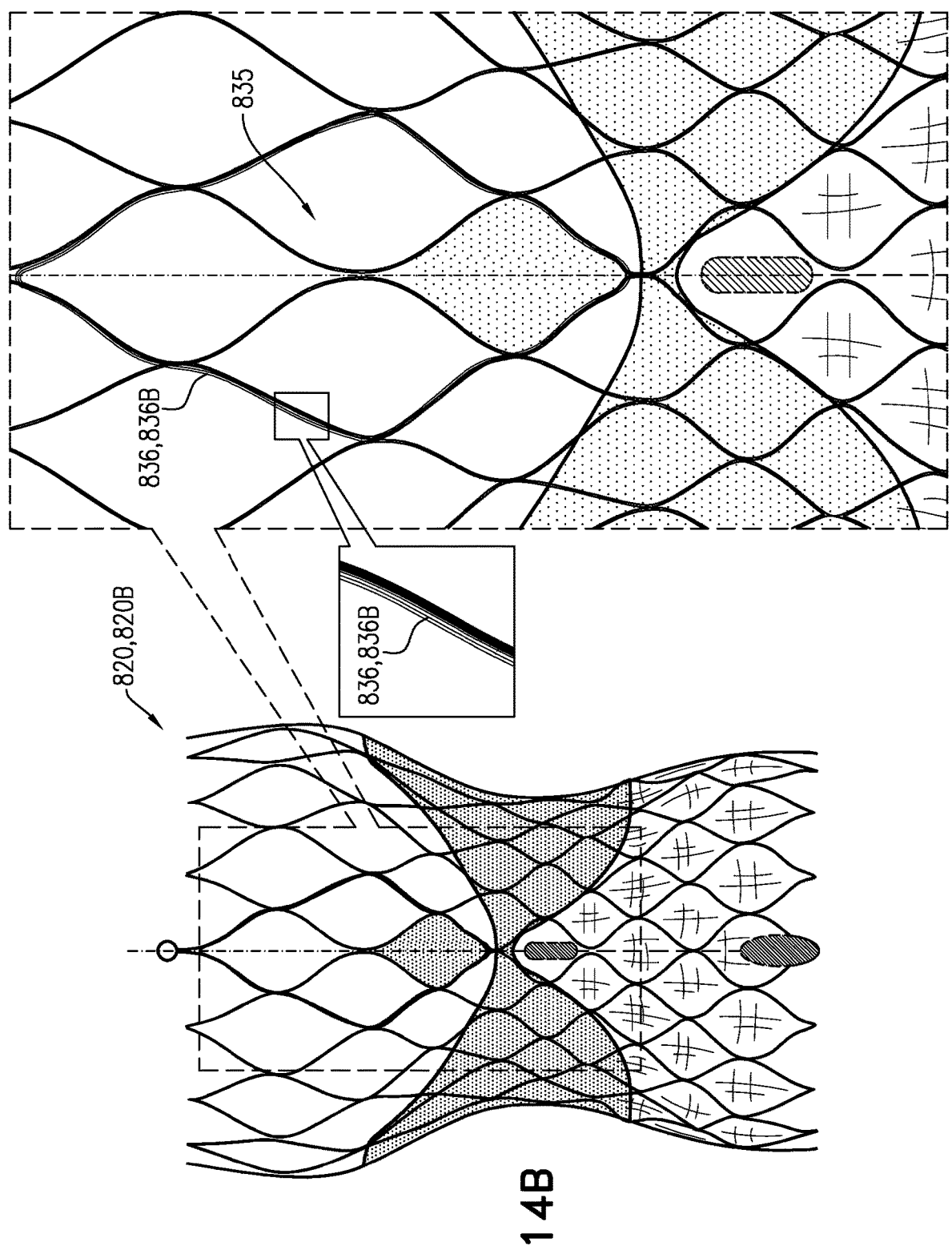

Reference is now made to FIGS. 14A-C, which are schematic illustrations of respective configurations of a prosthetic aortic valve 820, in accordance with respective applications of the present invention. Other than as described hereinbelow, prosthetic aortic valve 820 is generally similar to prosthetic aortic valve 320, described hereinabove with reference to FIGS. 6-7, and may implement any of the features thereof, mutatis mutandis. Alternatively, prosthetic aortic valve 820 may implement any of the features of prosthetic aortic valve 420, described hereinabove with reference to FIG. 9, mutatis mutandis, and/or of any of the other prosthetic aortic valves described herein, mutatis mutandis.

Prosthetic aortic valve 820 is shown in FIGS. 14A-C in an expanded configuration, which is similar to the expanded fully-deployed configuration described hereinbelow with reference to FIG. 15, except that in FIGS. 14A-C expansion of prosthetic aortic valve 820 is not limited by anatomy of a patient.

Prosthetic aortic valve 820 comprises:

frame 30;

plurality of prosthetic leaflets 32 coupled to frame 30;

electrodes 34, which include cathode 54 and anode 57, and which are mechanically coupled to frame 30; and a prosthetic-valve coil 836 coupled to frame 30 in non-wireless electrical communication with cathode 54 and anode 57.

Frame 30 typically comprises a stent or other structure, which is typically self-expanding, and may be formed by laser cutting or etching a metal alloy tube comprising, for example, stainless steel or a shape memory alloy such as Nitinol. In this configuration, frame 30 comprises interconnected stent struts 831 arranged so as to define interconnected stent cells 833. For some applications, one or more of electrodes 34 are coupled to frame 30 using techniques described in U.S. Pat. No. 9,526,637 to Dagan et al. and/or US 2016/0278951 to Dagan et al., both of which are incorporated herein by reference. For some applications, prosthetic-valve coil 836 comprises gold wire, in order to provide low resistance.

For some applications, such as shown, prosthetic aortic valve 820 does not comprise any commissural posts.

Prosthetic-valve coil 836, is coupled to a plurality of stent struts 831, running along stent struts 831 so as to surround a plurality 835 of stent cells 833 when prosthetic aortic valve 820 is in the expanded fully-deployed configuration upon release from the delivery sheath. For example, at least 50% (e.g., at least 75%) of a perimeter of prosthetic-valve coil 836 may run along stent struts 831, such as 100% of the perimeter, as shown in the drawings. Stent struts 831 are shaped so as to allowing efficient crimping (compression) of frame 30 when in the constrained delivery configuration within the delivery sheath. The coupling of prosthetic-valve coil 836 to stent struts 81, running along the stent struts, causes prosthetic-valve coil 836 to be crimped efficiently together with the frame.

FIGS. 14A and 14B show prosthetic-valve coils 836A and 836B, respectively, which are exemplary configurations of prosthetic-valve coil 836. It will be appreciated that many other configurations are possible within the scope of the present invention.

For some applications, prosthetic-valve coil 836 is shaped generally as a diamond when prosthetic aortic valve 820 is in the expanded fully-deployed configuration, such as shown in the drawings.

Typically, plurality 835 of stent cells 833 surrounded by prosthetic-valve coil 836 comprises at least 4 stent cells 833, such as shown in FIGS. 14A and 14B, for example, at least 9 stent cells 833, such as shown in FIG. 14A, or at least 16 stent cells 833 (configuration not shown in FIG. 14A or 14B). Optionally, plurality 835 of stent cells 833 surrounded by prosthetic-valve coil 836 comprises no more than 32 stent cells 833.

For some applications, when prosthetic aortic valve 820 is in the expanded fully-deployed configuration, (a) a centroid 839 of prosthetic-valve coil 836 and (b) centroid 328 of cathode 54 are rotationally offset from each other about central longitudinal axis 326 by an angle of at least 150 degrees (e.g., at least 160 degrees, typically 180 degrees) when prosthetic aortic valve 820 is in the expanded fully-deployed configuration.

For some applications, prosthetic-valve coil 836 has a perimeter of at least 5 cm, no more than 8 cm, and/or between 4 and 8 cm when prosthetic aortic valve 820 is in the expanded fully-deployed configuration.

For some applications, prosthetic-valve coil 836, when in the expanded fully-deployed configuration, has:

a first dimension D1 of at least 2 cm, no more than 4 cm, and/or between 2 and 4 cm, the first dimension D1 measured parallel to central longitudinal axis 326 defined by frame 30 when prosthetic aortic valve 820 is in the expanded fully-deployed configuration, and/or a second dimension D2 of at least 1 cm, no more than 3 cm, and/or between 1 and 3 cm, the second dimension D2 measured around central longitudinal axis 326, and/or between 30 and 180 degrees, such as between 30 and 150 degrees or 90 and 180 degrees (e.g., between 90 and 150 degrees, such as between 90 and 120 degrees), the second dimension D2 measured in degrees around frame 30 with respect to central longitudinal axis 326.

For some applications, wherein prosthetic-valve coil 836 surrounds an area of at least 1 cm2, no more than 4 cm2, and/or between 1 and 4 cm2 when prosthetic aortic valve 820 is in the expanded fully-deployed configuration.

For some applications, prosthetic-valve coil 836 is shaped so as to define 1 to 4 turns (by way of example, 3 turns are shown in the drawings).

For some applications, prosthetic-valve coil 836 is shaped so that no single line crosses, more than twice, a projection of prosthetic-valve coil 836 onto a best-fit plane when prosthetic aortic valve 820 is in the expanded fully-deployed configuration (although the single line will cross the turns of the coil more than twice in configurations in which the coil is shaped so as to define more than one turn).

For some applications, prosthetic-valve coil 836 is not shaped so as to define any zigzags when prosthetic aortic valve 820 is in the expanded fully-deployed configuration.

Reference is made to FIGS. 14A-B and 14C. In the configuration shown in FIGS. 14A-B, prosthetic aortic valves 820A and 820B comprises exactly one prosthetic-valve coil 836.

FIG. 14C shows a prosthetic aortic valve 820C. In this configuration, prosthetic-valve coil 836 is a first prosthetic-valve coil 836C, the plurality of stent struts 831 is a first plurality of stent struts 831, and plurality 835 of stent cells 833 is a first plurality 835C of stent cells 833. Prosthetic aortic valve 820 further comprises a second prosthetic-valve coil 836D, which is in non-wireless electrical communication with cathode 54 and anode 57, and is coupled to a second plurality of stent struts 831, running along stent struts 831 so as to surround a second plurality 835D of stent cells 833 when prosthetic aortic valve 820 is in the expanded fully-deployed configuration. Typically, first and second pluralities 835C and 835D of stent cells 833 do not include any common stent cells 833. Optionally, first and second prosthetic-valve coils 836C and 836D are not coupled to any comment stent struts 831.

For some applications, first and second prosthetic-valve coils 836C and 836D comprise a single wire 837 that is shaped so as to define both the first and the second prosthetic-valve coils.

Typically, respective centroids of first and second prosthetic-valve coils 836C and 836D are offset from each other by at least 90 degrees (e.g., at least 150 degrees, typically 180 degrees) around central longitudinal axis 326 when prosthetic aortic valve 820 is in the expanded fully-deployed configuration.

Figure 15:
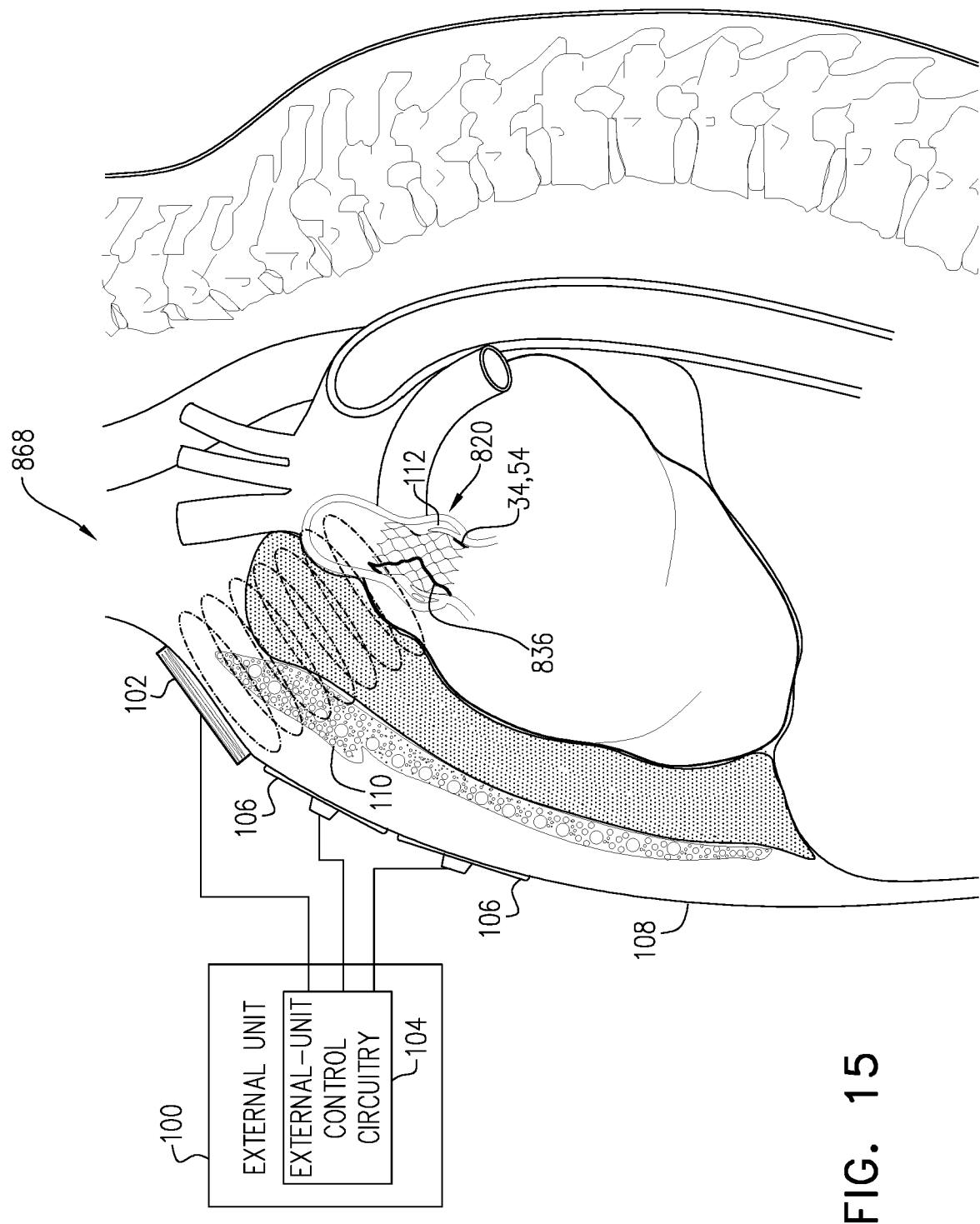
FIG. 15 is a schematic illustration of another valve prosthesis system upon deployment of the prosthetic aortic valve of FIGS. 14A-B, in accordance with an application of the present invention.

Reference is now made to FIG. 15, which is a schematic illustration of a valve prosthesis system 868 upon deployment of prosthetic aortic valve 820, in accordance with an application of the present invention. Valve prosthesis system 868 comprises prosthetic aortic valve 820 rather than prosthetic aortic valve 320, but otherwise may implement any of the features of valve prosthesis system 368, described hereinabove with reference to FIGS. 10A-D, mutatis mutandis, and/or valve prosthesis system 68, described hereinabove with reference to FIGS. 4A-C, mutatis mutandis.

The techniques described herein for prosthetic aortic valves 20, 120, 320, 420, and 820 may be alternatively used, mutatis mutandis, for non-aortic prosthetic valves, such as prosthetic mitral or tricuspid valves.

In an embodiment, techniques and apparatus described in one or more of the following patents and/or applications, which are assigned to the assignee of the present application and are incorporated herein by reference, are combined with techniques and apparatus described herein:

U.S. Pat. No. 10,543,083 to Gross
European Patent Application Publication EP 3508113 A1 to Gross
U.S. Pat. No. 10,835,750 to Gross
US Patent Application Publication 2020/0261224 to Gross
International Patent Application PCT/IL2021/050016, filed Jan. 6, 2021
International Patent Application PCT/IL2021/050017, filed Jan. 6, 2021
U.S. patent application Ser. No. 17/142,729, filed Jan. 6, 2021, now U.S. Pat. No. 11,065,451

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A valve prosthesis system comprising:
a prosthetic aortic valve, which is configured to be delivered to a native aortic valve of a patient in a constrained delivery configuration within a delivery sheath, and which comprises:
a frame, which comprises interconnected stent struts arranged so as to define interconnected stent cells;
a plurality of prosthetic leaflets coupled to the frame;
a cathode and an anode, which are mechanically coupled to the frame; and
a prosthetic-valve coil, which is in non-wireless electrical communication with the cathode and the anode, and is coupled to a plurality of the stent struts, running along the stent struts so as to surround a plurality of the stent cells when the prosthetic aortic valve is in an expanded fully-deployed configuration upon release from the delivery sheath; and
an external unit, which is configured to be disposed outside a body of the patient, and which comprises:
an energy-transmission coil; and
external-unit control circuitry, which is configured to drive the energy-transmission coil to wirelessly transfer energy to the prosthetic-valve coil by inductive coupling,
wherein the external-unit control circuitry is configured to drive the cathode and the anode to apply a pacing signal to a heart of the patient, by wirelessly transferring the energy from the energy-transmission coil to the prosthetic-valve coil by inductive coupling.

2. The valve prosthesis system according to claim 1, wherein the prosthetic-valve coil is shaped generally as a diamond when the prosthetic aortic valve is in the expanded fully-deployed configuration.

3. The valve prosthesis system according to claim 1, wherein the prosthetic-valve coil is shaped so that no single line crosses, more than twice, a projection of the prosthetic-valve coil onto a best-fit plane when the prosthetic aortic valve is in the expanded fully-deployed configuration.

4. The valve prosthesis system according to claim 1, wherein the prosthetic-valve coil is not shaped so as to define any zigzags when the prosthetic aortic valve is in the expanded fully-deployed configuration.

5. The valve prosthesis system according to claim 1, wherein the plurality of the stent cells surrounded by the prosthetic-valve coil comprises at least 4 stent cells.

6. The valve prosthesis system according to claim 5, wherein the plurality of the stent cells surrounded by the prosthetic-valve coil comprises at least 9 stent cells.

7. The valve prosthesis system according to claim 1, wherein the prosthetic-valve coil has a perimeter of between 4 and 8 cm when the prosthetic aortic valve is in the expanded fully-deployed configuration.

8. The valve prosthesis system according to claim 1, wherein the prosthetic-valve coil is shaped so as to define 1 to 4 turns.

9. The valve prosthesis system according to claim 1, wherein the prosthetic-valve coil has a first dimension of between 2 and 4 cm, the first dimension measured parallel to a central longitudinal axis defined by the frame when the prosthetic aortic valve is in the expanded fully-deployed configuration.

10. The valve prosthesis system according to claim 1, wherein the prosthetic-valve coil has a second dimension of between 1 and 3 cm, the second dimension measured around a central longitudinal axis defined by the frame when the prosthetic aortic valve is in the expanded fully-deployed configuration.

11. The valve prosthesis system according to claim 1, wherein the prosthetic-valve coil has a second dimension of between 30 and 180 degrees, the second dimension measured in degrees around the frame with respect to a central longitudinal axis defined by the frame when the prosthetic aortic valve is in the expanded fully-deployed configuration.

12. The valve prosthesis system according to claim 1, wherein the prosthetic-valve coil surrounds an area of between 1 and 4 cm2 when the prosthetic aortic valve is in the expanded fully-deployed configuration.

13. The valve prosthesis system according to claim 1, wherein the stent struts comprise a shape-memory alloy.

14. The valve prosthesis system according to claim 1, wherein the prosthetic aortic valve does not comprise any commissural posts.

15. The valve prosthesis system according to claim 1, wherein the prosthetic aortic valve comprises exactly one prosthetic-valve coil.

16. The valve prosthesis system according to claim 1,
wherein the prosthetic-valve coil is a first prosthetic-valve coil, the plurality of the stent struts is a first plurality of the stent struts, and the plurality of the stent cells is a first plurality of the stent cells,
wherein the prosthetic aortic valve further comprises a second prosthetic-valve coil, which is in non-wireless electrical communication with the cathode and the anode, and is coupled to a second plurality of the stent struts, running along the stent struts so as to surround a second plurality of the stent cells when the prosthetic aortic valve is in the expanded fully-deployed configuration, and
wherein the first and the second pluralities of the stent cells do not include any common stent cells.

17. The valve prosthesis system according to claim 16, wherein the first and the second prosthetic-valve coils comprise a single wire that is shaped so as to define both the first and the second prosthetic-valve coils.

18. The valve prosthesis system according to claim 16, wherein respective centroids of the first and the second prosthetic-valve coils are offset from each other by at least 90 degrees around a central longitudinal axis defined by the frame when the prosthetic aortic valve is in the expanded fully-deployed configuration.

19. The valve prosthesis system according to claim 1, wherein the prosthetic aortic valve does not comprise any active electronic components.

20. The valve prosthesis system according to claim 1, wherein when the prosthetic aortic valve is in the expanded fully-deployed configuration, (a) a centroid of the prosthetic-valve coil and the frame and (b) a centroid of the cathode are rotationally offset from each other about a central longitudinal axis by an angle of at least 150 degrees when the prosthetic aortic valve is in the expanded fully-deployed configuration, the central longitudinal axis defined by the frame when the prosthetic aortic valve is in the expanded fully-deployed configuration.

21. The valve prosthesis system according to claim 1,
wherein the external-unit control circuitry is configured to wirelessly transfer the energy by generating a plurality of AC pulses, each including a train of AC bursts, and
wherein the prosthetic aortic valve comprises a passive diode, which is coupled in electrical communication with the prosthetic-valve coil, and is configured to rectify current in the prosthetic-valve coil.

22. The valve prosthesis system according to claim 21, wherein the external-unit control circuitry is configured to generate the train of AC bursts at a frequency of between 12 and 20 MHz.

23. A method comprising:
delivering, to a native aortic valve of a patient, via vasculature of the patient, a prosthetic aortic valve while in a constrained delivery configuration within a delivery sheath, the prosthetic aortic valve including (a) a frame, which comprises interconnected stent struts arranged so as to define interconnected stent cells, (b) a plurality of prosthetic leaflets coupled to the frame, (c) a cathode and an anode, which are mechanically coupled to the frame, and (d) a prosthetic-valve coil, which is in non-wireless electrical communication with the cathode and the anode, and is coupled to a plurality of the stent struts, running along the stent struts;
releasing the prosthetic aortic valve from the delivery sheath, such that the prosthetic aortic valve transitions to an expanded fully-deployed configuration, in which the prosthetic-valve coil surrounds a plurality of the stent cells; and
activating external-unit control circuitry of an external unit, disposed outside a body of the patient, to drive an energy-transmission coil of the external unit to wirelessly transfer energy to the prosthetic-valve coil by inductive coupling,
wherein activating the external-unit control circuitry comprises activating the external-unit control circuitry to drive the cathode and the anode to apply a pacing signal to a heart of the patient, by wirelessly transferring the energy from the energy-transmission coil to the prosthetic-valve coil by inductive coupling.

24. The method according to claim 23, further comprising rotationally orienting the prosthetic aortic valve such that the prosthetic-valve coil faces generally anterio-superiorly toward a sternum of the patient.

25. The method according to claim 24,
wherein when the prosthetic aortic valve is in the expanded fully-deployed configuration, (a) a centroid of the prosthetic-valve coil and (b) a centroid of the cathode are rotationally offset from each other about a central longitudinal axis by an angle of at least 150 degrees when the prosthetic aortic valve is in the expanded fully-deployed configuration, the central longitudinal axis defined by the frame when the prosthetic aortic valve is in the expanded fully-deployed configuration, and
wherein rotationally orienting the prosthetic aortic valve comprises aligning the cathode adjacent to cardiac tissue near a bundle of His of the patient, so as to automatically align the prosthetic-valve coil facing generally anterio-superiorly toward a sternum of the patient.

26. The method according to claim 23, further comprising positioning the energy-transmission coil against a chest of the patient, over a sternum of the patient.

* * * * *